(12) United States Patent
Dai et al.

(10) Patent No.: US 11,098,060 B2
(45) Date of Patent: Aug. 24, 2021

(54) MACROCYCLE CONTAINING AMINOPYRAZOLE AND PYRIMIDINE AND PHARMACEUTICAL COMPOSITION AND USE THEREOF

(71) Applicants: CHIA TAI TIANQING PHARMACEUTICAL GROUP CO., LTD., Jiangsu (CN); CENTAURUS BIOPHARMA CO., LTD., Beijing (CN); Lianyungang Runzhong Pharmaceutical Co., Ltd., Jiangsu (CN)

(72) Inventors: Liguang Dai, Beijing (CN); Xiaowei Duan, Beijing (CN); Yanqing Yang, Beijing (CN); Xijie Liu, Beijing (CN); Hongjuan Li, Beijing (CN); Na Zhao, Beijing (CN); Yinghui Sun, Beijing (CN); Fansheng Kong, Beijing (CN); Jiuqing Zhang, Beijing (CN); Yizhong Zhu, Jiangsu (CN); Ling Yang, Jiangsu (CN); Fei Liu, Jiangsu (CN)

(73) Assignees: CHIA TAI TIANQING PHARMACEUTICAL GROUP CO., LTD., Jiangsu (CN); CENTAURUS BIOPHARMA CO., LTD., Beijing (CN); LIANYUNGANG RUNZHONG PHARMACEUTICAL CO., LTD., Jiangsu (CN)

( * ) Notice: Subject to any disclaimer, the term of this patent is extended or adjusted under 35 U.S.C. 154(b) by 0 days.

(21) Appl. No.: 16/641,187

(22) PCT Filed: Aug. 23, 2018

(86) PCT No.: PCT/CN2018/101960
§ 371 (c)(1),
(2) Date: Feb. 21, 2020

(87) PCT Pub. No.: WO2019/037761
PCT Pub. Date: Feb. 28, 2019

(65) Prior Publication Data
US 2020/0291042 A1    Sep. 17, 2020

(30) Foreign Application Priority Data

Aug. 23, 2017  (CN) .................. 201710728132.X

(51) Int. Cl.
| | |
|---|---|
| C07D 498/22 | (2006.01) |
| C07D 471/22 | (2006.01) |
| C07D 498/18 | (2006.01) |
| A61P 35/04 | (2006.01) |

(52) U.S. Cl.
CPC ............ *C07D 498/22* (2013.01); *A61P 35/04* (2018.01); *C07D 471/22* (2013.01); *C07D 498/18* (2013.01)

(58) Field of Classification Search
CPC ... C07D 471/22; C07D 498/22; C07D 498/18
See application file for complete search history.

(56) References Cited

FOREIGN PATENT DOCUMENTS

| EP | 3 533 796 A1 | 9/2019 |
|---|---|---|
| WO | 2010/048314 A1 | 4/2010 |
| WO | 2011/146336 A1 | 11/2011 |
| WO | 2017/004342 A1 | 1/2017 |

*Primary Examiner* — Susanna Moore
(74) *Attorney, Agent, or Firm* — Seed Intellectual Property Law Group LLP

(57) ABSTRACT

The present application relates to a macrocycle containing aminopyrazole and pyrimidine, which is represented by formula (I), a pharmaceutical composition thereof, and a use thereof in inhibiting tropomyosin receptor kinase (Trk) activity and in treating diseases in mammals that are mediated by Trk.

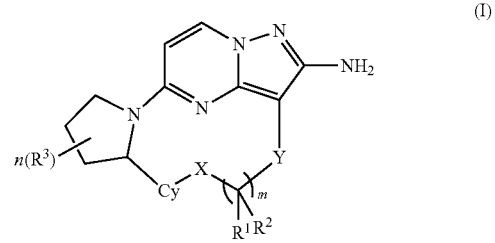

(I)

20 Claims, No Drawings

MACROCYCLE CONTAINING AMINOPYRAZOLE AND PYRIMIDINE AND PHARMACEUTICAL COMPOSITION AND USE THEREOF

REFERENCE TO RELATED APPLICATION

The present application claims the priority and benefit of the Chinese invention patent application No. 201710728132.X filed with the China National Intellectual Property Administration on Aug. 23, 2017, which is incorporated herein by reference in its entirety.

TECHNICAL FIELD

The present application relates to an aminopyrazolopyrimidine-containing macrocyclic compound, a process for preparing the same, a pharmaceutical composition comprising the compound, and a use thereof in the treatment of a disease mediated by Trk kinase.

BACKGROUND

NTRK/TRK (Tropomyosin receptor kinase) is a neurotrophic factor tyrosine kinase receptor, and belongs to a family of receptor tyrosine kinase. The Trk family mainly includes three members, namely, NTRK1/TrkA, NTRK2/TrkB and NTRK3/TrkC, wherein NGF (nerve growth factor) binds to TrkA; BDNF (derived neurotrophic factor) binds to TrkB; and NT3 (neurotrophic factor 3) binds to TrkC.

Trk kinase plays an important physiological role in the development of nerves. A large number of studies have shown that the activation of Trk signaling pathway is also strongly correlated with the occurrence and development of a tumor. Activated Trk signaling proteins are found in neuroblastoma, lung adenocarcinoma, pancreatic carcinoma, breast carcinoma, and so on. The discovery of various Trk fusion proteins in recent years has further demonstrated their biological function in promoting tumorigenesis. The earliest TPM3-TrkA fusion protein was found in colon cancer cells. Afterwards, different types of Trk fusion proteins, such as CD74-NTRK1, MPRIP-NTRK1, QKI-NTRK2, ETV6-NTRK3, BTB1-NTRK3 and so on, were found in different types of tumor patient samples suffering from, such as lung cancer, head and neck cancer, breast cancer, thyroid cancer, glioma, and so on. These different NTRK fusion proteins per se are in a highly activated state of kinase activity without the need to bind to a ligand, and thereby can continuously phosphorylate the downstream signaling pathways, induce cell proliferation, and promote the occurrence and development of a tumor. Moreover, Trk inhibitors are effective in inhibiting tumor growth and preventing tumor metastasis in a preclinical model of a cancer. Therefore, in recent years, Trk fusion proteins have become an effective anti-cancer target. For example, WO2010048314, WO2012116217, WO2010033941, WO2011146336, WO2017035354 and so on disclose Trk kinase inhibitors having different core structures.

In view of the important physiological functions of Trk kinases, it is essential to find an effective Trk kinase inhibitor.

SUMMARY OF THE INVENTION

In an aspect, the present application relates to a compound of Formula (I)

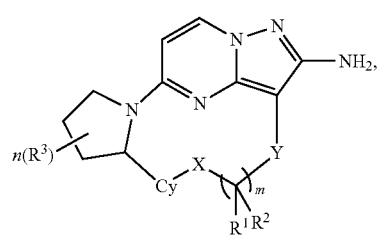

Formula (I)

or a pharmaceutically acceptable salt thereof, wherein
X is selected from the group consisting of a bond, —O—, —S—, and —NR$^4$—;
Y is selected from the group consisting of

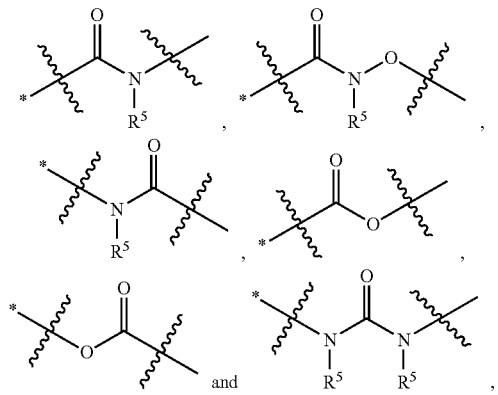

wherein "*" represents the end of the Y group attached to the aminopyrazolopyrimidine ring;
R$^1$ and R$^2$ are independently selected from the group consisting of hydrogen, C$_1$-C$_6$ alkyl, C$_1$-C$_6$ alkoxy, halo, nitro, hydroxy, cyano and amino, wherein C$_1$-C$_6$ alkyl and C$_1$-C$_6$ alkoxy are optionally substituted with one or more substituents independently selected from the group consisting of halo, nitro, hydroxy, cyano and amino; or
R$^1$ and R$^2$ are taken together to form

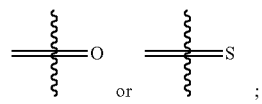

R$^3$ is selected from the group consisting of C$_1$-C$_6$ alkyl, C$_1$-C$_6$ alkoxy, halo, nitro, hydroxy, cyano and amino, wherein C$_1$-C$_6$ alkyl and C$_1$-C$_6$ alkoxy are optionally substituted with one or more substituents independently selected from the group consisting of halo, nitro, hydroxy, cyano and amino;
R$^4$ and R$^5$ are independently selected from the group consisting of hydrogen and C$_1$-C$_6$ alkyl;
m is selected from 0, 1, 2, 3, 4, 5 or 6;
n is selected from 0, 1, 2, 3, 4, 5, 6 or 7;
Cy is selected from the group consisting of a 6- to 10-membered aromatic ring, a 5- to 10-membered aromatic heterocycle, a 3- to 10-membered aliphatic heterocycle, and a 3- to 10-membered cycloalkyl ring, wherein the 6- to 10-membered aromatic ring, 5- to 10-membered aromatic heterocycle, 3- to 10-membered aliphatic heterocycle, or 3- to 10-membered cycloalkyl ring is optionally substituted with one or more substituents independently selected from the group consisting of $C_1$-$C_6$ alkyl, $C_1$-$C_6$ alkoxy, halo, nitro, hydroxy, cyano, and amino.

In another aspect, the present application relates to a pharmaceutical composition comprising a compound of Formula (I) of the present application, or a pharmaceutically acceptable salt thereof.

In a further aspect, the present application relates to a method for treating a disease mediated by Trk kinase in a mammal, comprising administering to the mammal, preferably a human, in need thereof a therapeutically effective amount of the compound of Formula (I) or a pharmaceutically acceptable salt thereof, or a pharmaceutical composition thereof.

In still another aspect, the present application relates to a use of the compound of Formula (I) or a pharmaceutically acceptable salt thereof, or a pharmaceutical composition thereof in the preparation of a medicament for the prophylaxis or treatment of a disease mediated by Trk kinase.

In yet another aspect, the present application relates to the compound of Formula (I) or a pharmaceutically acceptable salt thereof, or a pharmaceutical composition thereof for use in the prophylaxis or treatment of a disease mediated by Trk kinase.

DETAILED DESCRIPTION OF THE INVENTION

The present application relates to a compound of Formula (I)

Formula (I)

or a pharmaceutically acceptable salt thereof, wherein
X is selected from the group consisting of a bond, —O—, —S—, and —NR$^4$—;
Y is selected from the group consisting of wherein "*" represents the end of the Y group attached to the aminopyrazolopyrimidine ring;
R$^1$ and R$^2$ are independently selected from the group consisting of hydrogen, $C_1$-$C_6$ alkyl, $C_1$-$C_6$ alkoxy, halo, nitro, hydroxy, cyano and amino, wherein $C_1$-$C_6$ alkyl and $C_1$-$C_6$ alkoxy are optionally substituted with one or more substituents independently selected from the group consisting of halo, nitro, hydroxy, cyano and amino; or
R$^1$ and R$^2$ are taken together to form R$^3$ is selected from the group consisting of $C_1$-$C_6$ alkyl, $C_1$-$C_6$ alkoxy, halo, nitro, hydroxy, cyano and amino, wherein $C_1$-$C_6$ alkyl and $C_1$-$C_6$ alkoxy are optionally substituted with one or more substituents independently selected from the group consisting of halo, nitro, hydroxy, cyano and amino;
R$^4$ and R$^5$ are independently selected from the group consisting of hydrogen and $C_1$-$C_6$ alkyl;
m is selected from 0, 1, 2, 3, 4, 5 or 6;
n is selected from 0, 1, 2, 3, 4, 5, 6 or 7;
Cy is selected from the group consisting of a 6- to 10-membered aromatic ring, a 5- to 10-membered aromatic heterocycle, a 3- to 10-membered aliphatic heterocycle, and a 3- to 10-membered cycloalkyl ring, wherein the 6- to 10-membered aromatic ring, 5- to 10-membered aromatic heterocycle, 3- to 10-membered aliphatic heterocycle, or 3- to 10-membered cycloalkyl ring is optionally substituted with one or more substituents independently selected from the group consisting of $C_1$-$C_6$ alkyl, $C_1$-$C_6$ alkoxy, halo, nitro, hydroxy, cyano, and amino.

In some embodiments, X is selected from the group consisting of a bond and —O—;
In some embodiments, R$^4$ is selected from the group consisting of hydrogen and $C_1$-$C_3$ alkyl, preferably hydrogen.

In some embodiments, Y is selected from the group consisting of wherein "*" represents the end of the Y group attached to the aminopyrazolopyrimidine ring.

In some embodiments, $R^5$ is selected from the group consisting of hydrogen and $C_1$-$C_3$ alkyl. In some typical embodiments, $R^5$ is selected from the group consisting of hydrogen and methyl.

In some more typical embodiments, Y is selected from the group consisting of *—CONH—, *—CON(CH$_3$)— and *—CONHO—, wherein "*" represents the end of the Y group attached to the aminopyrazolopyrimidine ring.

In some embodiments, $R^1$ and $R^2$ are independently selected from the group consisting of hydrogen, $C_1$-$C_3$ alkyl, $C_1$-$C_3$ alkoxy, fluoro, chloro, bromo, iodo, nitro, hydroxy, cyano, and amino, wherein $C_1$-$C_3$ alkyl and $C_1$-$C_3$ alkoxy are optionally substituted with one or more substituents independently selected from the group consisting of fluoro, chloro, bromo, iodo, nitro, hydroxy, cyano, and amino.

In some typical embodiments, $R^1$ and $R^2$ are independently selected from the group consisting of hydrogen, fluoro, and $C_1$-$C_3$ alkyl. In some more typical embodiments, $R^1$ and $R^2$ are independently selected from the group consisting of hydrogen, fluoro, and methyl.

In some embodiments, m is selected from 1, 2, 3, 4, or 5. In some typical embodiments, m is selected from 2, 3, or 4.

In some most typical embodiments, the structural unit

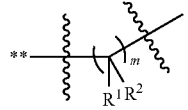

is selected from the group consisting of

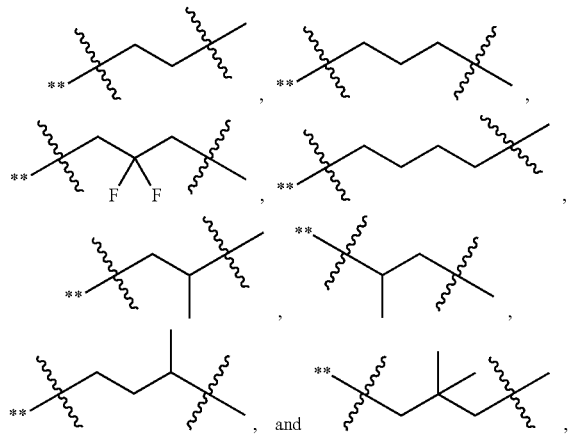

wherein ** represents the end of the structural unit

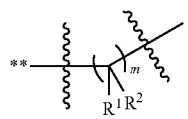

attached to X.

In some most typical embodiments, the structural unit

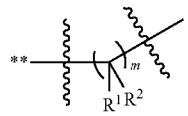

is selected from the group consisting of

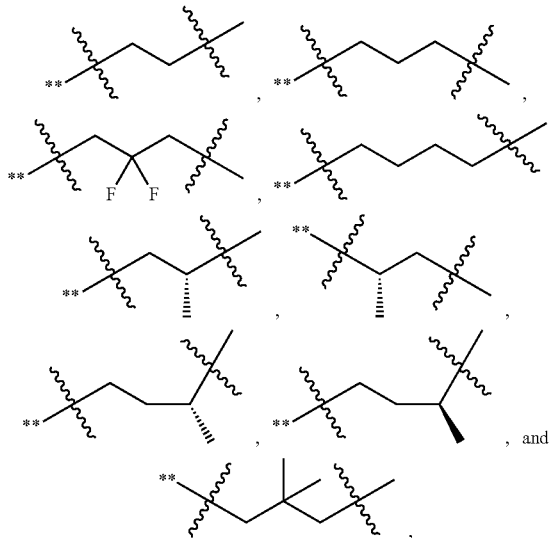

wherein ** represents the end of the structural unit

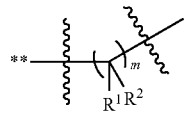

attached to X.

In some embodiments, $R^3$ is selected from the group consisting of $C_1$-$C_3$ alkyl, $C_1$-$C_3$ alkoxy, fluoro, chloro, bromo, iodo, nitro, hydroxy, cyano, and amino, wherein $C_1$-$C_3$ alkyl and $C_1$-$C_3$ alkoxy are optionally substituted with one or more substituents independently selected from the group consisting of fluoro, chloro, bromo, iodo, nitro, hydroxy, cyano, and amino.

In some typical embodiments, $R^3$ is selected from the group consisting of fluoro, chloro, bromo, iodo, and hydroxy. In some more typical embodiments, $R^3$ is selected from the group consisting of fluoro and hydroxy.

In some embodiments, n is selected from 0, 1, 2, or 3. In some typical embodiments, n is selected from 0 or 1.

In some embodiments, Cy is selected from the group consisting of benzene ring, naphthalene ring, pyrrole, furan, thiophene, imidazole, oxazole, pyrazole, pyridine, pyrimidine, pyrazine, quinoline, isoquinoline, benzofuran, benzothiophene, indole, isoindole, oxirane, tetrahydrofuran, dihydrofuran, pyrrolidine, dihydropyrrolidine, 2H-pyridine, piperidine, piperazine, pyrazolidine, tetrahydropyran, morpholine, thiomorpholine, tetrahydrothiophene, cyclopropane, cyclopentane, and cyclohexane, each of which is optionally substituted with one or more substituents independently selected from the group consisting of $C_1$-$C_3$ alkyl, $C_1$-$C_3$ alkoxy,

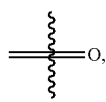

fluoro, chloro, bromo, iodo, nitro, hydroxy, cyano, and amino.

In some typical embodiments, Cy is selected from the group consisting of benzene ring, pyridine, and 1,2-2H-pyridine, each of which is optionally substituted with one or more substituents independently selected from the group consisting of fluoro and

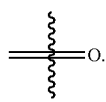

In some more typical embodiments, Cy is selected from the group consisting of

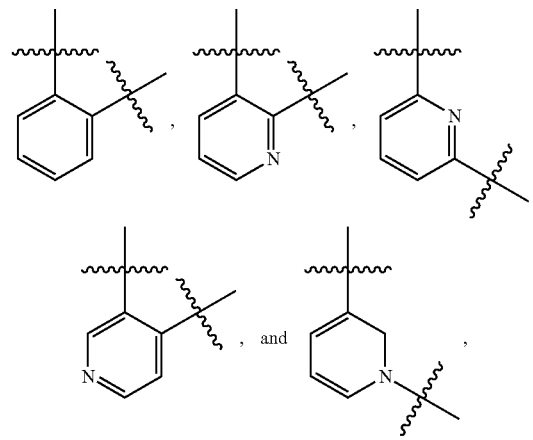

each of which is optionally substituted with one or more substituents independently selected from the group consisting of fluoro and

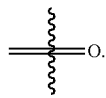

In some more typical embodiments, Cy is selected from the group consisting of

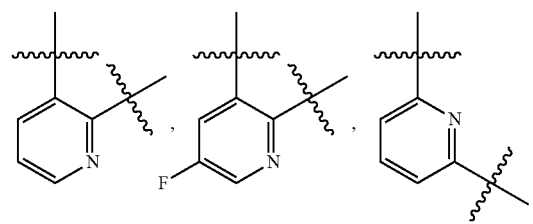

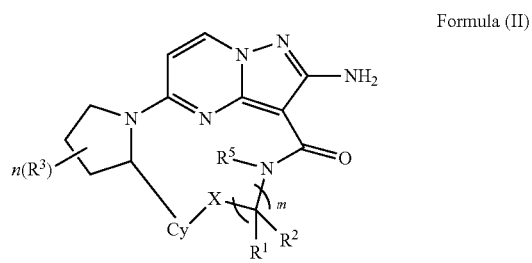

In some embodiments of the present application, the aforementioned compound of Formula (I) is selected from a compound of Formula (II),

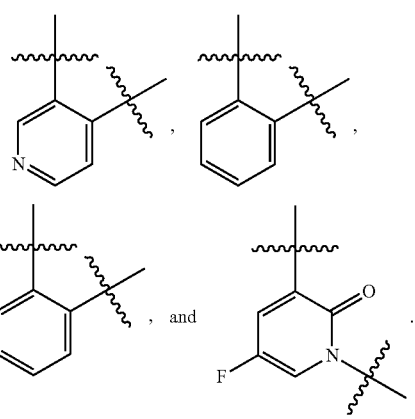

Formula (II)

Wherein X, $R^1$, $R^2$, $R^3$, $R^5$, Cy, m and n are as defined in the aforementioned compound of Formula (I).

In some embodiments of the present application, the aforementioned compound of Formula (I) or a pharmaceutically acceptable salt thereof is selected from the group consisting of

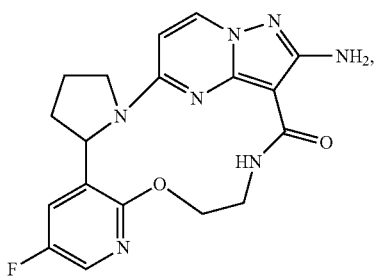

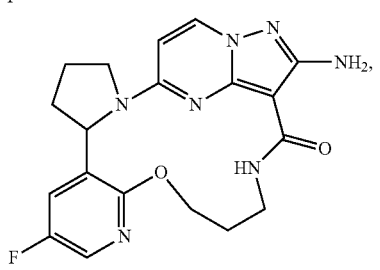

-continued
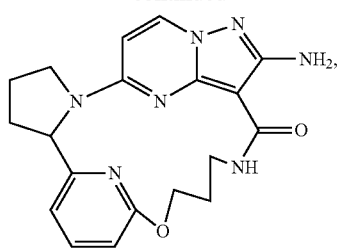
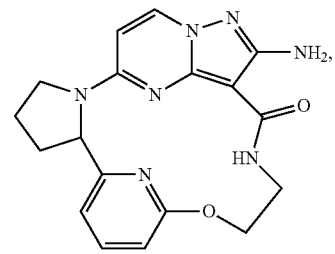
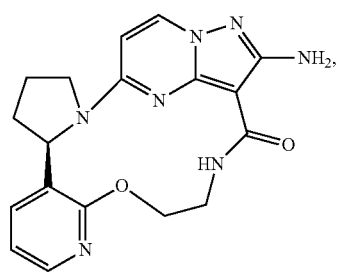
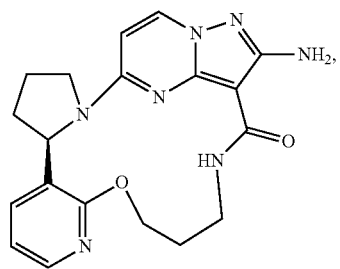
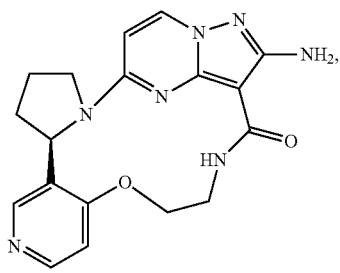
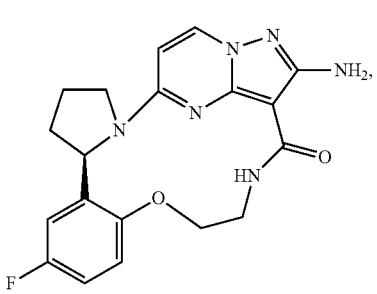
-continued
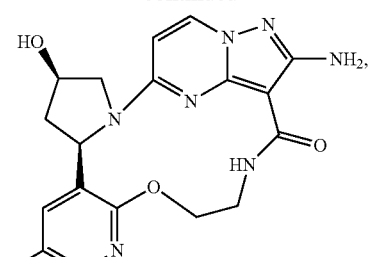
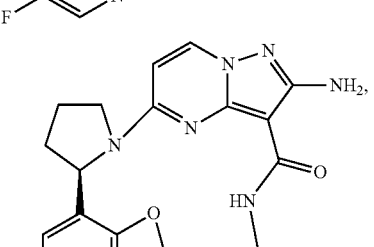
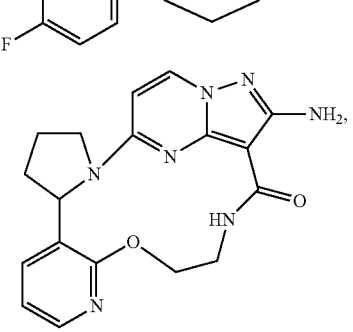
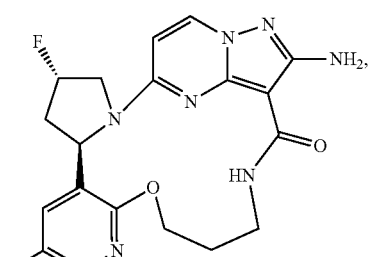
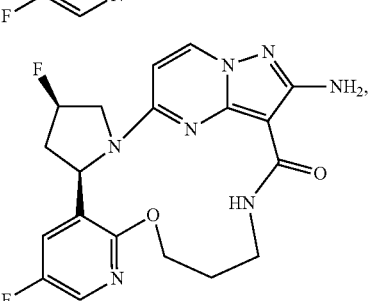
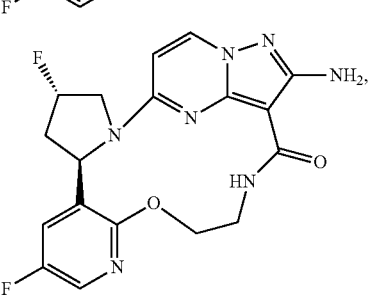

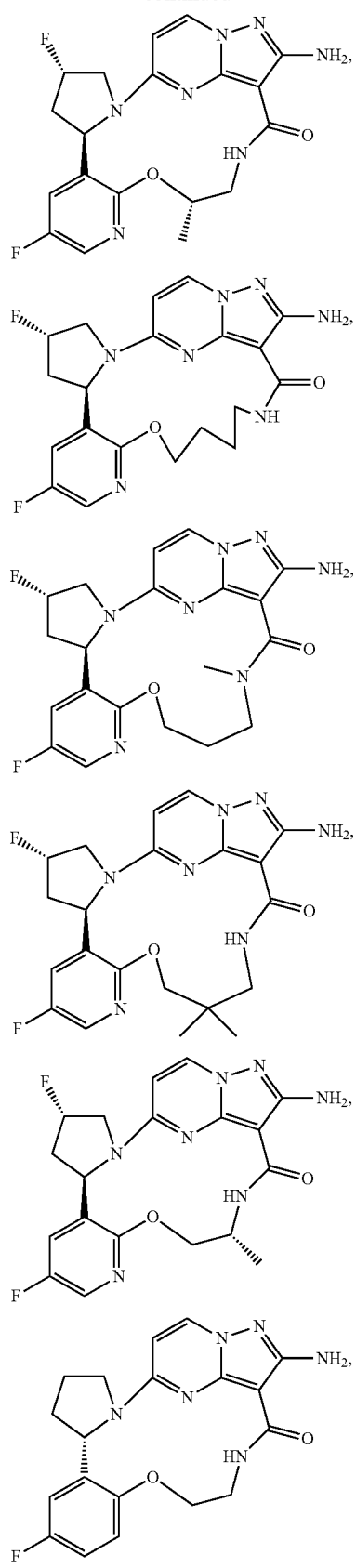
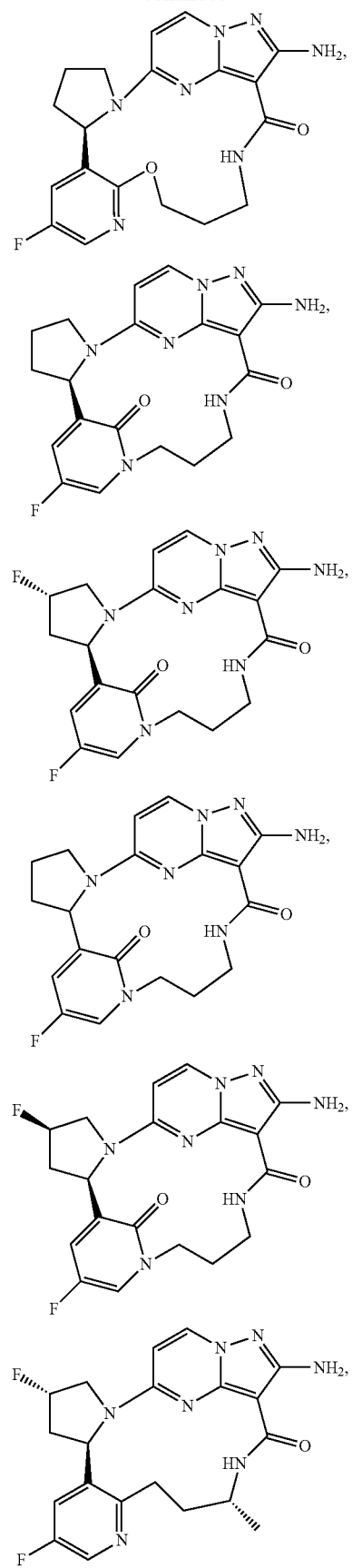

-continued

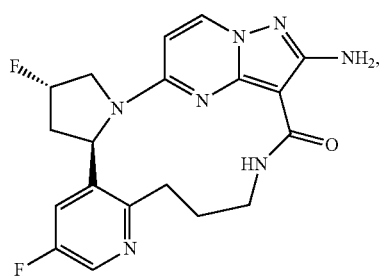

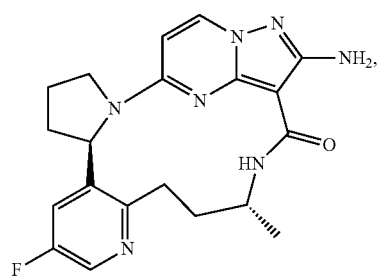

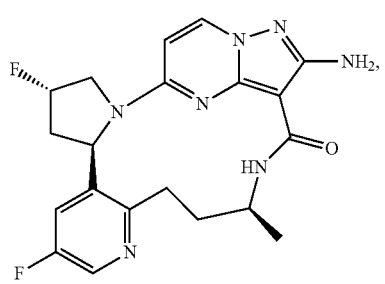

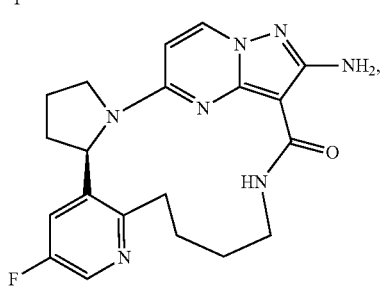

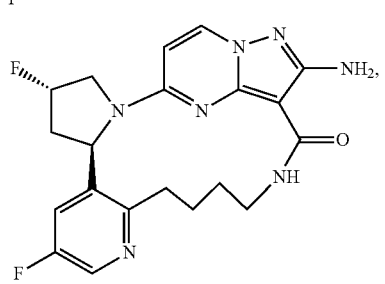

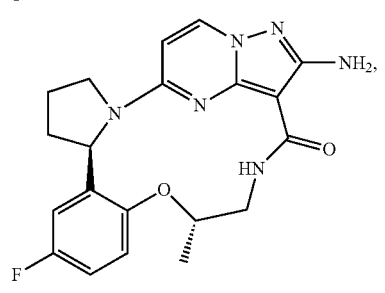

-continued

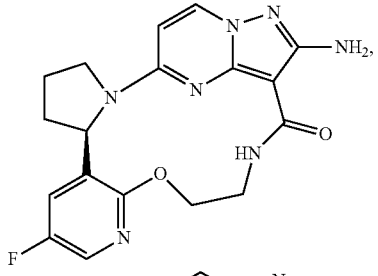

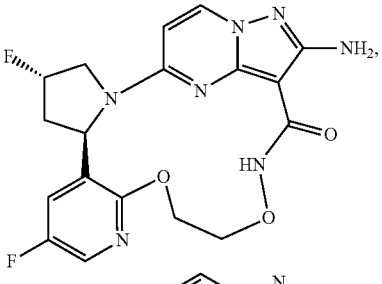

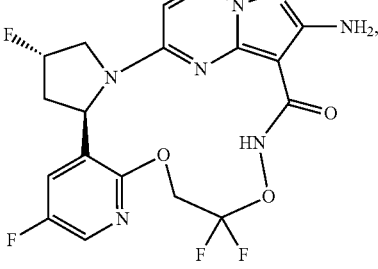

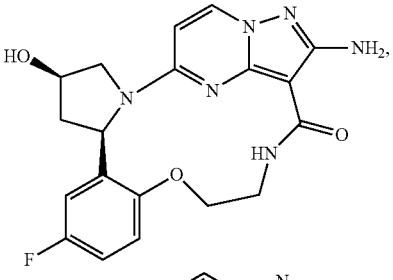

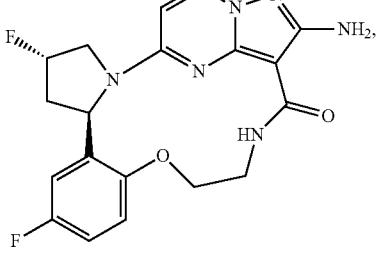

and a pharmaceutically acceptable salt thereof.

In another aspect, the present application relates to a pharmaceutical composition comprising the compound of Formula (I) of the present application, or a pharmaceutically acceptable salt thereof. In some embodiments, the pharmaceutical composition according to the present application further comprises a pharmaceutically acceptable excipient.

The pharmaceutical composition according to the present application may be prepared by combining the compound of Formula (I) according to the present application with appropriate pharmaceutically acceptable excipient(s). For example, the pharmaceutical compositions of the present application may be formulated into solid, semi-solid, liquid or gaseous formulations, such as tablets, pills, capsules, powders, granules, ointments, emulsions, suspensions, suppositories, injections, inhalants, gels, microspheres, aerosols, and the like.

Typical administration routes of the compound of Formula (I) according to the present application or a pharmaceutically acceptable salt thereof, or the pharmaceutical composition thereof include, but are not limited to, oral, rectal, topical, inhalation, parenteral, sublingual, intravaginal, intranasal, intraocular, intraperitoneal, intramuscular, subcutaneous, and intravenous administration.

The pharmaceutical compositions of the present application can be prepared by using well-known methods in the art, such as conventional mixing method, dissolution method, granulation method, dragee manufacture method, grinding method, emulsification method, freeze-drying method, and the like.

In some embodiments, the pharmaceutical composition is in oral form. For oral administration, the pharmaceutical composition may be formulated by mixing the active compound(s) with pharmaceutically acceptable excipient(s) well-known in the art. Such excipients enable the compounds of Formula (I) of the present application to be formulated into tablets, pills, lozenges, dragees, capsules, liquids, gels, syrups, suspensions and the like, for oral administration to patients.

A solid oral pharmaceutical composition can be prepared by a conventional mixing, filling or tabletting method. For example, it can be obtained by mixing the active compound with a solid excipient, optionally grinding the resulting mixture, adding other suitable excipients, if necessary, and then processing the mixture into granules to obtain cores of tablets or dragees. Suitable excipients include, but are not limited to, binders, diluents, disintegrants, lubricants, glidants, sweeting agents, flavoring agents, and the like.

The pharmaceutical composition is also suitable for parenteral administration, such as sterile solutions, suspensions or lyophilized products in a suitable unit dosage form.

In a further aspect, the present application relates to a method for treating a disease mediated by Trk kinase in a mammal, comprising administering to the mammal in need thereof, preferably a human, a therapeutically effective amount of the compound of Formula (I) or a pharmaceutically acceptable salt thereof, or a pharmaceutical composition thereof.

A daily dose of the compound of Formula (I) in all the administration manners as described herein is from 0.01 mg/kg body weight to 300 mg/kg body weight, preferably from 10 mg/kg body weight to 300 mg/kg body weight, and more preferably from 25 mg/kg body weight to 200 mg/kg body weight, in the form of a single dose or a divided dose.

In another aspect, the present application relates to a use of the compound of Formula (I) or a pharmaceutically acceptable salt thereof, or a pharmaceutical composition thereof in the preparation of a medicament for the prophylaxis or treatment of a disease mediated by Trk kinase.

In still another aspect, the present application relates to a use of the compound of Formula (I) or a pharmaceutically acceptable salt thereof, or a pharmaceutical composition thereof in the prophylaxis or treatment of a disease mediated by Trk kinase.

In a further aspect, the present application provides the compound of Formula (I) or a pharmaceutically acceptable salt thereof, or a pharmaceutical composition thereof for use in the prophylaxis or treatment of a disease mediated by Trk kinase.

The compounds of the present application can be prepared through various synthetic methods well-known to a person skilled in the art, including specific embodiments illustrated below, embodiments obtained by combining such specific embodiments with other chemical synthetic methods, and equivalents well-known to a person skilled in the art. Preferred embodiments include, but are not limited to, the working Examples in the present application.

A chemical reaction in the specific embodiments of the present application is carried out in an appropriate solvent which should be suitable for the chemical change(s) and the required reagent(s) and material(s) in the present application. In order to obtain the compounds of the present application, it is sometimes necessary for a person skilled in the art to make a modification or selection to synthesis step(s) or reaction scheme(s) on the basis of the existing embodiments.

An important consideration in the design of a synthetic route in the art is the selection of a suitable protecting group for a reactive functional group, such as an amino group in the present application. For example, reference may be made to Greene's Protective Groups in Organic Synthesis (4th Ed). Hoboken, N.J.: John Wiley & Sons, Inc. All references cited herein are incorporated herein in their entireties.

In some embodiments, the compound of Formula (II) of the present application may be prepared by a person skilled in the field of organic synthesis using a standard method through the following exemplary synthetic schemes including, but not limited to:

Synthetic Scheme I

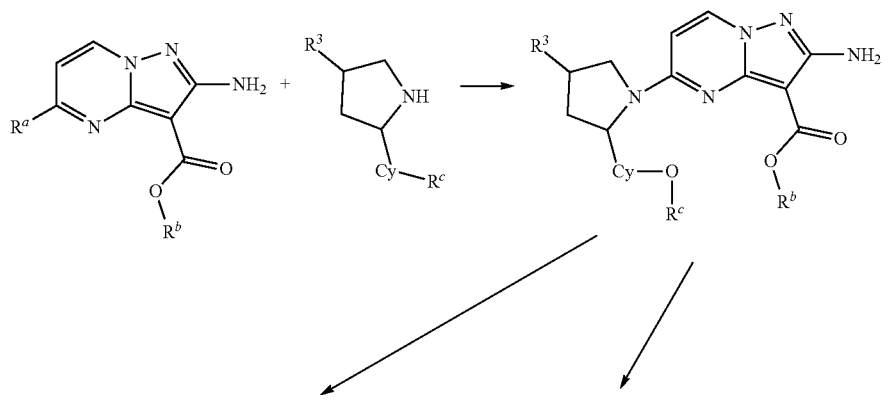

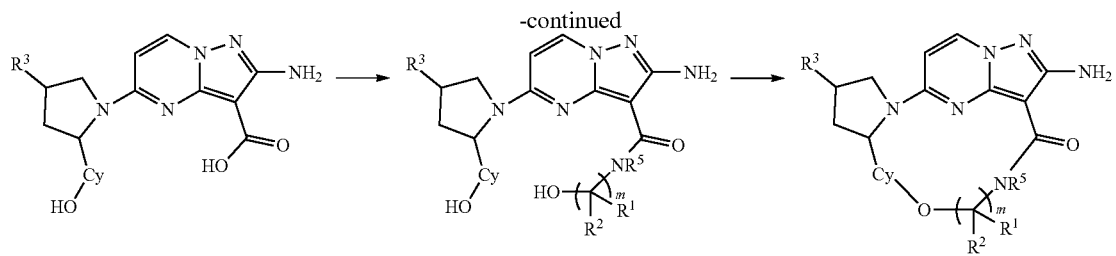

Wherein R$^a$ is selected from halo, preferably fluoro, chloro, bromo, or iodo;

R$^b$ is selected from C$_1$-C$_6$ alkyl, preferably C$_1$-C$_3$ alkyl, and further preferably ethyl;

R$^c$ is selected from C$_1$-C$_6$ alkyl, preferably C$_1$-C$_3$ alkyl, and further preferably methyl;

R$^1$, R$^2$, R$^3$, R$^5$, Cy and m are as defined in the aforementioned compound of Formula (II).

Synthetic Scheme II

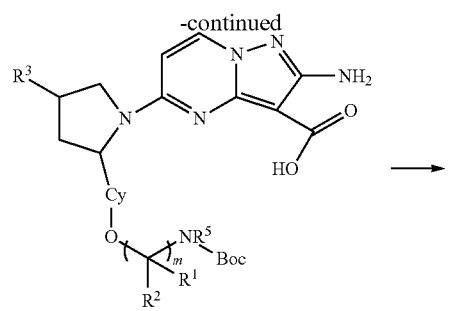

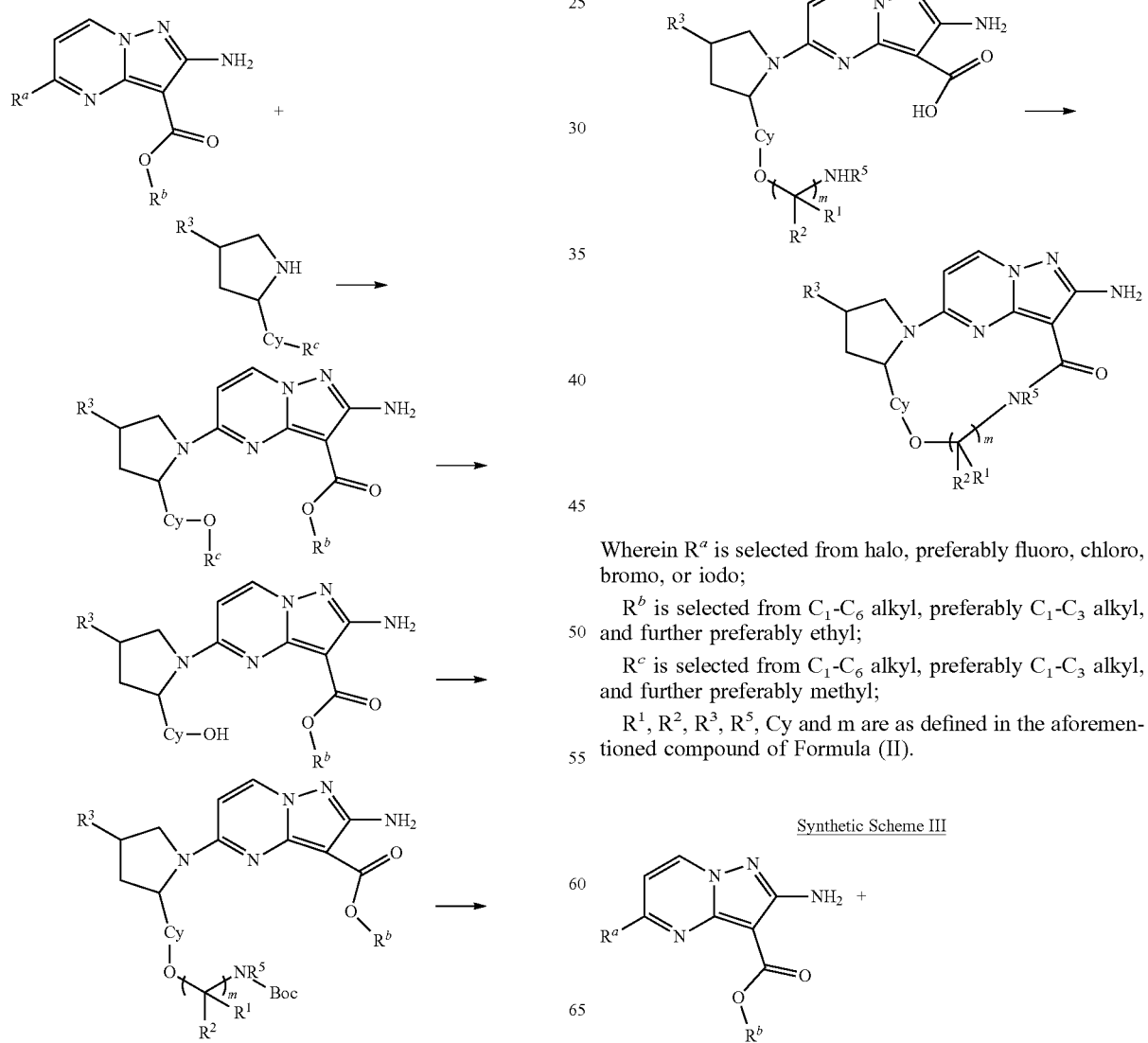

Wherein R$^a$ is selected from halo, preferably fluoro, chloro, bromo, or iodo;

R$^b$ is selected from C$_1$-C$_6$ alkyl, preferably C$_1$-C$_3$ alkyl, and further preferably ethyl;

R$^c$ is selected from C$_1$-C$_6$ alkyl, preferably C$_1$-C$_3$ alkyl, and further preferably methyl;

R$^1$, R$^2$, R$^3$, R$^5$, Cy and m are as defined in the aforementioned compound of Formula (II).

Synthetic Scheme III

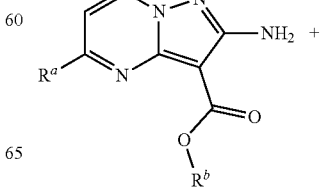

-continued

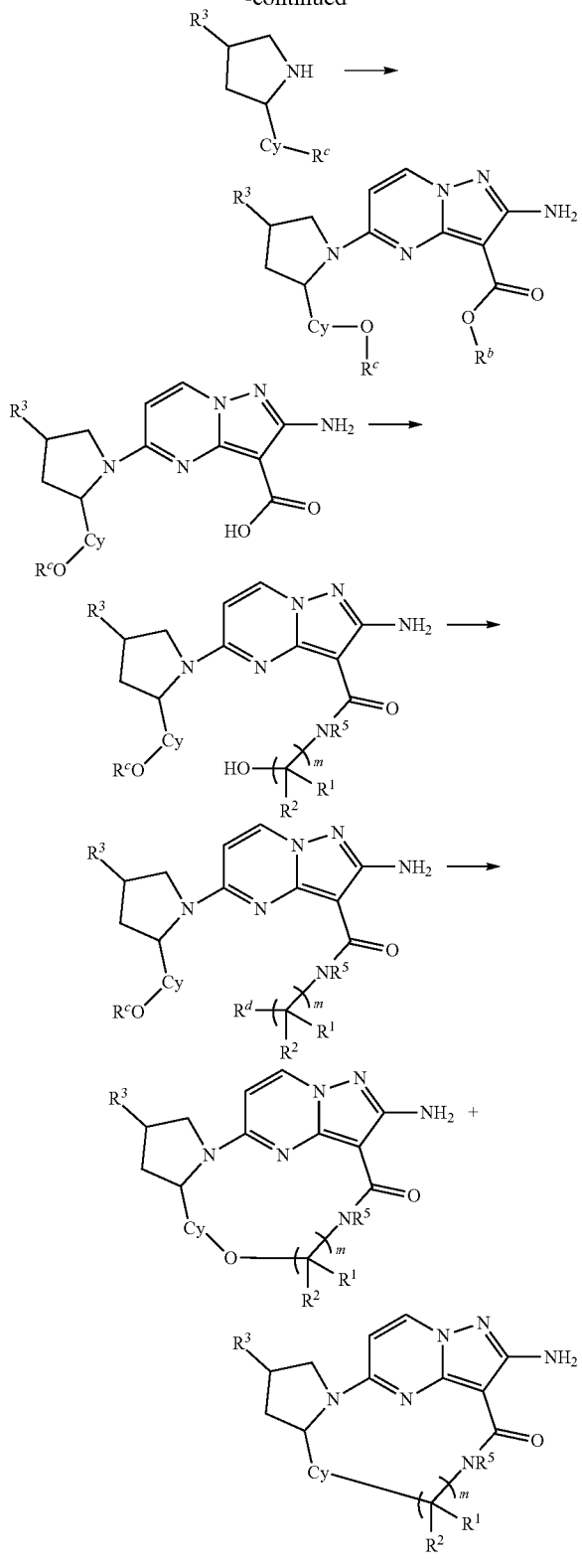

Wherein $R^a$ is selected from halo, preferably fluoro, chloro, bromo, or iodo;

$R^b$ is selected from $C_1$-$C_6$ alkyl, preferably $C_1$-$C_3$ alkyl, and further preferably ethyl;

$R^c$ is selected from $C_1$-$C_6$ alkyl, preferably $C_1$-$C_3$ alkyl, and further preferably methyl;

$R^d$ is selected from halo, preferably fluoro, chloro, bromo, or iodo;

$R^1$, $R^2$, $R^3$, $R^5$, Cy and m are as defined in the aforementioned compound of Formula (II).

Synthetic Scheme IV

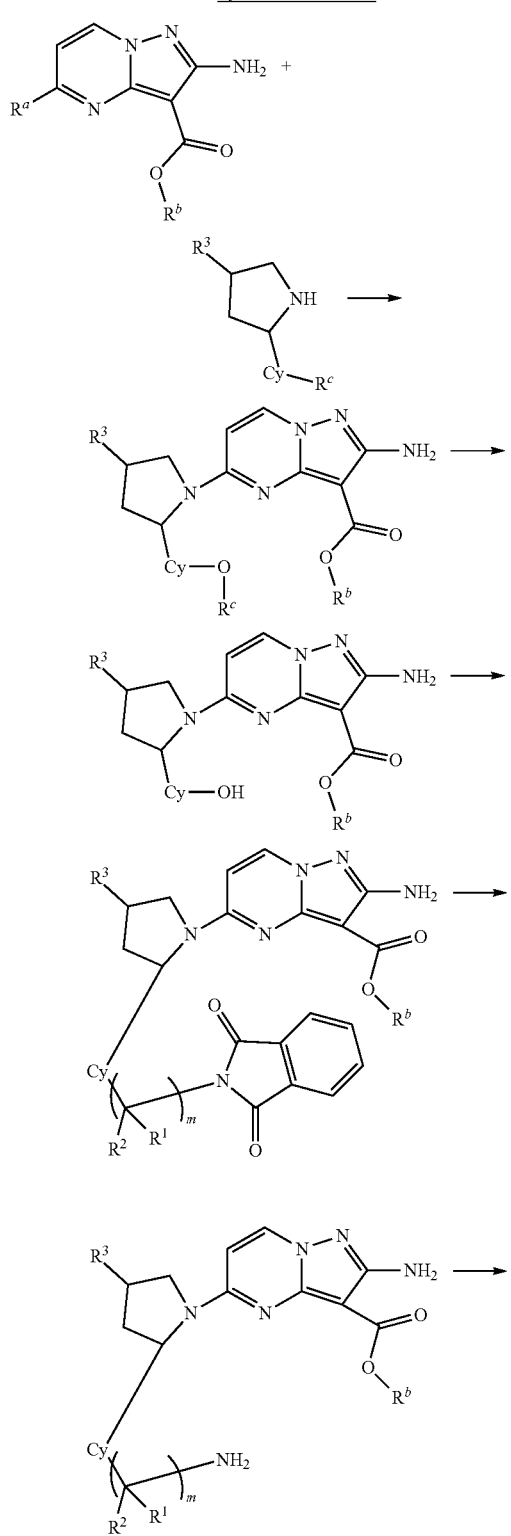

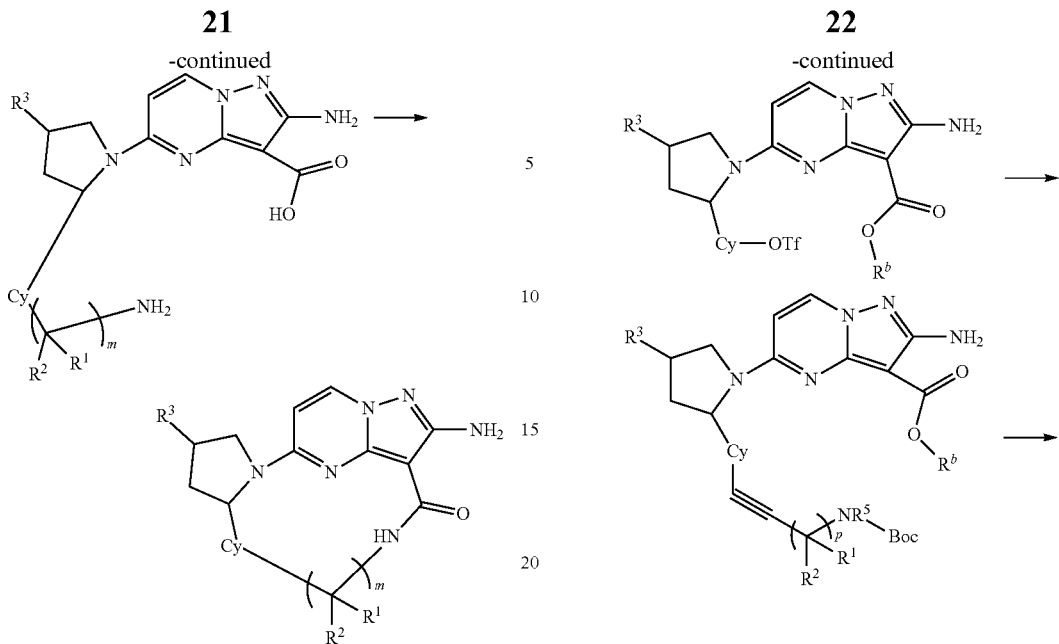

Wherein, $R^a$ is selected from halo, preferably fluoro, chloro, bromo, or iodo;

$R^b$ is selected from $C_1$-$C_6$ alkyl, preferably $C_1$-$C_3$ alkyl, and further preferably ethyl;

$R^c$ is selected from $C_1$-$C_6$ alkyl, preferably $C_1$-$C_3$ alkyl, and further preferably methyl;

$R^1$, $R^2$, $R^3$, Cy and m are as defined in the aforementioned compound of Formula (II).

Synthetic Scheme V

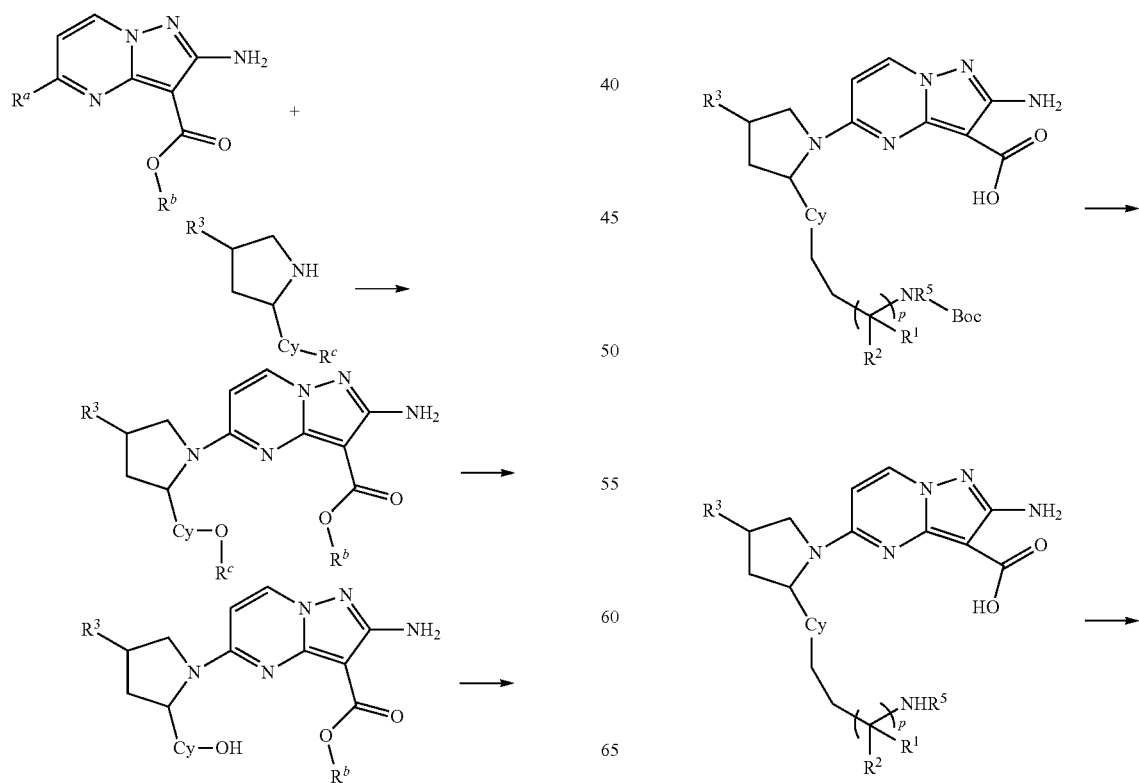

-continued

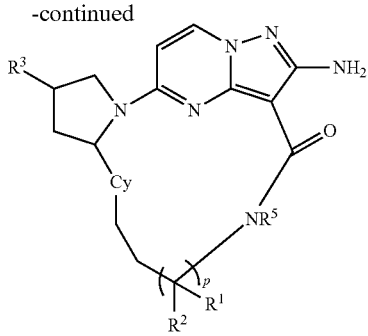

Wherein $R^a$ is selected from halo, preferably fluoro, chloro, bromo, or iodo;

$R^b$ is selected from $C_1$-$C_6$ alkyl, preferably $C_1$-$C_3$ alkyl, and further preferably ethyl;

$R^c$ is selected from $C_1$-$C_6$ alkyl, preferably $C_1$-$C_3$ alkyl, and further preferably methyl;

P is selected from 0, 1, 2, 3, or 4.

$R^1$, $R^2$, $R^3$, $R^5$, and Cy are as defined in the aforementioned compound of Formula (II).

Definition

Unless stated otherwise, the following terms used herein have the following meanings. A specific term shall not be considered unclear or indefinite when it is not specially defined. It should be understood according to its general meaning. A trade name used herein refers to a corresponding product or an active ingredient thereof.

The term "substituted" means that one or more hydrogen atoms on a given atom are replaced with a substituent, provided that the given atom has a normal valence state and the compound after substitution is stable. When the substituent is an oxo (i.e., =O), which means that two hydrogen atoms are replaced, the oxo substitution will not occur on an aromatic group.

The term "optional" or "optionally" means that the subsequently described event or circumstance may or may not occur, and that the description includes instances where said event or circumstance occurs and instances where said event or circumstance does not occurs. For example, ethyl group is "optionally" substituted with halogen atom(s), which means that ethyl group may be unsubstituted ($CH_2CH_3$), mono-substituted (such as $CH_2CH_2F$), multiple-substituted (such as $CHFCH_2F$, $CH_2CHF_2$, and so on) or fully substituted ($CF_2CF_3$). A person skilled in the art will understand that in respect to any group containing one or more substituents, any substitution or substitution mode that is spatially impossible and/or not synthesizable will not be introduced.

The expression $C_m$-$C_n$ as used herein indicates that this moiety has an integer number of carbon atoms within a given range. For example, "$C_1$-$C_6$" means that this group may have 1 carbon atom, 2 carbon atoms, 3 carbon atoms, 4 carbon atoms, 5 carbon atoms or 6 carbon atoms.

When any variable (such as R) occurs more than one times at the composition or structure of a compound, the variable is defined independently at each occurrence. Therefore, for example, if a group is substituted with two Rs, then each R has an independent option. As another example, when m≥2 in the structural unit

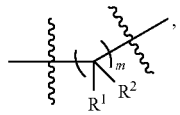

both $R^1$ and $R^2$ in each repeating unit have an independent option. For another example, when n≥2 in the structural unit

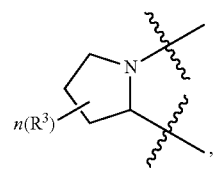

each $R^3$ has an independent option.

X is a bond, which means that X in the compound of Formula (I) is absent. That is, the Cy group in the compound of Formula (I) is linked to the structural unit

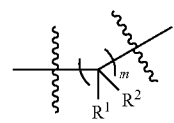

directly through a covalent bond.

The term "halo" or "halogen" refers to fluoro, chloro, bromo and iodo.

The term "hydroxy" refers to —OH group.

The term "cyano" refers to —CN group.

The term "amino" refers to —$NH_2$ group.

The term "nitro" refers to —$NO_2$ group.

The term "alkyl" refers to a hydrocarbyl group of Formula $C_nH_{2n+1}$. The alkyl group can be straight or branched. For example, the term "$C_1$-$C_6$ alkyl" refers to an alkyl group having 1 to 6 carbon atoms (such as methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). Similarly, the alkyl moiety (i.e., alkyl) in an alkoxy group, an alkylamino group, a dialkylamino group, an alkylsulfonyl group, and an alkylthio group has the same definition as defined above.

The term "alkoxy" refers to —O-alkyl.

The term "cycloalkyl ring" refers to a carbon ring that is fully saturated and can exist in the form of a monocyclic ring, bridged ring or spirocyclic ring. Unless otherwise indicated, the carbocycle is typically a 3- to 10-membered ring. Non-limiting examples of cycloalkyl ring include, but are not limited to, cyclopropane, cyclobutane, cyclopentane, cyclohexane, bicyclo[2.2.2]octane, adamantane, etc.

The term "aliphatic heterocycle" refers to a fully saturated or partially unsaturated (but not fully unsaturated heteroaromatic) non-aromatic ring that can be exist in the form of a monocyclic ring, bicyclic ring or spirocyclic ring. Unless otherwise indicated, the heterocycle is typically a 3- to 6-membered ring containing 1 to 3 heteroatoms (preferably 1 or 2 heteroatoms) independently selected from sulfur, oxygen, and/or nitrogen.

Non-limiting examples of aliphatic heterocycle include, but are not limited to oxirane, tetrahydrofuran, dihydrofuran, pyrrolidine, N-methylpyrrolidine, dihydropyrrole, piperidine, piperazine, pyrazolidine, 4H-pyran, morpholine, thiomorpholine, tetrahydrothiophene, etc.

The term "aromatic heterocycle" refers to a monocyclic or fused polycyclic system containing at least one ring atom selected from N, O, and S with remaining ring atoms being C, and having at least one aromatic ring. Preferred aromatic heterocycle has a single 4- to 8-membered ring, especially a single 5- to 8-membered ring, or has a fused polycyclic ring containing 6 to 14, especially 6 to 10 rings atoms. Non-limiting examples of aromatic heterocycle include, but are not limited to, pyrrole, furan, thiophene, imidazole, oxazole, pyrazole, pyridine, pyrimidine, pyrazine, quinoline, isoquinoline, benzofuran, benzothiophene, indole, isoindole, etc.

The term "treatment" or "treating" refers to the administration of the compounds or preparations of the present application for preventing, ameliorating or eliminating diseases or one or more symptoms associated with the diseases, comprising:

(i) prophylaxis of occurrence of diseases or conditions in mammals, particularly when the mammals are susceptible to the conditions, but have not been diagnosed with them;

(ii) inhibition of diseases or conditions, i.e. restraining their development; or (iii) relief of diseases or conditions, i.e. recovering from the diseases or conditions.

The term "therapeutically effective amount" means an amount of a compound of the present application that (i) treats or prevents a particular disease, condition, or disorder, (ii) attenuates, ameliorates, or eliminates one or more symptoms of a particular disease, condition, or disorder, or (iii) prevents or retards the onset of one or more symptoms of a particular disease, condition, or disorder as described herein. The amount of the compounds of the present application constituting so-called "therapeutically effective amount" depends on the compound, disease condition and severity thereof, the way of administration and age of the mammal to be treated, but can be routinely determined by those skilled in the art on the basis of their knowledge and the disclosure herein.

The term "pharmaceutically acceptable" refers to a compound, material, composition and/or dosage form that is applicable to the contact with human and animal tissues without an excessive toxicity, irritation, allergic reaction or other problems or complications in the scope of reliable medical judgment, and is commensurate with an acceptable benefits/risk ratio.

As a pharmaceutically acceptable salt, for example, a metal salt, an ammonium salt, a salt formed with an organic base, a salt formed with an inorganic acid, a salt formed with an organic acid, a salt formed with a basic or acidic amino acid, etc. can be mentioned.

The term "pharmaceutical composition" refers to a mixture of one or more compounds of the present application or a salt thereof and a pharmaceutically acceptable excipient. The purpose of pharmaceutical composition is to facilitate the administration of the compounds of the present application to the organism.

The term "pharmaceutical acceptable excipient" refers to those excipients which do not cause significant stimulation to an organism, and will not impair the bioactivity and properties of an active compound. Suitable excipients are well known to those skilled in the art, such as carbohydrates, waxes, water-soluble and/or water-swellable polymers, hydrophilic or hydrophobic materials, gelatin, oils, solvents, water, and the like.

The phrase "comprise" and English variations thereof, such as "comprises" and "comprising", should be construed in an open and inclusive sense, that is as, "including, but not limited to."

Unless particularly defined otherwise, the abbreviations used herein have the following meanings.

min refers to minute;
h refers to hour;
50° C. refers to Celsius degree;
V:V refers to a volume ratio;
DCM refers to dichloromethane;
$AC_2O$ refers to acetic anhydride;
EA refers to ethyl acetate;
PE refers to petroleum ether;
MeOH refers to methanol;
THF refers to tetrahydrofuran;
ACN refers to acetonitrile;
Toluene refers to methylbenzene;
DMF refers to N,N-dimethylformamide;
DMSO refers to dimethylsulphoxide;
TEA refers to triethylamine;
EDCI refers to 1-(3-dimethylaminopropyl)-3-ethylcarbodiimide hydrochloride;
HOBT refers to 1-hydroxybenzotriazole;
$Ti(OEt)_4$ refers to tetraethyl titanate;
DMAP refers to 4-dimethylaminopyridine;
DIAD refers to diisopropyl azodicarboxylate;
$PPh_3$ refers to triphenylphosphine;
$PD(PPh_3)_4$ refers to tetrakis(triphenylphosphine)palladium;
$PdCl_2$ refers to palladium chloride;
CuI refers to cuprous iodide;
TFA refers to trifluoroacetic acid;
TBDMSCl refers to tert-butyldimethylchlorosilane;
$NaBH_4$ refers to sodium borohydride;
LiHMDS refers to lithium hexamethyldisilazide;
$(BOC)_2O$ refers to ditert-butyl dicarbonate;
NBS refers to N-bromosuccinimide;
Dess-Martin refers to Dess-Martin periodinane;
DAST refers to diethylaminosulfur trifluoride;
HATU refers to O-(7-azabenzotriazol-1-yl)-N,N,N',N'-tetramethyluronium hexafluorophosphate;
DIEA refers to N,N-diisopropylethylamine;
FDPP refers to pentafluorophenyl diphenylphosphate;
LC-MS refers to liquid chromatography-mass spectrometry;
HMPA refers to hexamethylphosphoric triamide;
$Cs_2CO_3$ refers to cesium carbonate;
LiH refers to lithium hydride;
TLC refers to thin layer chromatography;
M refers to molar concentration unit mol/L, for example, 2M referring to 2 mol/L;
mM refers to molar concentration unit millimole per liter, e.g., 2 mM referring to 2 mmol/L;
N refers to an equivalent concentration, for example, 1N HCl refers to hydrochloric acid with a concentration of 1 mol/L; 2N NaOH refers to sodium hydroxide with a concentration of 2 mol/L;
Ts refers to p-methylbenzenesulfonyl;
TsCl refers to p-toluenesulfonyl chloride;
Et refers to ethyl;
Me refers to methyl;
Ac refers to acetyl;
PMB refers to p-methoxybenzyl;
Boc refers to tert-butoxycarbonyl;
TBS refers to tert-butyldimethylsilyl.

The intermediates and compounds according to the present application may also exist in the form of different tautomers, and all such forms are included in the scope of the present application. The term "tautomer" or "tautomeric form" refers to structural isomers with different energies which are interconvertible via a low energy barrier. For example, proton tautomers (also known as prototropic tautomers) include interconversions via migration of a proton, such as keto-enol and imine-enamine isomerizations. A specific example of proton tautomers is an imidazole moiety, in which a proton can migrate between the two ring nitrogen atoms. Valence tautomers include interconversions by reorganization of some of the bonding electrons. Non-limiting examples of tautomers include, but are not limited thereto,

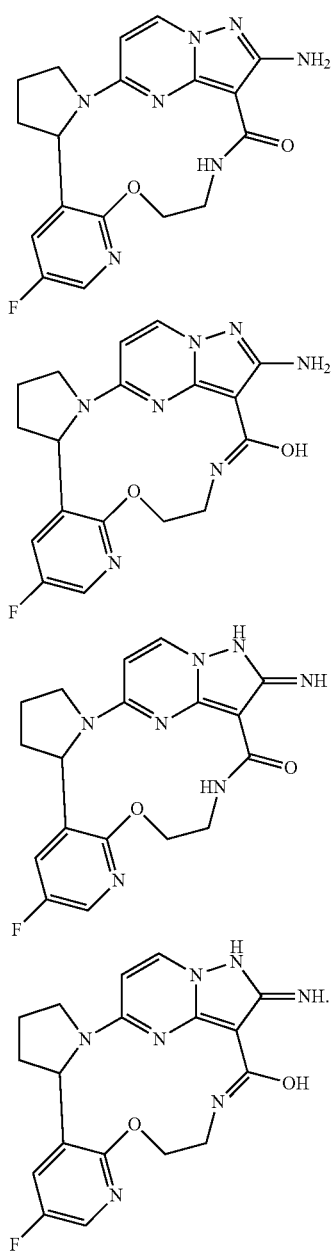

The compounds of the present application also include isotopically-labeled compounds of the present application which are identical to those recited herein, but for the fact that one or more atoms are replaced by an atom having an atomic mass or mass number different from the atomic mass or mass number usually found in nature. Examples of isotopes that can be incorporated into the compounds of the present application include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the present application (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Positron emitting isotopes such as $^{15}$O, $^{13}$N, $^{11}$C, and $^{18}$F are useful for positron emission tomography (PET) studies to examine substrate occupancy. Isotopically labeled compounds of the present application can generally be prepared by the following procedures analogous to those disclosed in the Schemes and/or Examples herein below, by substituting an isotopically labeled reagent for a non-isotopically labeled reagent.

Further, substitution with heavier isotopes (such as deuterium, i.e. $^2$H) may afford certain therapeutic advantages resulting from greater metabolic stability, for example, increasing in vivo half-life or reducing dosage requirements, and hence may be preferred in some circumstances, in which the deuteration may be partial or complete, and partial deuteration means that at least one hydrogen is replaced with at least one deuterium. Non-limiting examples of deuterated compounds include, but are not limited thereto,

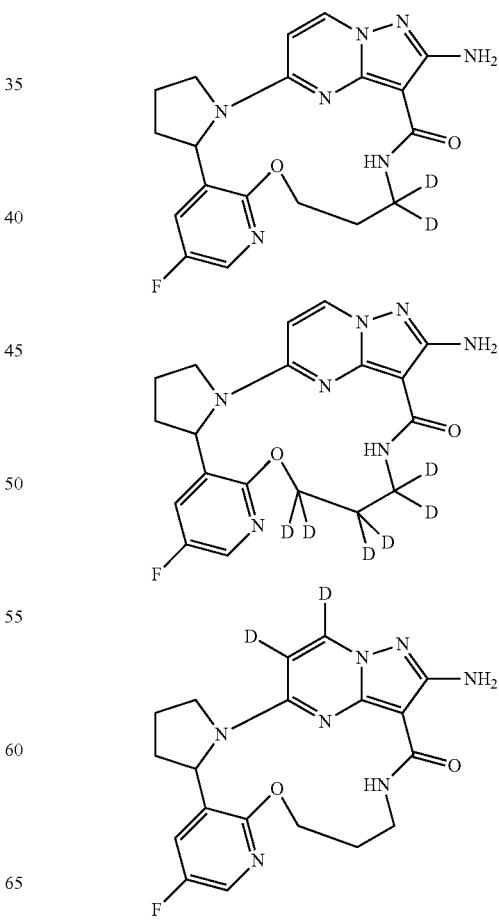

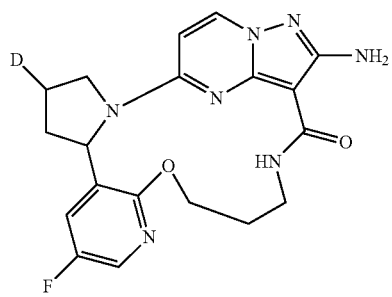

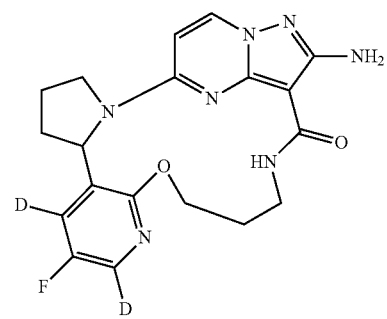

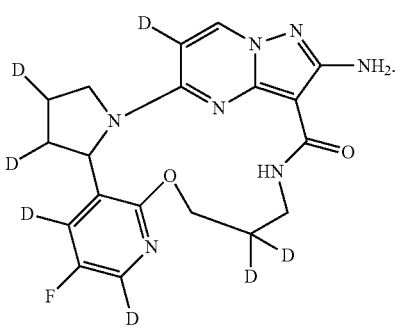 [SMILES: [2H]c1cn2nc(N)c3c2nc1N1CC([2H])C([2H])C1c1c(nc([2H])c(F)c1[2H])OCC([2H])([2H])CNC3=O]

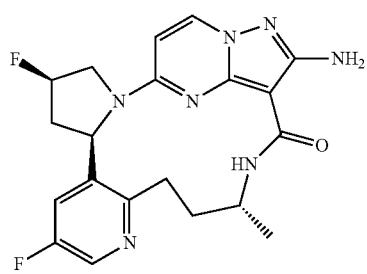

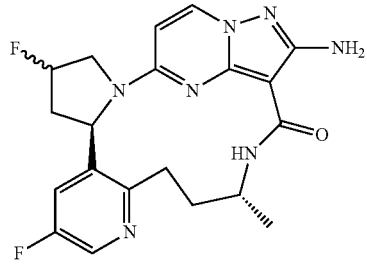

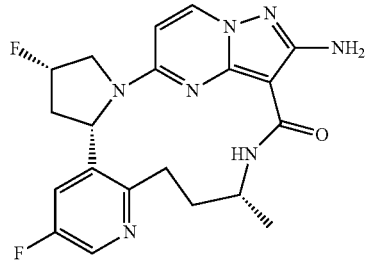

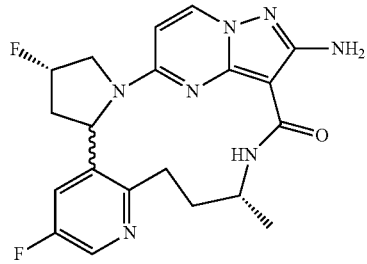

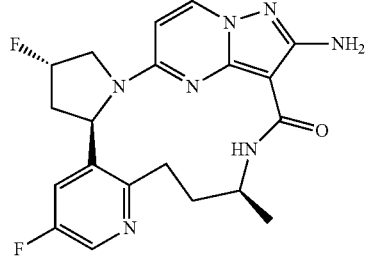

The compounds of the present application may be asymmetric, for example, having one or more stereoisomers. Unless otherwise indicated, all stereoisomers, such as enantiomers and diastereomers, are included therein. Compounds containing asymmetric carbon atom(s) of the present application can be isolated in an optically active pure form or a racemic form. The optically active pure form can be resolved from a racemic mixture, or synthesized by using chiral raw material(s) or chiral reagent(s). Non-limiting examples of stereoisomers include, but are not limited to,

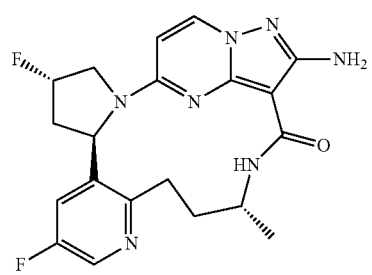

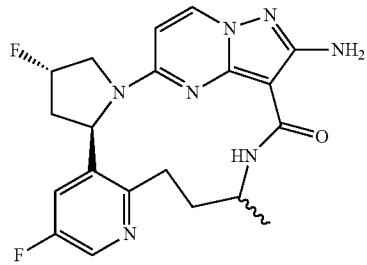

-continued
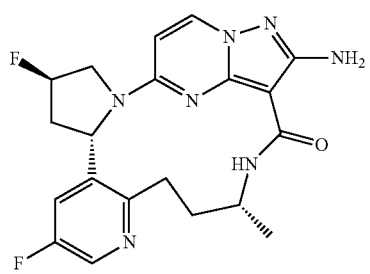
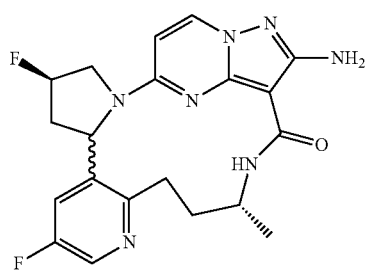
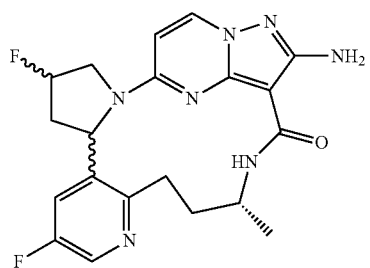
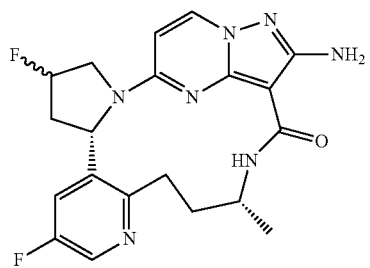
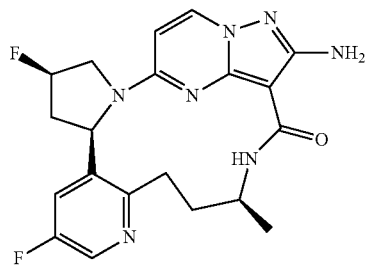
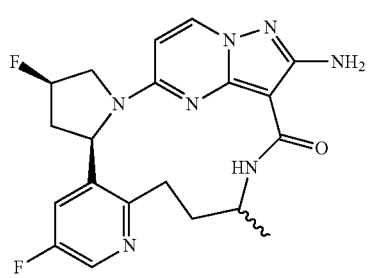
-continued
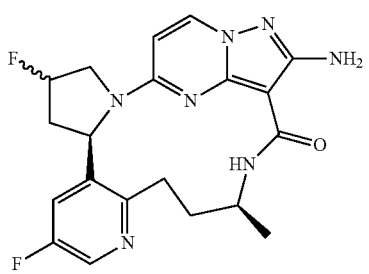
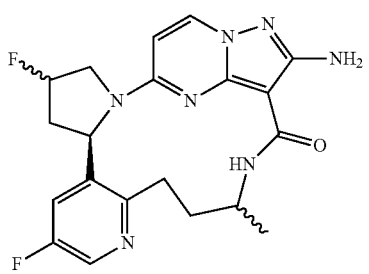
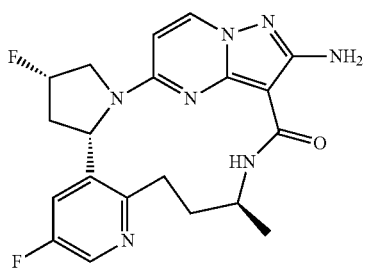
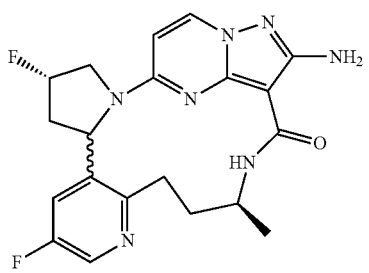
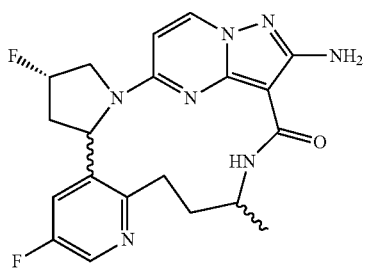
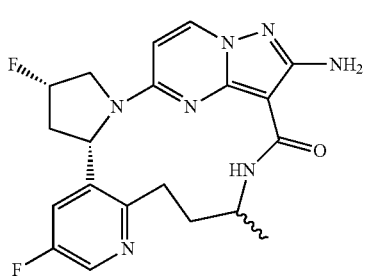

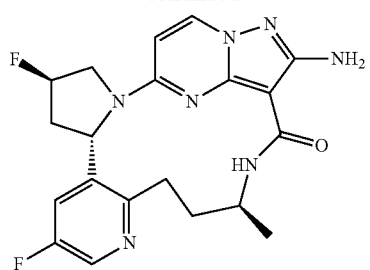
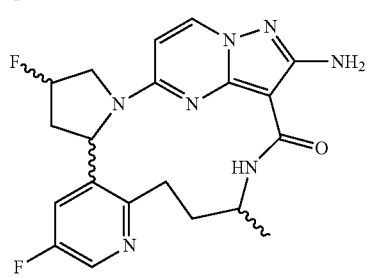
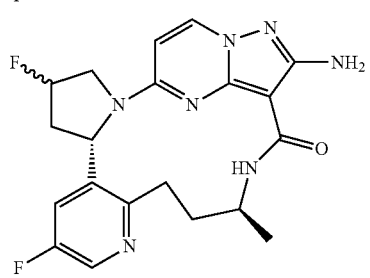
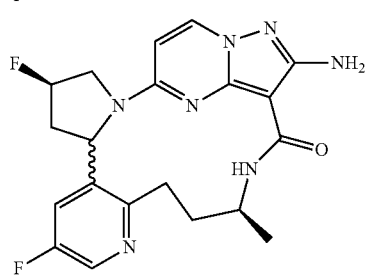
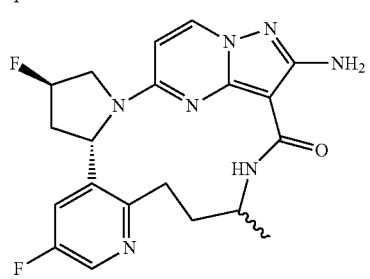
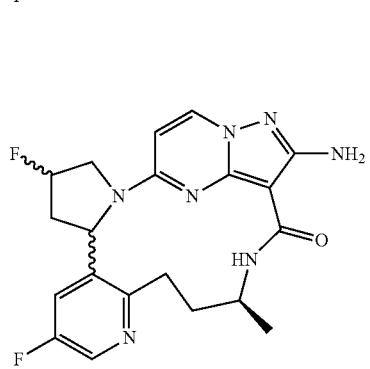

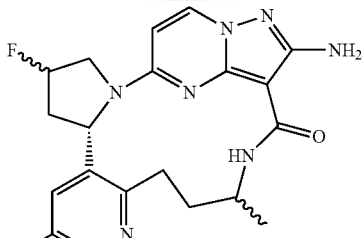
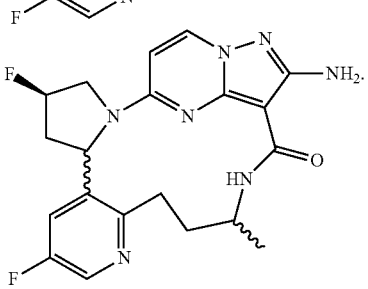

For clarity, the present invention is further illustrated by the following examples, but the examples are not intended to limit the scope of the present application. All reagents used in the present application are commercially available and can be used without further purification.

SPECIFIC EXAMPLES

Preparation of Intermediates

Intermediate 1: Synthesis of 5-fluoro-2-methoxy-3-(pyrrolidin-2-yl)pyridine

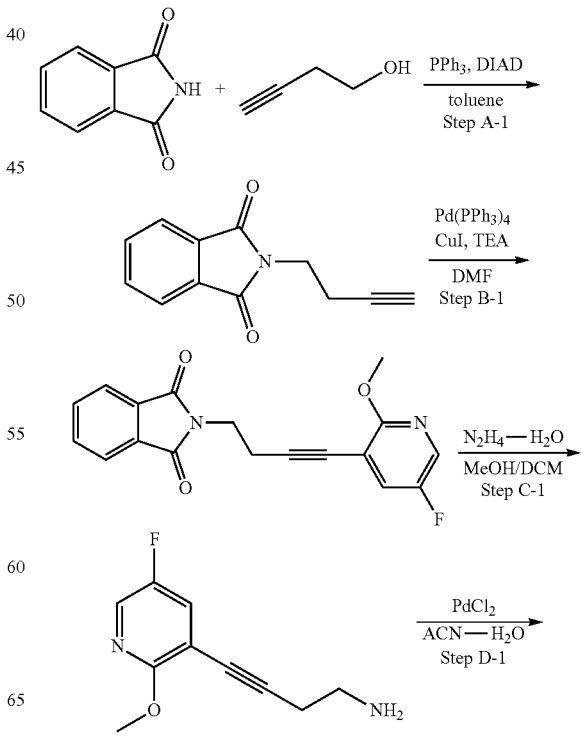

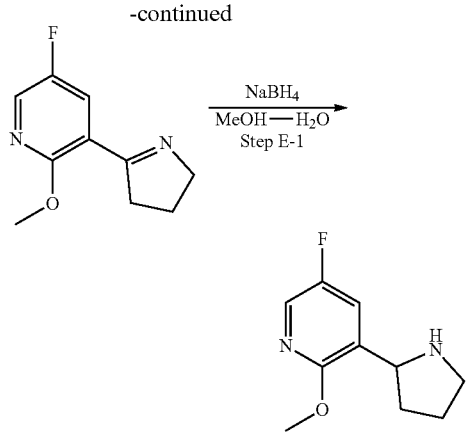

Step A-1: Synthesis of 2-(3-butyn-1-yl)isoindole-1,3-dione

To a mixture solution of phthalimide (20.0 g), 3-butyn-1-ol (10.5 g) and triphenylphosphine (39.3 g) in toluene (200 mL) was slowly added DIAD (34.0 g) dropwise at 0° C. After completion of the addition, the resulting mixture was warmed to room temperature and continuously stirred for 1 h. To the reaction mixture was added methanol (50 mL) and stirred for 1 h. A large amount of white solid was precipitated out, and then filtered. The filter cake was washed with methanol to afford the title compound (15.6 g). The filtrate was concentrated, and the residue was slurried with methanol and then filtered to afford the title compound (7.95 g).
$^1$H NMR (400 MHz, CDCl$_3$) δ 7.88-7.81 (m, 4H), 3.69 (t, J=6.8 Hz, 2H), 3.80 (t, J=2.8 Hz, 1H), 2.55-2.51 (m, 2H).

Step B-1: Synthesis of 2-(4-(5-fluoro-2-methoxypyridin-3-yl)-3-butyn-1-yl) isoindole-1,3-dione 3-Bromo-5-fluoro-2-methoxypyridine (24.4 g), 2-(3-butyn-1-yl)isoindole-1,3-dione (23.6 g) and triethylamine (66 mL) were dissolved in DMF (200 mL) at room temperature. Nitrogen gas was bubbled into the reaction system for 10 minutes, and then thereto were added tetrakis(triphenylphosphine)palladium (7.0 g) and cuprous iodide (2.3 g). The mixture was heated to 90° C. and stirred for 2 h under the protection of nitrogen gas, and then cooled to room temperature. Methanol (100 mL) was added, and a large amount of solid was precipitated out, and then filtered. The filter cake was washed with methanol and dried in vacuo to afford the title compound (38.3 g).
$^1$HNMR (400 MHz, CDCl$_3$) δ7.89-7.86 (m, 3H), 7.75-7.73 (m, 2H), 7.35-7.30 (m, 1H), 3.99 (t, J=7.2 Hz, 2H), 3.85 (s, 3H), 2.90 (t, J=7.2 Hz, 2H).

Step C-1: Synthesis of 4-(5-fluoro-2-methoxypyridin-3-yl)-3-butyn-1-amine

To a mixture solution of 2-(4-(5-fluoro-2-methoxypyridin-3-yl)-3-butyn-1-yl)isoindole-1,3-dione (38.3 g) in methanol (120 mL) and dichloromethane (600 mL) was slowly added hydrazine hydrate (12.0 g, 80% purity) dropwise at room temperature, stirred at room temperature for 12 h, and then filtered. The filter cake was washed with dichloromethane. To the filtrate was added water (500 mL), and then the resulting mixture was layered. The organic phase was dried over anhydrous sodium sulfate and then filtered, and the filtrate was concentrated under reduced pressure to afford the title compound (17.6 g).

Step D-1: Synthesis of 3-(3,4-dihydro-2H-pyrrol-5-yl)-5-fluoro-2-methoxypyridine At room temperature, 4-(5-fluoro-2-methoxypyridin-3-yl)-3-butyn-1-amine (17.6 g) and palladium chloride (178 mg) were added to a mixture of acetonitrile (200 mL) and water (70 mL), and the resulting mixture solution was stirred at 80° C. for 5 h, cooled to room temperature and then concentrated under reduced pressure to remove acetonitrile. The resulting residue was extracted with dichloromethane (200 mL×3), and the combined organic phase was dried over anhydrous sodium sulfate and then filtered. The filtrate was concentrated, and the residue was purified by silica gel column chromatography (eluent: petroleum ether:ethyl acetate=20:1 (V:V)) to afford the title compound (11.2 g).
$^1$H NMR (400 MHz, CDCl$_3$) δ8.04 (d, J=3.2 Hz, 1H), 7.92 (dd, J=8.4, 2.8 Hz, 1H), 4.05-3.96 (m, 5H), 3.03-2.98 (m, 2H), 2.04-1.96 (m, 2H).

Step E-1: 5-Fluoro-2-methoxy-3-(pyrrolidin-2-yl)pyridine

To a mixture solution of 3-(3,4-dihydro-2H-pyrrol-5-yl)-5-fluoro-2-methoxypyridine (11.2 g) in methanol (100 mL) and water (25 mL) was added NaBH$_4$ (4.4 g) portionwise at 0° C. After completion of the addition, the resulting mixture was slowly warmed to room temperature and stirred for 2 h. The reaction mixture was quenched with 2N aqueous hydrochloric acid solution, and then concentrated under reduced pressure to remove methanol. Then the pH of the reaction system was adjusted to 8 with a saturated aqueous sodium hydroxide solution, and extracted with dichloromethane (100 mL×3). The combined organic phase was dried over anhydrous sodium sulfate and then filtered, and the filtrate was concentrated to afford the title compound (11.3 g).
$^1$H NMR (400 MHz, CDCl$_3$) δ 7.83 (d, J=3.2 Hz, 1H), 7.56 (dd, J=8.8, 3.2 Hz, 1H), 4.28 (t, J=7.6 Hz, 1H), 3.92 (s, 3H), 3.15-3.01 (m, 2H), 2.28-2.19 (m, 1H), 1.95-1.78 (m, 3H), 1.59-1.52 (m, 1H).

Intermediate 2: Synthesis of (R)-5-fluoro-2-methoxy-3-(pyrrolidin-2-yl)pyridine hydrochloride

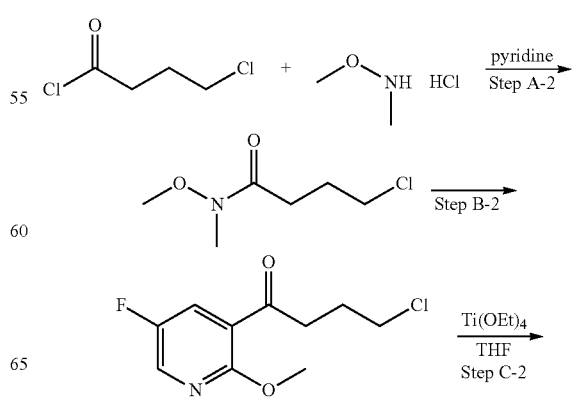

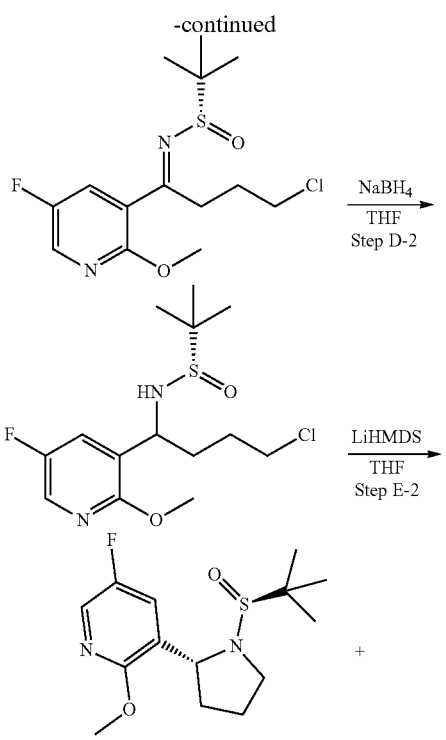

Step A-2: Synthesis of 4-chloro-N-methoxy-N-methylbutyramide

To a solution of N,O-dimethylhydroxylamine hydrochloride (100.0 g) in DCM (1500 mL) was added pyridine (250 mL) at 0° C. under stirring and continuously stirred for 30 min. To this mixture was then added 4-chlorobutyryl chloride (145.0 g) dropwise. After completion of the addition, the reaction mixture was warmed to room temperature and continuously stirred for 2 h. The reaction mixture was poured into water (250 mL), and then extracted with dichloromethane (100 mL×3). The organic phase was washed sequentially with 1 N hydrochloric acid, water and then a saturated saline solution, dried over anhydrous sodium sulfate, and then filtered. The filtrate was concentrated under reduced pressure to afford the title compound (125.1 g).

Step B-2: Synthesis of 4-chloro-1-(5-fluoro-2-methoxypyridin-3-yl)butan-1-one To a solution of 3-bromo-5-fluoro-2-methoxypyridine (20.0 g) in THF (200 mL) was added n-butyllithiuma (2.5 M solution in hexane)(43 mL) dropwise at −90° C., during which the temperature of the reaction system was maintained at −90° C. After completion of the dropwise addition, the resulting mixture was stirred at −90° C. for 2 h, and then to the reaction mixture was added a solution of 4-chloro-N-methoxy-N-methylbutyramide (17.7 g) in THF (100 mL) dropwise, during which the temperature of the reaction system was maintained at −90° C. After completion of the dropwise addition, the reaction temperature was gradually warmed to 10° C. The reaction mixture was quenched with a saturated aqueous ammonium chloride solution and then extracted with ethyl acetate (100 mL×3). The organic phase was washed with water and then a saturated saline solution. Then the organic phase was dried over anhydrous sodium sulfate and filtered, and the filtrate was concentrated under reduced pressure. The residue was purified by silica gel column chromatography (eluent: petroleum ether:ethyl acetate=20:1 (V:V)) to afford the title compound (3.82 g).
$^1$H NMR (400 MHz, CDCl$_3$) δ8.17 (d, J=3.2 Hz, 1H), 7.88 (dd, J=8.0, 3.2 Hz, 1H), 4.05 (s, 3H), 3.66 (t, J=6.4 Hz, 2H), 3.22 (t, J=7.2 Hz, 2H), 4.19 (dd, J=13.2, 6.4 Hz, 2H).

Step C-2: Synthesis of (S,E)-N-(4-chloro-1-(5-fluoro-2-methoxypyridin-3-yl) butylene)-2-methyl-propane-2-sulfinamide To a solution of 4-chloro-1-(5-fluoro-2-methoxypyridin-3-yl)butan-1-one (3.82 g) and (S)-2-methylpropane-2-sulfinamide (3.01 g) in THF (20 mL) was added tetraethyl titanate (5.66 g) at room temperature under stirring. The mixture was continuously stirred at 70° C. for 5 h. Then the reaction mixture was cooled to room temperature, quenched with a saturated aqueous ammonium chloride solution and filtered, and the filter cake was washed with ethyl acetate. The filtrate was layered and the organic phase was washed with water and then a saturated saline solution. Then the organic phase was dried over anhydrous sodium sulfate and filtered, and the filtrate was concentrated under reduced pressure to afford the title compound (5.09 g).

Step D-2: Synthesis of (S)—N-(4-chloro-1-(5-fluoro-2-methoxypyridin-3-yl)butyl)-2-methylpropane-2-sulfinamide To a solution of (S,E)-N-(4-chloro-1-(5-fluoro-2-methoxypyridin-3-yl)butylene)-2-methylpropane-2-sulfinamide (5.09 g) in THF (20 mL) was added NaBH$_4$ (576 mg) portionwise at −78° C., during which the reaction system was maintained at a temperature no higher than −78° C. After completion of the portionwise addition, the resulting mixture was slowly warmed to room temperature and stirred for 1 h. Then the reaction solution was slowly poured into an ice water to be quenched, and extracted with ethyl acetate (50 mL×3). The combined organic phase was dried over anhydrous sodium sulfate and filtered, and the filtrate was concentrated under reduced pressure to afford the title compound (5.12 g).

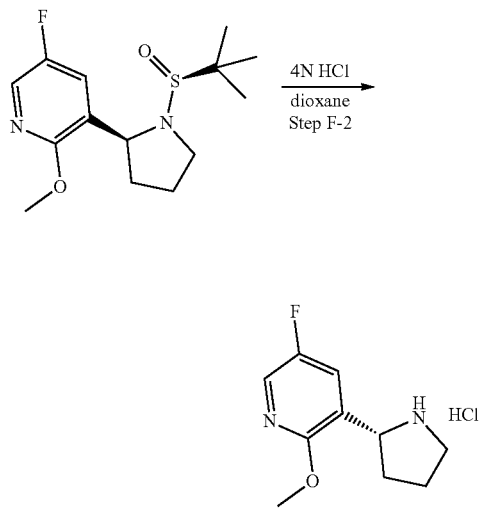

Step E-2: Synthesis of 3-((R)-1-((S)-tert-butylsulfinyl)pyrrolidin-2-yl)-5-fluoro-2-methoxypyridine and 3-((S)-1-((S)-tert-butylsulfinyl)pyrrolidin-2-yl)-5-fluoro-2-methoxypyridine

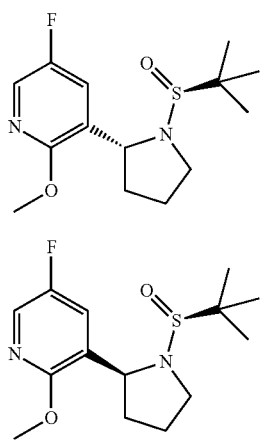

To a solution of (S)—N-(4-chloro-1-(5-fluoro-2-methoxypyridin-3-yl)butyl)-2-methylpropane-2-sulfinamide (5.12 g) in THF (30 mL) was added slowly LiHMDS (1 M solution in THF) (23 mL) dropwise at −78° C., during which the reaction system was maintained at a temperature no higher than −78° C. After completion of the dropwise addition, the resulting mixture was slowly warmed to room temperature and stirred at room temperature for 2 h, and then quenched with a saturated aqueous ammonium chloride solution and extracted with ethyl acetate (50 mL×3). The combined organic phase was dried over anhydrous sodium sulfate and filtered, and the filtrate was concentrated under reduced pressure. The residue was purified by silica gel column chromatography (eluent: petroleum ether:ethyl acetate=20:1 (V:V)) to afford the two title compounds (1.1 g), respectively.

E-2-1: $^1$H NMR (400 MHz, CDCl$_3$) δ7.88 (d, J=3.2 Hz, 1H), 7.32 (dd, J=8.4, 3.2 Hz, 1H), 4.96 (t, J=6.8 Hz, 1H), 3.94 (s, 3H), 3.91-3.85 (m, 1H), 3.00-2.94 (m, 1H), 2.25-2.20 (m, 1H), 1.91-1.83 (m, 2H), 1.75-1.68 (m, 1H), 1.18 (s, 9H). m/z=301[M+1]$^+$.

E-2-2: $^1$H NMR (400 MHz, CDCl$_3$) 7.87 (d, J=2.8 Hz, 1H), 7.32 (dd, J=8.4, 2.8 Hz, 1H), 5.22 (d, J=8.0 Hz, 1H), 3.93 (s, 3H), 3.65-3.54 (m, 2H), 2.14-2.09 (m, 1H), 1.93-1.88 (m, 1H), 1.75-1.68 (m, 2H), 1.18 (s, 9H). m/z=301[M+1]$^+$.

Step F-2: Synthesis of (R)-5-fluoro-2-methoxy-3-(pyrrolidin-2-yl)pyridine hydrochloride Compound E-2-1 (2.25 g) as a solid was dissolved in dichloromethane (20 mL) at −10° C., and a solution of HCl in 1,4-dioxane (4 M, 10 mL) was slowly added dropwise thereto. After completion of the dropwise addition, the resulting mixture was warmed to room temperature, and stirred for 10 min. A large amount of white solid was precipitated out and filtered, and the filter cake was washed with dichloromethane and then dried in vacuo to afford the title compound (1.75 g).

$^1$H NMR (400 MHz, DMSO-d$_6$) δ10.07 (brs, 1H), 9.31 (brs, 1H), 8.18 (d, J=3.2 Hz, 1H), 7.32 (dd, J=8.8, 3.2 Hz, 1H), 4.62 (t, J=7.6 Hz, 1H), 3.89 (s, 3H), 3.28-3.24 (m, 2H), 2.30-2.24 (m, 1H), 2.10-1.91 (m, 3H). m/z=197[M+1]$^+$.

Intermediates 3 and 4: Synthesis of (R)-2-(5-fluoro-2-methoxyphenyl) pyrrolidine (Intermediate 3) and (S)-2-(5-fluoro-2-methoxyphenyl)pyrrolidine (Intermediate 4)

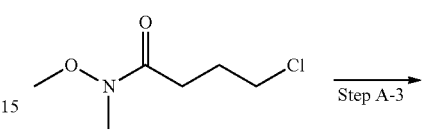

Step A-3

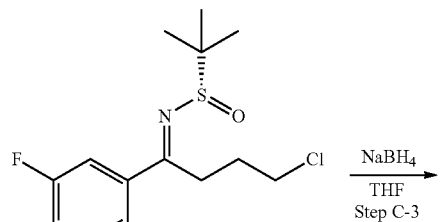

Step B-3

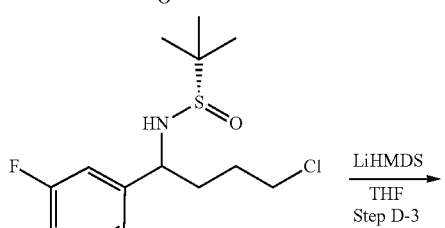

Step C-3

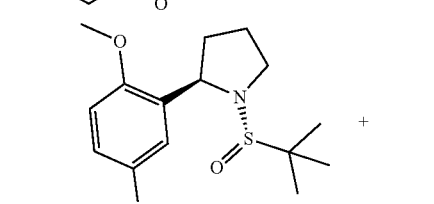

Step D-3

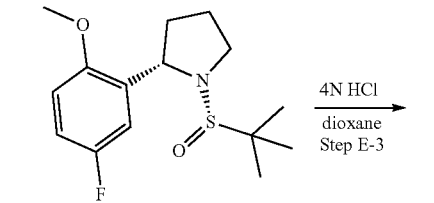

Step E-3

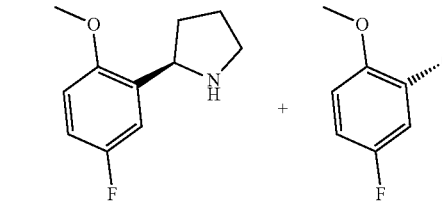

Intermediate 3    Intermediate 4

Step A-3: Synthesis of 4-chloro-1-(5-fluoro-2-methoxyphenyl)butan-1-one

To a solution of 2-bromo-4-fluoroanisole (23.5 g) in THF (150 mL) was added a solution of isopropylmagnesium chloride (2M) in THF (54 mL) dropwise at −50° C. After completion of the dropwise addition, the reaction mixture was warmed to room temperature and continuously stirred for 1 h, and then cooled to −50° C. again. To the reaction mixture was added a solution of 4-chloro-N-methoxy-N-methylbutyramide (9.0 g) in THF (30 mL) dropwise under stirring. After completion of the dropwise addition, the resulting mixture was gradually warmed to 30° C. and continuously stirred at 30° C. for 2 h. Then the reaction mixture was quenched with a saturated aqueous ammonium chloride solution and extracted with ethyl acetate (100 mL×3). The combined organic phase was dried over anhydrous sodium sulfate and filtered, and the filtrate was concentrated under reduced pressure. The residue was purified by silica gel column chromatography (eluent: petroleum ether:ethyl acetate=20:1 (V:V)) to afford the title compound (7.6 g).

$^1$H NMR (400 MHz, CDCl$_3$) δ 7.33 (dd, J=9.0, 3.2 Hz, 1H), 7.07-7.02 (m, 1H), 6.83 (dd, J=9.0, 4.0 Hz, 1H), 3.81 (s, 3H), 3.55 (t, J=6.4 Hz, 2H), 3.07 (t, J=7.0 Hz, 2H), 2.12-2.15 (m, 2H).

Steps B-3, C-3 and D-3 were carried out sequentially with reference to Steps C-2, D-2 and E-2 as shown in the synthetic method of Intermediate 2.

Step E-3: Synthesis of (R)-2-(5-fluoro-2-methoxyphenyl)pyrrolidine

To a solution of (R)-1-((S)-tert-butylsulfinyl)-2-(5-fluoro-2-methoxyphenyl) pyrrolidine (2.8 g) in 1,4-dioxane (25 mL) was slowly added a solution of HCl in 1,4-dioxane (4 M, 14 mL) dropwise at 0° C. After completion of the dropwise addition, the resulting mixture was warmed to room temperature and continuously stirred for 1 h, and then adjusted to pH=8 with an aqueous NaOH solution and extracted with ethyl acetate (100 mL×3). The combined organic phase was dried over anhydrous sodium sulfate and filtered, and the filtrate was concentrated under reduced pressure to afford the intermediate compound 3 (1.8 g).

Intermediate 3: $^1$H NMR (400 MHz, CDCl$_3$) δ 7.19 (dd, J=9.6, 3.0 Hz, 1H), 6.92-6.83 (m, 1H), 6.75 (dd, J=8.8, 4.4 Hz, 1H), 4.38 (t, J=7.6 Hz, 1H), 3.80 (s, 3H), 3.19-3.14 (m, 1H), 3.10-2.98 (m, 1H), 2.89 (brs, 1H), 2.34-2.12 (m, 1H), 1.96-1.76 (m, 2H), 1.72-1.52 (m, 1H).

Intermediate 4: Referring to the method in Step E-3, the intermediate compound 4 was prepared by using (S)-1-((S)-tert-butylsulfinyl)-2-(5-fluoro-2-methoxyphenyl)pyrrolidine as a starting material.

$^1$H NMR (400 MHz, CDCl$_3$) δ 7.19 (dd, J=9.6, 3.0 Hz, 1H), 6.92-6.83 (m, 1H), 6.75 (dd, J=8.8, 4.4 Hz, 1H), 4.38 (t, J=7.6 Hz, 1H), 3.80 (s, 3H), 3.19-3.14 (m, 1H), 3.10-2.98 (m, 1H), 2.89 (brs, 1H), 2.34-2.12 (m, 1H), 1.96-1.76 (m, 2H), 1.72-1.52 (m, 1H).

Intermediate 5: Synthesis of (R)-2-methoxy-3-(pyrrolidin-2-yl)pyridine

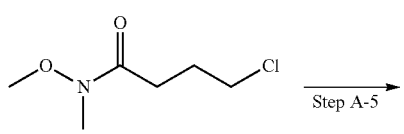

Step A-5

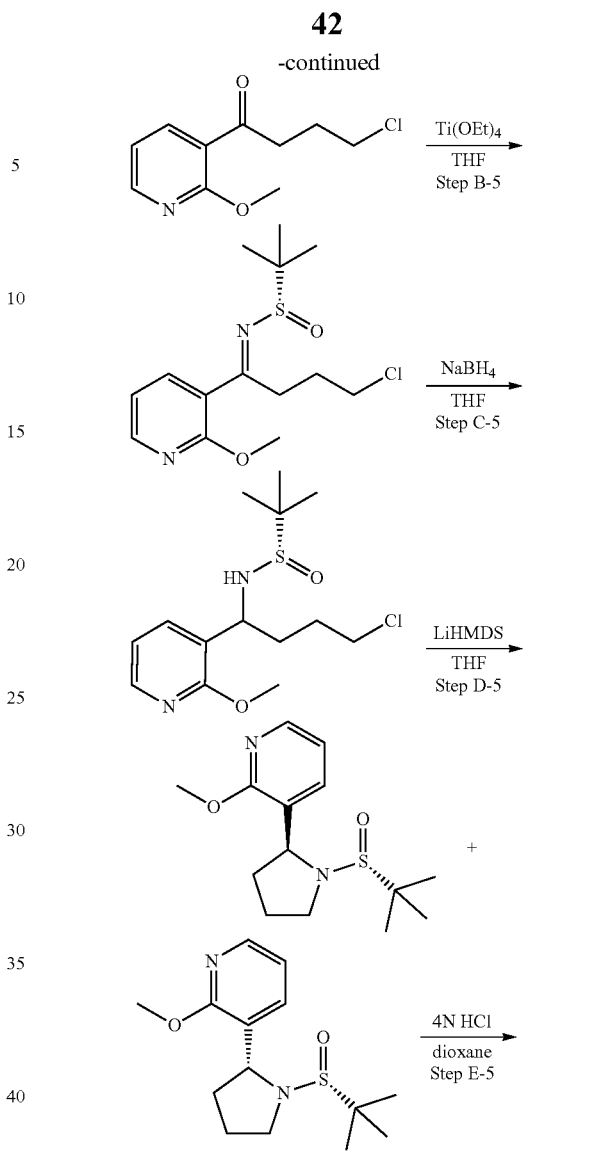

The synthesis of Intermediate 5 was carried out by using 2-methoxy-3-bromopyridine as a starting material with reference to the synthetic procedures of Intermediate 3 and Intermediate 4.

Intermediate 5: $^1$H NMR (400 MHz, CDCl$_3$) δ 8.03 (d, J=4.0 Hz, 1H), 7.69 (d, J=7.2 Hz, 1H), 6.85 (dd, J=7.2, 5.2

Hz, 1H), 4.28 (t, J=7.6 Hz, 1H), 3.96 (s, 3H), 3.14-3.19 (m, 1H), 3.06-3.00 (m, 1H), 2.16-2.24 (m, 2H), 1.82-1.89 (m, 2H), 1.60-1.65 (m, 1H).

Intermediate 6: Synthesis of (R,S)-2-methoxy-3-(pyrrolidin-2-yl)pyridine

The synthesis of Intermediate 6 was carried out by using the racemate product obtained in Step D-5 in the synthesis of Intermediate 5 as a starting material with reference to the synthetic step E-5.

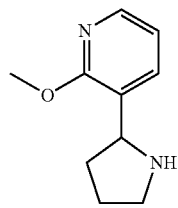

$^1$H NMR (400 MHz, CDCl$_3$) δ 8.03 (d, J=4.0 Hz, 1H), 7.69 (d, J=7.2 Hz, 1H), 6.85 (dd, J=7.2, 5.2 Hz, 1H), 4.28 (t, J=7.6 Hz, 1H), 3.96 (s, 3H), 3.14-3.19 (m, 1H), 3.06-3.00 (m, 1H), 2.16-2.24 (m, 2H), 1.82-1.89 (m, 2H), 1.60-1.65 (m, 1H).

Intermediate 7: Synthesis of 2-methoxy-6-(pyrrolidin-2-yl)pyridine

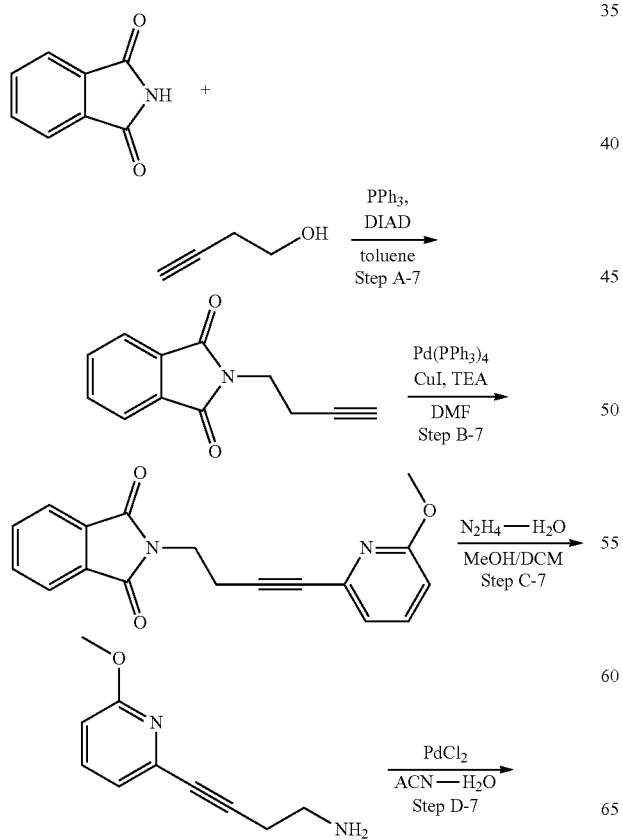

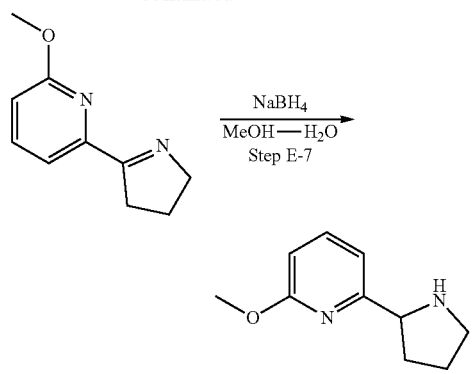

The synthesis of Intermediate 7 was carried out by using 2-methoxy-6-bromopyridine as a starting material with reference to the synthetic procedure of Intermediate 1.

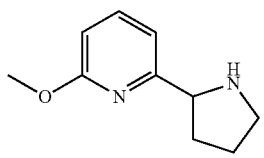

Intermediate 7: $^1$H NMR (400 MHz, CDCl$_3$) δ7.50 (t, J=8.0 Hz, 1H), 6.85 (d, J=7.6 Hz, 1H), 6.58 (d, J=8.4 Hz, 1H), 4.14 (t, J=7.2 Hz, 1H), 3.92 (s, 3H), 3.26-3.20 (m, 1H), 3.01-2.95 (m, 1H), 2.48 (brs, 1H), 2.18-2.13 (m, 1H), 1.89-1.74 (m, 3H).

Intermediate 8: Synthesis of (R)-4-methoxy-3-(pyrrolidin-2-yl)pyridine

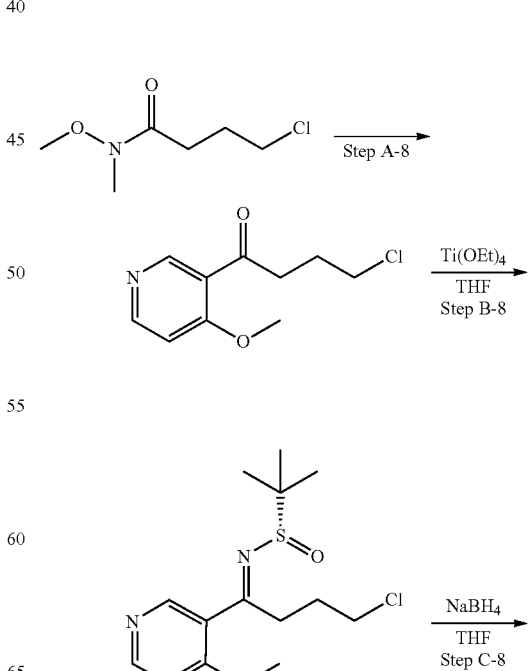

-continued
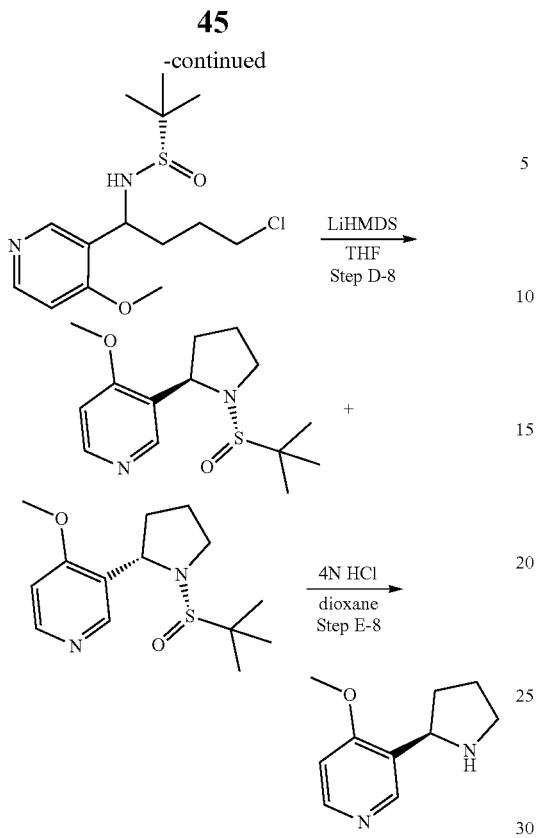
The synthesis of Intermediate 8 was carried out by using 3-bromo-4-methoxypyridine as a starting material with reference to the synthetic procedures of Intermediate 3 and Intermediate 4.
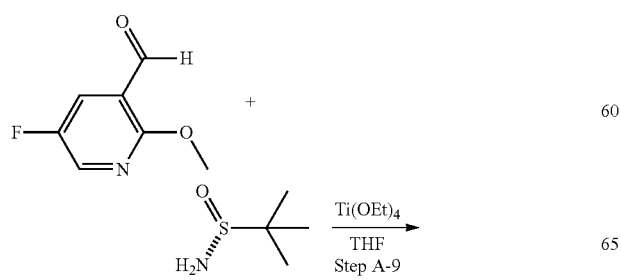
Intermediate 8: $^1$H NMR (400 MHz, CDCl$_3$) δ 8.51 (s, 1H), 8.40 (d, J=5.6 Hz, 1H), 6.76 (d, J=6.0 Hz, 1H), 4.33 (t, J=7.6 Hz, 1H), 3.88 (s, 3H), 3.71 (brs, 1H), 3.22-3.16 (m, 1H), 3.05-2.99 (m, 1H), 2.21-2.14 (m, 2H), 1.91-1.85 (m, 1H), 1.75-1.68 (m, 1H).
Intermediate 9: Synthesis of 5-fluoro-3-((2R,4S)-4-fluoropyrrolidin-2-yl)-2-methoxypyridine
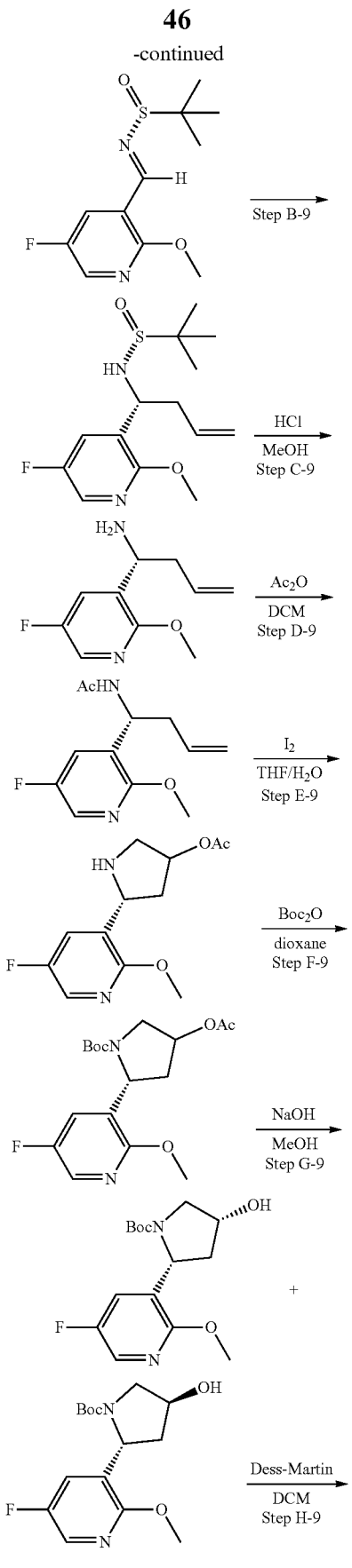

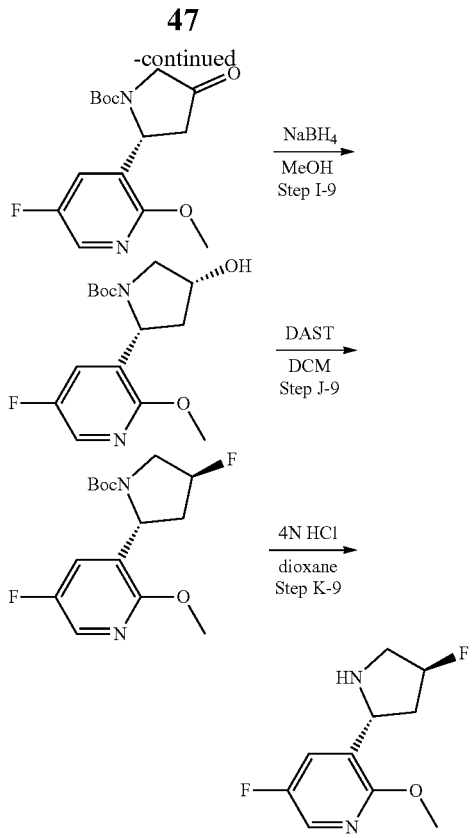

Step A-9: Synthesis of (R,E)-N-((5-fluoro-2-methoxypyridin-3-yl)methylene)-2-methylpropane-2-sulfinamide To a solution of 5-fluoro-2-methoxynicotinaldehyde (54 g) in tetrahydrofuran (250 mL) was added (R)-tert-butylsulfinamide (54.8 g) at 0° C., and then to the reaction system was added tetraethyl titanate (103.2 g) dropwise. After completion of the dropwise addition, the resulting mixture was warmed to room temperature and continuously stirred for 3 h. After the reaction system was cooled to 0° C., a saturated saline solution (80 mL) was added dropwise thereto and the resulting mixture was continuously stirred for 20 min, and then filtered. The filter cake was washed with dichloromethane, and the washings and the filtrate were combined and then layered. The organic phase was dried over anhydrous sodium sulfate and filtered, and the filtrate was concentrated under reduced pressure. The residue was purified by silica gel column chromatography (eluent: petroleum ether:ethyl acetate=20:1 (V:V)) to afford the title compound (88.0 g).

$^1$H NMR (400 MHz, CDCl$_3$) δ8.89 (d, J=2.4 Hz, 1H), 8.15 (d, J=3.2 Hz, 1H), 7.98 (dd, J=8.0, 2.8 Hz, 1H), 4.01 (s, 3H), 1.27 (s, 9H).

Step B-9: Synthesis of (R)—N—((R)-1-(5-fluoro-2-methoxypyridin-3-yl)but-3-enyl)-2-methylpropane-2-sulfinamide To a solution of (R,E)-N-((5-fluoro-2-methoxypyridin-3-yl)methylene)-2-methylpropane-2-sulfinamide (88.0 g) in hexamethylphosphoric triamide (400 mL) were sequentially added 3-bromopropylene (59.2 ml), zinc powder (44.7 g) and water (6.15 ml) at 0° C., and an ice bath was removed after completion of the addition. The resulting mixture was warmed to 25° C. and stirred overnight, and then cooled to 0° C. To the reaction system was added water (500 ml) and stirred for 20 min. Then methyl tert-butyl ether (500 mL) and 10% citric acid solution (100 mL) were added thereto, and continuously stirred for 30 min. The resulting mixture was suction-filtered, and the filtrate was layered. The organic phase was dried over anhydrous sodium sulfate and filtered, and the filtrate was concentrated under reduced pressure. The residue was purified by silica gel column chromatography (eluent: petroleum ether:ethyl acetate=20:1 (V:V)) to afford the title compound (48.4 g).

$^1$H NMR (400 MHz, CDCl$_3$) δ7.90 (d, J=3.2 Hz, 1H), 7.34 (dd, J=8.0, 2.8 Hz, 1H), 5.69-5.60 (m, 1H), 5.08-5.03 (m, 2H), 4.50 (dd, J=14.8, 7.2 Hz, 1H), 4.07 (d, J=8.0 Hz, 1H), 3.97 (s, 3H), 2.65-1.72 (m, 2H), 1.21 (s, 9H).

Step C-9: Synthesis of (R)-1-(5-fluoro-2-methoxypyridin-3-yl)but-3-en-1-amine To a solution of (R)—N—((R)-1-(5-fluoro-2-methoxypyridin-3-yl)but-3-enyl)-2-methylpropane-2-sulfinamide (48.4 g) in methanol (250 mL) was added a solution of HCl in 1,4-dioxane (4 M, 67.5 mL) at room temperature, stirred for 2 h, and then concentrated under reduced pressure. The residue was poured into water (250 mL), and the resulting mixture was adjusted to pH=8 with a saturated aqueous sodium bicarbonate solution and then extracted with ethyl acetate (200 mL×3). The combined organic phase was dried over anhydrous sodium sulfate and filtered, and the filtrate was concentrated under reduced pressure to afford the title compound (40.0 g).

Step D-9: Synthesis of (R)—N-(1-(5-fluoro-2-methoxypyridin-3-yl)but-3-enyl) acetamide To a solution of (R)-1-(5-fluoro-2-methoxypyridin-3-yl)-but-3-en-1-amine (40.0 g) in dichloromethane (200 mL) were added pyridine (19.5 mL) and acetic anhydride (16 mL) at 0° C. The resulting mixture was warmed to room temperature and stirred overnight. The reaction solution was poured into a saturated aqueous sodium bicarbonate solution (500 mL), and extracted with dichloromethane (200 mL×3). The combined organic phase was dried over anhydrous sodium sulfate and filtered, and the filtrate was concentrated under reduced pressure to afford the title compound (37.9 g).

$^1$H NMR (400 MHz, CDCl$_3$) δ7.90 (d, J=2.8 Hz, 1H), 7.30 (dd, J=8.0, 2.8 Hz, 1H), 6.22 (d, J=8.0 Hz, 1H), 5.67-5.58 (m, 1H), 5.13-5.04 (m, 3H), 3.98 (s, 3H), 2.56-2.52 (m, 2H), 2.00 (s, 3H).

Step E-9: Synthesis of (5R)-5-(5-fluoro-2-methoxypyridin-3-yl)pyrrolidin-3-yl acetate To a solution of (R)—N-(1-(5-fluoro-2-methoxypyridin-3-yl)but-3-enyl)acetamide (37.6 g) in tetrahydrofuran (360 mL) and water (84 mL) was added iodine (113.7 g) at room temperature, and stirred overnight. To the reaction solution were added a saturated aqueous sodium bicarbonate solution (100 mL) and a saturated aqueous sodium sulfite solution (100 mL), and the resulting mixture was extracted with ethyl acetate (100 mL×3). The combined organic phase was dried over anhydrous sodium sulfate and filtered, and the filtrate was concentrated under reduced pressure to afford the title compound (43.0 g).

Step F-9: Synthesis of tert-butyl (2R)-4-acetoxy-2-(5-fluoro-2-methoxypyridin-3-yl) pyrrolidine-1-carboxylate To a solution of (5R)-5-(5-fluoro-2-methoxypyridin-3-yl) pyrrolidin-3-yl acetate (43.0 g) in 1,4-dioxane (250 mL) were added Boc anhydride (56.0 mL) dropwise and then an aqueous sodium hydroxide solution (50 mL) with pH=9 at room temperature, and stirred for 3 h. To the reaction system was added 1 L of water, and the resulting mixture was extracted with ethyl acetate (100 mL×3). The combined organic phase was dried over anhydrous sodium sulfate and filtered, and the filtrate was concentrated under reduced pressure to afford the title compound (45.0 g).

Step G-9: Synthesis of tert-butyl (2R,4RS)-2-(5-fluoro-2-methoxypyridin-3-yl)-4-hydroxypyrrolidine-1-carboxylate To a solution of tert-butyl (2R)-4-acetoxy-2-(5-fluoro-2-methoxypyridin-3-yl) pyrrolidine-1-carboxylate (45.0 g) in methanol (500 mL) was added a sodium hydroxide solution (2N, 88 mL) at room temperature, and stirred for 1 h. The resulting mixture was concentrated under reduced pressure to remove the solvent, and to the residue was added hydrochloric acid (1 N, 180 mL). Then the resulting mixture was extracted with dichloromethane (150 mL×3). The combined organic phase was dried over anhydrous sodium sulfate and filtered, and the filtrate was concentrated under reduced pressure. The residue was purified by silica gel column chromatography (eluent: petroleum ether:ethyl acetate=10:1 (V:V)) to afford the title compound (34.0 g).

Step H-9: Synthesis of tert-butyl (R)-2-(5-fluoro-2-methoxypyridin-3-yl)-4-oxopyrrolidine-1-carboxylate Tert-butyl (2R,4RS)-2-(5-fluoro-2-methoxypyridin-3-yl)-4-hydroxypyrrolidine-1-carboxylate (15.1 g) was dissolved in dichloromethane (200 mL), and thereto were added sodium bicarbonate (4.06 g) and then Dess-Martin periodinane (92 g) at room temperature and stirred overnight. To the reaction solution was added a saturated aqueous sodium bicarbonate solution to adjust the pH to 7, and the resulting mixture was extracted with dichloromethane (150 mL×3). The combined organic phase was dried over anhydrous sodium sulfate and filtered, and the filtrate was concentrated under reduced pressure. The residue was purified by silica gel column chromatography (eluent: petroleum ether:ethyl acetate=10:1 (V:V)) to afford the title compound (10.1 g).
$^1$H NMR (400 MHz, CDCl$_3$) δ7.92 (brs, 1H), 7.30 (brs, 1H), 5.30-5.16 (m, 1H), 4.09-3.88 (m, 5H), 3.06 (dd, J=18.4, 10.8 Hz, 1H), 2.56 (d, J=18.0 Hz, 1H), 1.47-1.29 (m, 9H).

Step I-9: Synthesis of tert-butyl (2R,4R)-2-(5-fluoro-2-methoxypyridin-3-yl)-4-hydroxypyrrolidine-1-carboxylate To a solution of tert-butyl (R)-2-(5-fluoro-2-methoxypyridin-3-yl)-4-oxopyrrolidine-1-carboxylate (14 g) in methanol (100 mL) was added sodium borohydride (1.42 g) portionwise at 0° C., and the resulting mixture was maintained at 0° C., and stirred for 45 min. To the reaction solution was added a saturated aqueous ammonium chloride solution (100 mL), and the resulting mixture was gradually warmed to room temperature, and then extracted with dichloromethane (150 mL×3). The combined organic phase was dried over anhydrous sodium sulfate and filtered, and the filtrate was concentrated under reduced pressure. The residue was purified by silica gel column chromatography (eluent: petroleum ether:ethyl acetate=10:1 (V:V)) to afford the title compound (13.6 g).
$^1$H NMR (400 MHz, CDCl$_3$) δ7.84 (brs, 1H), 7.35-7.19 (m, 1H), 5.09-4.92 (m, 1H), 4.44 (d, J=2.8 Hz, 1H), 3.91 (s, 3H), 3.73-3.70 (m, 1H), 3.62-3.55 (m, 1H), 2.50 (brs, 1H), 1.95 (dd, J=14.0, 1.2 Hz, 1H), 1.57-1.18 (m, 10H).

Step J-9: Synthesis of tert-butyl (2R,4S)-4-fluoro-2-(5-fluoro-2-methoxypyridin-3-yl) pyrrolidine-1-carboxylate To a solution of tert-butyl (2R,4R)-2-(5-fluoro-2-methoxypyridin-3-yl)-4-hydroxypyrrolidine-1-carboxylate (5.1 g) in dichloromethane (50 mL) was added diethylaminosulfur trifluoride (5.27 g) at −78° C. The resulting mixture was maintained at −78° C. and stirred for 20 min, and then gradually warmed to room temperature and stirred overnight. To the reaction system was added a saturated aqueous sodium bicarbonate solution (100 mL), and the resulting mixture was extracted with dichloromethane (100 mL×3). The combined organic phase was dried over anhydrous sodium sulfate and filtered, and the filtrate was concentrated under reduced pressure. The residue was purified by silica gel column chromatography (eluent: petroleum ether:ethyl acetate=10:1 (V:V)) to afford the title compound (3.71 g).
$^1$H NMR (400 MHz, CDCl$_3$) δ7.88 (brs, 1H), 7.23-2.16 (m, 1H), 5.29-5.02 (m, 2H), 4.13-4.04 (m, 1H), 3.94 (s, 3H), 3.71-3.58 (m, 1H), 2.84-2.61 (m, 1H), 2.09-1.80 (m, 1H), 1.50-1.12 (m, 9H).

Step K-9: Synthesis of 5-fluoro-3-((2R,4S)-4-fluoropyrrolidin-2-yl)-2-methoxypyridine To tert-butyl (2R,4S)-4-fluoro-2-(5-fluoro-2-methoxypyridin-3-yl)pyrrolidine-1-carboxylate (3.71 g) was added a solution of hydrogen chloride in 1,4-dioxane (4 M, 25 mL), and stirred at room temperature for 30 min. The resulting mixture was adjusted to pH=8 with a saturated aqueous sodium hydroxide solution, and then extracted with ethyl acetate (50 mL×3). The combined organic phase was dried over anhydrous sodium sulfate and filtered, and the filtrate was concentrated under reduced pressure to afford the title compound (3.0 g).
$^1$H NMR (400 MHz, CDCl$_3$) δ7.85 (d, J=3.2 Hz, 1H), 7.62 (dd, J=8.8, 3.2 Hz, 1H), 5.33-5.17 (m, 1H), 4.61 (t, J=7.2 Hz, 1H), 3.94 (s, 3H), 3.35 (dd, J=25.6, 13.6 Hz, 1H), 3.23-3.10 (m, 1H), 3.71-2.60 (m, 2H), 1.74-0.96 (m, 1H).

Intermediate 10: Synthesis of ethyl 2-amino-5-chloropyrazolo[1,5-a]pyrimidine-3-carboxylate

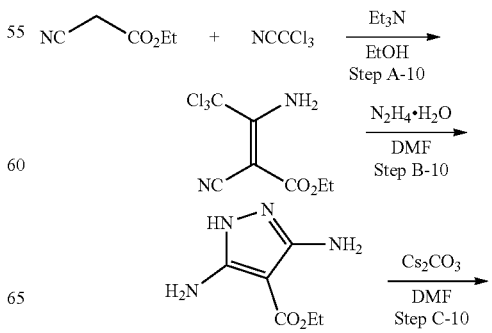

-continued

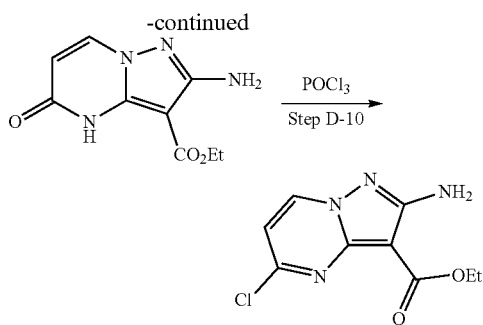

Step A-10: Synthesis of ethyl (Z)-3-amino-4,4,4-trichloro-2-cyano-butenoate

To a solution of ethyl cyanoacetate (41.22 g) and trichloroacetonitrile (100 g) in ethanol (120 mL) was added triethylamine (2.0 g) dropwise at 0° C. The resulting mixture was stirred at 0° C. for 2 hours, and then slowly warmed to room temperature and continuously stirred for 30 minutes. The resulting mixture was concentrated to remove the solvent, and the residue was purified by silica gel column chromatography (eluting with dichloromethane) to afford the title compound (93.0 g).

$^1$H NMR (400 MHz, CDCl$_3$) δ10.20 (brs, 1H), 6.93 (brs, 1H), 4.30 (q, J=7.2 Hz, 2H), 1.33 (t, J=7.2 Hz, 3H).

Step B-10: Synthesis of ethyl 3,5-diamino-1H-pyrazole-4-carboxylate

To a solution of ethyl (Z)-3-amino-4,4,4-trichloro-2-cyano-butenoate (92.1 g) in DMF (250 mL) was slowly added hydrazine hydrate (50 g, a concentration of 80%) dropwise. The reaction mixture was heated to 100° C. and stirred for 1.5 hours, and then concentrated to remove the solvent. The residue was slurried with dichloromethane, and then suction-filtered. The solid was washed with dichloromethane and dried to afford the title compound (41.0 g).

$^1$H NMR (400 MHz, DMSO-d$_6$) δ10.4 (brs, 1H), 5.35 (brs, 4H), 4.13 (q, J=7.2 Hz, 2H), 1.24 (t, J=7.2 Hz, 3H).

Step C-10: Synthesis of ethyl 2-amino-5-oxo-4,5-dihydropyrazolo[1,5-a]pyrimidine-3-carboxylate

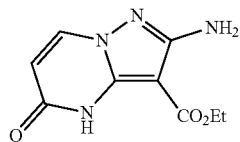 [SMILES: CCOC(=O)c1c(N)nn2ccc(=O)[nH]c12]

To a solution of sodium ethoxide (33.2 g) in ethanol (500 mL) were sequentially added ethyl 3,5-diamino-1H-pyrazole-4-carboxylate (20.8 g) and 1,3-dimethylpyrimidine-2,4(1H,3H)-dione (17.0 g) at room temperature. The reaction solution was stirred at 90° C. for 12 hours, cooled to room temperature, adjusted to pH=7 with 1N hydrochloric acid, and then filtered. The solid was washed with ethanol and then dried to afford the title compound (18.4 g).

$^1$H NMR (400 MHz, DMSO-d$_6$) δ11.17 (brs, 1H), 8.24 (d, J=8.0 Hz, 1H), 5.93 (s, 2H), 5.90 (d, J=8.0 Hz, 1H), 4.26 (q, J=7.2 Hz, 2H), 1.27 (t, J=7.2 Hz, 3H).

Step D-10: Synthesis of ethyl 2-amino-5-chloropyrazolo[1,5-a]pyrimidine-3-carboxylate To a solution of ethyl 2-amino-5-oxo-4,5-dihydropyrazolo[1,5-a]pyrimidine-3-carboxylate (33.6 g) in acetonitrile (500 mL) was added phosphorus oxychloride (110 mL) at room temperature. The resulting mixture was heated to 40° C. and continuously stirred for 5 hours, and then cooled to room temperature and concentrated under reduced pressure. To the residue was added a saturated aqueous sodium bicarbonate solution (250 mL), and the resulting mixture was extracted with ethyl acetate (200 mL×3).

The combined organic phase was dried over anhydrous sodium sulfate and filtered, and the filtrate was concentrated under reduced pressure. The residue was purified by silica gel column chromatography (eluent: ethyl acetate/petroleum ether=2:1 (V:V)) to afford the title compound (4.5 g).

$^1$H NMR (400 MHz, CDCl$_3$) δ8.29 (d, J=7.2 Hz, 1H), 6.80 (d, J=7.2 Hz, 1H), 5.51 (brs, 2H), 4.43 (q, J=7.2 Hz, 2H), 1.44 (t, J=7.2 Hz, 3H).

Intermediate 11: Synthesis of 5-fluoro-3-((2R,4R)-4-fluoropyrrolidin-2-yl)-2-methoxypyridine

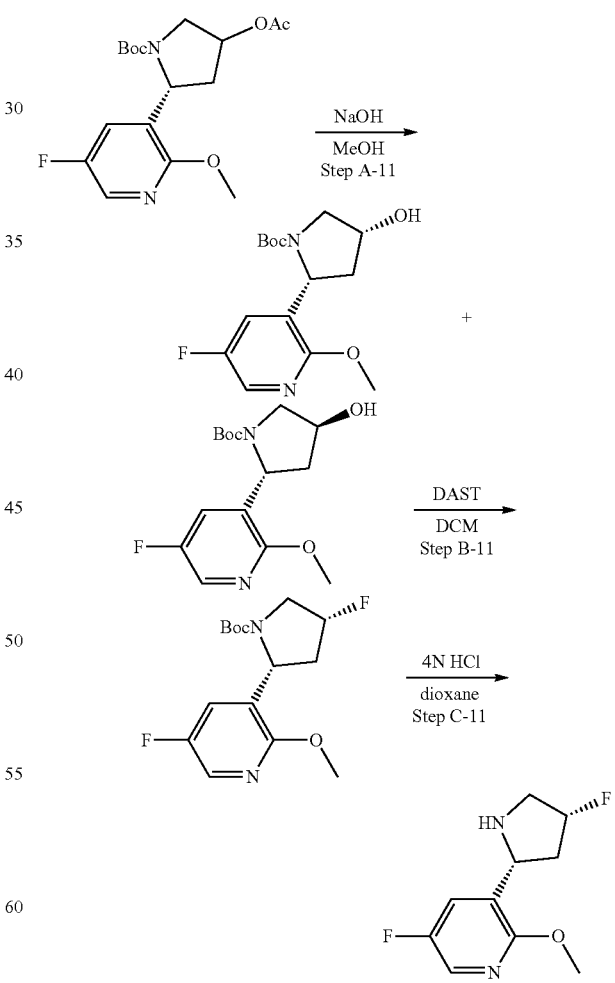

Intermediate 11 was synthesized by using tert-butyl (2R,4S)-2-(5-fluoro-2-methoxypyridin-3-yl)-4-hydroxypyrrolidine-1-carboxylate obtained in Step G-9 in the synthesis of Intermediate 9 as a starting material with reference to Step J-9 and Step K-9 in the synthesis of Intermediate 9.

$^1$H NMR (400 MHz, DMSO-d$_6$) δ 9.45 (brs, 1H), 8.13 (d, J=2.8 Hz, 1H), 7.93 (dd, J=9.2, 2.8, Hz, 1H), 5.60-5.42 (m, 1H), 4.87 (d, J=8.4 Hz, 1H), 3.90 (s, 3H), 3.58-3.36 (m, 2H), 2.77-2.60 (m, 1H), 2.49-2.36 (m, 1H).

Intermediate 12: Synthesis of (3R,5R)-5-(5-fluoro-2-methoxypyridin-3-yl) pyrrolidin-3-ol

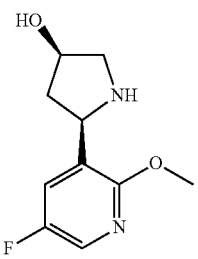

Intermediate 12 was synthesized by using tert-butyl (2R, 4R)-2-(5-fluoro-2-methoxypyridin-3-yl)-4-hydroxypyrrolidine-1-carboxylate obtained in step G-9 in the synthesis of Intermediate 9 as a starting material with reference to step K-9 in the synthesis of Intermediate 9.

$^1$H NMR (400 MHz, DMSO-d$_6$) δ 10.20 (s, 1H), 9.28 (s, 1H), 8.21 (d, J=3.2 Hz, 1H), 8.01 (dd, J=3.2, 9.2 Hz, 1H), 4.80 (t, J=7.2 Hz, 1H), 4.48-4.53 (m, 1H), 3.91 (s, 3H), 3.29-3.34 (m, 1H), 3.01-3.18 (m, 1H), 2.46-2.55 (m, 1H), 2.07-2.14 (m, 1H).

Intermediate 13: Synthesis of 4-fluoro-2-((2R,4S)-4-fluoropyrrolidin-2-yl)phenol

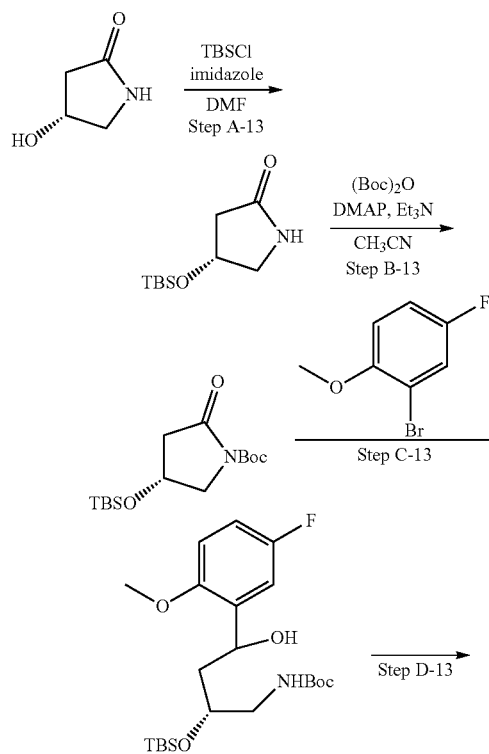

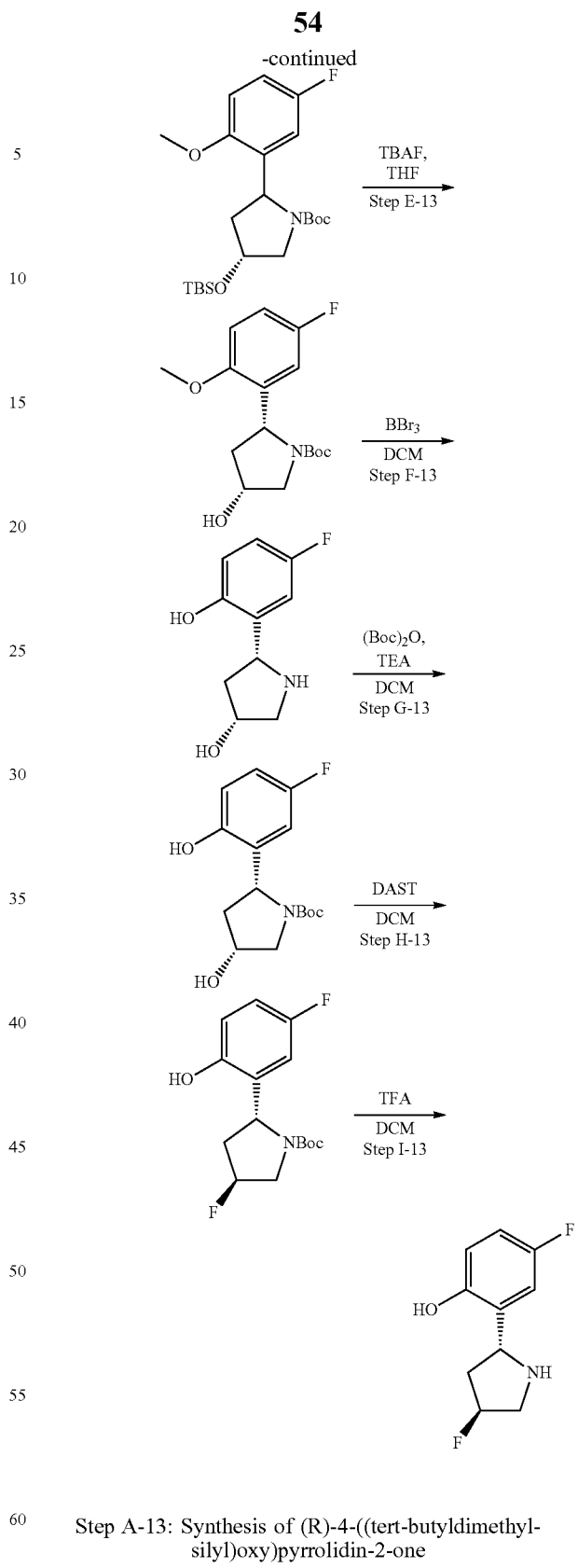

Step A-13: Synthesis of (R)-4-((tert-butyldimethylsilyl)oxy)pyrrolidin-2-one (R)-4-Hydroxy-2-pyrrolidone (6.0 g) was dissolved in DMF (60 mL), and thereto were added TBDMSCI (9.8 g) and imidazole (6.05 g) at 0° C. The resulting mixture was warmed to room temperature and stirred for 3 h. After monitoring the completion of reaction, to the reaction system was added water. A solid was precipitated out, filtered and dried overnight under an infrared lamp to afford the title compound (10.7 g).

$^1$H NMR (400 MHz, CDCl$_3$) δ 7.45 (s, 1H), 4.44 (m, 1H), 3.42 (m, 1H), 2.93 (m, 1H), 2.40 (m, 1H), 1.85 (m, 1H), 0.79 (s, 9H), 0.00 (s, 6H).

Step B-13: Synthesis of tert-butyl (R)-4-((tert-butyldimethylsilyl)oxy)-2-oxopyrrolidine-1-carboxylate To a solution of (R)-4-((tert-butyldimethylsilyl)oxy)pyrrolidin-2-one (10.67 g) in acetonitrile were added triethylamine (8.26 mL) and DMAP (3.0 g) at 0° C., and then was added (Boc)$_{20}$ (15 mL) dropwise under the protection of nitrogen gas. After completion of the addition, the reaction mixture was stirred for 5 min, and then warmed to room temperature and continuously stirred overnight. The reaction system was poured into water, and the resulting mixture was extracted with ethyl acetate and then purified by column chromatograph (PE/EA=10/1) to afford the title compound (14.5 g).

$^1$H NMR (400 MHz, CDCl$_3$) δ 4.38-4.40 (m, 1H), 3.86 (dd, J=11.4, 5.6 Hz, 1H), 3.62 (dd, J=11.4, 3.2 Hz, 1H), 2.71 (dd, J=15.6, 5.6 Hz, 1H), 2.48 (dd, J=3.4, 5.6 Hz, 1H), 1.56 (s, 9H), 0.89 (m, 9H), 0.08 (m, 6H).

Step C-13: Synthesis of tert-butyl (2R)-2-((tert-butyldimethylsilyl)oxy)-4-(5-fluoro-2-methoxyphenyl)-4-hydroxybutylcarbamate 5-Fluoro-2-methoxy-bromobenzene (9.75 g) was dissolved in dried tetrahydrofuran and cooled to 0° C., and then thereto was added isopropylmagnesium chloride (2M, 23.5 mL). The reaction system was warmed to 70° C. and stirred for 2 h, and then cooled to 0° C. again. To the reaction system was added a solution of tert-butyl (R)-4-((tert-butyldimethylsilyl)oxy)-2-oxopyrrolidine-1-carboxylate (15.0 g) in tetrahydrofuran, warmed to room temperature again and stirred for 2 h. Methanol and then sodium borohydride (1.78 g) were added, and stirred for 2 h. After completion of the reaction, the reaction was quenched with a saturated ammonium chloride solution. The resulting mixture was extracted with ethyl acetate, and then purified by column chromatography (PE/EA=13/1) to afford the title compound (4.2 g).

Step D-13: Synthesis of tert-butyl (4R)-4-(tert-butyldimethylsilyloxy)-2-(5-fluoro-2-methoxyphenyl)pyrrolidine-1-carboxylate Tert-butyl (2R)-2-((tert-butyldimethylsilyl)oxy)-4-(5-fluoro-2-methoxyphenyl)-4-hydroxybutylcarbamate (4.2 g) was dissolved in dichloromethane and cooled to −60° C., and thereto were added triethylamine (3.95 mL) and methylsulfonyl chloride (0.807 mL) dropwise, and stirred for 1 h while maintaining the same temperature. Then DBU (2.1 mL) was added, and the resulting mixture was warmed to room temperature and continuously stirred for 3 h. After monitoring the completion of the reaction, the reaction system was poured into water, and extracted with dichloromethane (50 mL×3). The organic phase was washed with a saturated saline solution, dried over sodium sulfate, and then purified by column chromatography (PE/EA=15/1) to afford the title compound (3.18 g).

Step E-13: Synthesis of tert-butyl (2R,4R)-2-(5-fluoro-2-methoxyphenyl)-4-hydroxypyrrolidine-1-carboxylate Tert-butyl (4R)-4-(tert-butyldimethylsilyloxy)-2-(5-fluoro-2-methoxyphenyl) pyrrolidine-1-carboxylate (3.18 g) was dissolved in tetrahydrofuran, and then thereto was added tetrabutylammonium fluoride trihydrate (3.5 g) at 0° C., and stirred for 1 h. After monitoring the completion of the reaction, the reaction system was poured into an ice water, and the resulting mixture was extracted with ethyl acetate (×2), and then purified by column chromatography (gradient elution with eluent: PE/EA=20/1-10/1-1/1 (V:V)) to afford the title compound (1.2 g).

Step F-13: Synthesis of (3R,5R)-5-(5-fluoro-2-hydroxyphenyl)pyrrolidin-3-ol

To a solution of tert-butyl (2R,4R)-2-(5-fluoro-2-methoxyphenyl)-4-hydroxypyrrolidine-1-carboxylate (600 mg) in dichloromethane was added a boron tribromide solution (0.746 mL) dropwise at 0° C., warmed to room temperature and stirred overnight. After monitoring the completion of the reaction by LCMS and TLC, the reaction system was poured into an ice water, and then extracted with a mixed solvent of DCM/iPrOH=3/1 (V/V) (150 ml×3). The organic phase was dried over sodium sulfate, and filtered. The solvent was removed from the filtrate to afford (3R,5R)-5-(5-fluoro-2-hydroxyphenyl)pyrrolidin-3-ol (391 mg).

$^1$H NMR (400 MHz, CDCl$_3$) δ 6.83-6.95 (m, 2H), 6.63-6.66 (m, 1H), 4.26-4.33 (m, 2H), 3.32 (s, 1H), 3.01-3.04 (m, 1H), 2.76-2.79 (m, 1H), 2.38-2.45 (m, 1H), 1.55-1.62 (m, 1H).

Step G-13: Synthesis of tert-butyl (2R,4R)-2-(5-fluoro-2-hydroxyphenyl)-4-hydroxypyrrolidine-1-carboxylate To a solution of (3R,5R)-5-(5-fluoro-2-hydroxyphenyl) pyrrolidin-3-ol (391 mg) in dichloromethane were added Boc$_2$O (476 mg) and triethylamine (602 mg) dropwise at room temperature, and stirred overnight at room temperature. After monitoring the completion of the reaction, the solvent was removed and the residue was purified by column chromatography (gradient elution with eluent: PE/EA=3/1-1/1 (V/V)) to afford the title compound (330 mg).

$^1$H NMR (400 MHz, CDCl$_3$) δ 8.60 (s, 1H), 7.16 (s, 1H), 6.72-6.76 (m, 1H), 6.62-6.66 (m, 1H), 5.15 (s, 1H), 4.55 (s, 1H), 3.77-3.81 (m, 1H), 3.53-3.56 (m, 1H), 2.58-2.66 (m, 1H), 2.04-2.15 (m, 1H), 1.41 (s, 9H).

Step H-13: Synthesis of tert-butyl (2R,4S)-4-fluoro-2-(5-fluoro-2-hydroxyphenyl) pyrrolidine-1-carboxylate To a solution of tert-butyl (2R,4R)-2-(5-fluoro-2-hydroxyphenyl)-4-hydroxypyrrolidine-1-carboxylate (330 mg) in dichloromethane was added DAST reagent (359 mg) dropwise at −78° C. and stirred for 2 h while maintaining the same temperature, and then gradually warmed to room temperature and stirred overnight. The reaction was quenched with a saturated sodium bicarbonate solution at 0° C., and the resulting mixture was extracted with dichloromethane (200 ml×2). The organic phase was washed with a saturated saline solution, dried over sodium sulfate and then purified by column chromatography (eluent: PE/EA=7/1 (V/V)) to afford the title compound (145 mg).

$^1$H NMR (400 MHz, CDCl$_3$) δ 6.82-7.02 (m, 1H), 6.62-6.80 (m, 2H), 5.10-5.40 (m, 2H), 3.90-4.20 (m, 2H), 3.81-3.50 (m, 1H), 3.60-3.78 (m, 1H), 2.18-2.6 (m, 1H), 1.35 (s, 9H).

Step 1-13: Synthesis of 4-fluoro-2-((2R,4S)-4-fluoropyrrolidin-2-yl)phenol

To a solution of tert-butyl (2R,4S)-4-fluoro-2-(5-fluoro-2-hydroxyphenyl) pyrrolidine-1-carboxylate (145 mg) in dichloromethane was added a 4 N solution of hydrogen chloride in 1,4-dioxane (3 mL) at room temperature, and stirred for 1 h. After monitoring the completion of the reaction, the solvent was removed to afford 4-fluoro-2-((2R,4S)-4-fluoropyrrolidin-2-yl)phenol (100 mg) without further purification.

Compounds of Examples

Example 1: Synthesis of (1$^3$E,1$^4$E)-1$^2$-amino-3$^5$-fluoro-4-oxa-7-aza-1(5,3)-pyrazolo[1,5-a]pyrimidine-3(3,2)-pyridine-2(1,2)-pyrrolidylcyclooctanephane-8-one

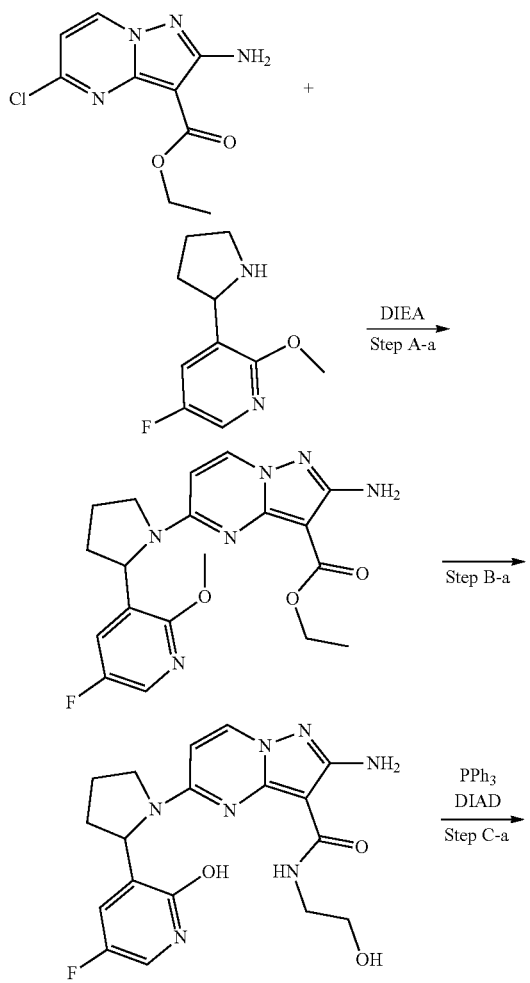

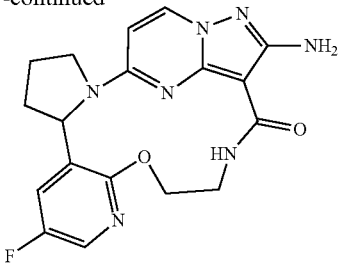

Step A-a: Synthesis of ethyl 2-amino-5-(2-(5-fluoro-2-methoxypyridin-3-yl) pyrrolidin-1-yl)pyrazolo[1,5-a]pyrimidine-3-carboxylate To a solution of ethyl 2-amino-5-chloropyrazolo[1,5-a]pyrimidine-3-carboxylate (3.3 g) and 2-(2-methoxy-5-fluoropyridyl)pyrrolidine (3.0 g) in n-butanol (50 mL) in a reaction tube was added DIEA (5.39 g), and the tube was sealed. The reaction mixture was warmed to 160° C. and reacted for 5 h, cooled to room temperature, and then concentrated under reduced pressure to remove the solvent. The residue was purified by silica gel column chromatography (eluent: petroleum ether:ethyl acetate=4:1 (V:V)) to afford the title compound (5.2 g).

$^1$H NMR (400 MHz, CDCl$_3$) δ7.89-8.07 (m, 2H), 7.04 (s, 1H), 5.63 (s, 1H), 5.22-5.30 (m, 2H), 5.03 (m, 1H), 3.50-4.50 (m, 7H), 2.45 (s, 1H), 1.86-2.04 (m, 3H), 1.40-1.48 (m, 2H), 1.13-1.20 (m, 1H).

Step B-a: Synthesis of 2-amino-5-(2-(5-fluoro-2-hydroxypyridin-3-yl)pyrrolidin-1-yl)-N-(2-hydroxyethyl)pyrazolo[1,5-a]pyrimidine-3-carboxamide To a solution of ethyl 2-amino-5-(2-(5-fluoro-2-methoxypyridin-3-yl)pyrrolidin-1-yl) pyrazolo[1,5-a]pyrimidine-3-carboxylate (600 mg) in n-butanol (3 mL) in a reaction tube was added ethanolamine (4 mL), and the tube was sealed. The reaction mixture was heated to 160° C. and reacted for 16 h, and then concentrated under reduced pressure to remove the solvent. The residue was purified by silica gel column chromatography to afford the title compound (263 mg).

Step C-a: (1$^3$E, 1$^4$E)-1$^2$-amino-3$^5$-fluoro-4-oxa-7-aza-1(5,3)-pyrazolo[1,5-a]pyrimidine-3(3,2)-pyridine-2(1,2)-pyrrolidylcyclooctanephane-8-one To a solution of triphenylphosphine (344 mg) and 2-amino-5-(2-(5-fluoro-2-hydroxypyridin-3-yl)pyrrolidin-1-yl)-N-(2-hydroxyethyl)pyrazolo[1,5-a]pyrimidine-3-carboxamide (263 mg) in tetrahydrofuran (10 mL) was added diisopropyl azodicarboxylate (265 mg) at 0° C., warmed to room temperature and stirred overnight. The reaction mixture was concentrated under reduced pressure to remove the solvent, and the residue was purified by silica gel column chromatography (dichloromethane:methanol=20:1) to afford the title compound (66.0 mg).

$^1$HNMR (400 MHz, CDCl$_3$) δ8.85-8.93 (brs, 1H), 7.99 (d, J=7.6 Hz, 1H), 7.85 (d, J=3.2 Hz, 1H), 7.23 (dd, J=8.4, 2.8 Hz, 1H), 6.02 (d, J=7.2 Hz, 1H), 5.66-5.70 (m, 1H), 5.12-5.21 (brs, 2H), 5.06-5.11 (m, 1H), 4.32-4.38 (m, 1H), 3.83-3.95 (m 2H), 3.64-3.69 (m 2H), 2.35-2.57 (m, 2H), 2.16-2.27 (m, 1H), 1.91-1.99 (m 1H).

The following compounds of Examples were synthesized with reference to the method as shown in Example 1.

| Examples | Structure | Name | ¹HNMR (400 MHz, CDCl$_3$) δ |
|---|---|---|---|
| 2 | 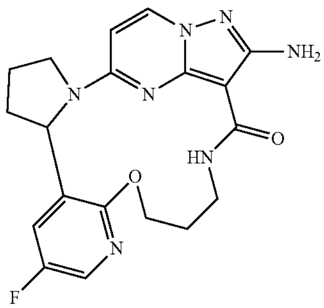 [SMILES: Nc1nn2ccc3nc2c1C(=O)NCCCOc1ncc(F)cc1C1CCCN31] | (1³E,1⁴E)-1²-amino-3⁵-fluoro-4-oxa-8-aza-1(5,3)-pyrazolo[1,5-a]pyrimidine-3(3,2)-pyridine-2(1,2)-pyrrolidylcyclononanephane-9-one | 7.94-7.99 (m, 2H), 7.84 (d, J = 2.8 Hz, 1H), 7.13 (dd, J = 8.4, 3.2 Hz, 1H), 6.02 (d, J = 7.6 Hz, 1H), 5.72-7.76 (m, 1H), 5.34-5.50 (brs, 2H), 5.21-5.26 (m, 1H), 4.16-4.22 (m, 1H), 3.95-4.03 (m, 1H), 3.85-3.91 (m, 1H), 3.61-3.67 (m, 1H), 3.40-3.47 (m, 1H), 2.16-2.48 (m, 4H), 1.97-2.05 (m, 1H), 1.84-1.91 (m, 1H) |
| 3 | 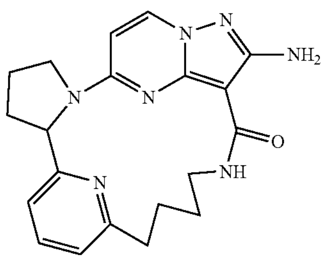 [SMILES: Nc1nn2ccc3nc2c1C(=O)NCCCCc1cccc(n1)C1CCCN31] | (1³E,1⁴E)-1²-amino-4-oxa-8-aza-1(5,3)-pyrazolo[1,5-a]pyrimidine-3(2,6)-pyridine-2(1,2)-pyrrolidylcyclononanephane-9-one | 7.96 (d, J = 8.4 Hz, 1H), 7.51 (t, J = 7.6 Hz, 1H), 7.21 (brs, 1H), 6.72 (d, J = 7.6 Hz, 1H), 6.10 (d, J = 8.0 Hz, 1H), 6.03 (d, J = 7.6 Hz, 1H), 5.55 (t, J = 7.6 Hz, 1H), 5.46 (brs, 2H), 5.05 (d, J = 8.4 Hz, 1H), 4.14-4.09 (m, 1H), 3.94-3.75 (m, 2H), 3.63 (t, J = 7.2 Hz, 1H), 3.42 (brs, 1H), 3.17 (brs, 1H), 2.55-2.49 (m, 1H), 2.41-2.37 (m, 1H), 2.20-2.03 (m, 3H) |
| 4 | 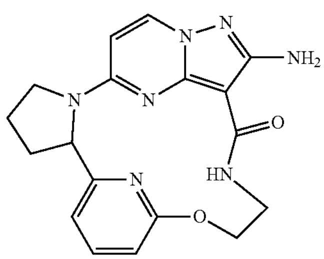 [SMILES: Nc1nn2ccc3nc2c1C(=O)NCCOc1cccc(n1)C1CCCN31] | (1³E,1⁴E)-1²-amino-4-oxa-7-aza-1(5,3)-pyrazolo[1,5-a]pyrimidine-3(2,6)-pyridine-2(1,2)-pyrrolidylcyclooctanephane-8-one | 8.20-8.28 (brs, 1H), 7.97 (d, J = 7.6 Hz, 1H), 7.52 (t, J = 7.6 Hz, 1H), 6.78 (d, J = 7.6 Hz, 1H), 6.59 (d, J = 8.0 Hz, 1H), 6.01 (d, J = 7.6 Hz 1H), 5.92 (td, J = 12.8, 1.2 Hz, 1H), 5.36-5.51 (brs, 2H), 5.07-5.11 (m, 1H), 4.14-4.19 (m, 1H), 3.96-4.04 (m, 1H), 3.81-3.87 (m, 1H), 3.59-3.72 (m, 2H), 2.58-2.66 (m, 1H), 2.39-2.49 (m, 1H), 2.16-2.27 (m, 2H) |
| 5 | 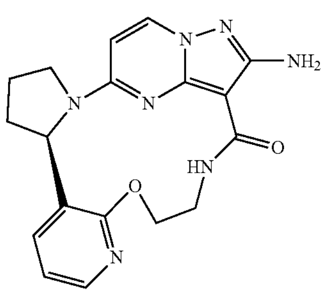 [SMILES: Nc1nn2ccc3nc2c1C(=O)NCCOc1ncccc1[C@H]1CCCN31] | (R,1³E,1⁴E)-1²-amino-4-oxa-7-aza-1(5,3)-pyrazolo[1,5-a]pyrimidine-3(3,2)-pyridine-2(1,2)-pyrrolidylcyclooctanephane-8-one | ¹HNMR (400 MHz, CDCl$_3$) δ 8.96-9.06 (brs, 1H), 8.02 (dd. J = 8.8,2.0 Hz, 1H), 7.96 (d, J = 7.6 Hz, 1H), 7.48 (dd, J = 7.6, 2.0 Hz, 1H), 6.84 (dd, J = 7.6, 4.8 Hz, 1H), 6.00 (d, J = 12 Hz, 1H), 5.74 (dd, J = 8.4, 5.2 Hz, 1H), 5.11-5.17 (brs, 3H), 4.32-4.38 (m, 1H), 3.91-3.98 (m, 1H), 3.83-3.88 (m, 1H), 3.63-3.70 (m, 2H), 2.37-2.55 (m, 2H), 2.14-2.24 (m, 1H), 1.91-1.99 (m. 1H) |

-continued

| Examples | Structure | Name | ¹HNMR (400 MHz, CDCl₃) δ |
|---|---|---|---|
| 6 | 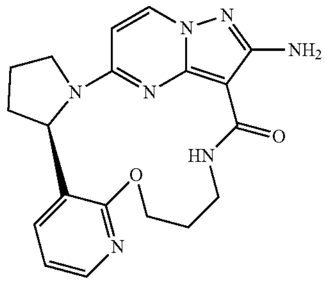 [SMILES: Nc1nn2ccc3nc2c1C(=O)NCCCOc1ncccc1[C@H]1CCCN31] | (R,1³E,1⁴E)-1²-amino-4-oxa-8-aza-1(5,3)-pyrazolo[1,5-a]pyrimidine-3(3,2)-pyridine-2(1,2)-pyrrolidylcyclononanephane-9-one | 8.02-8.08 (brs, 1H), 8.01 (dd, J = 4.8, 2.0 Hz, 1H), 7.97 (d, J = 7.2 Hz, 1H), 7.36 (dd, J = 7.2, 1.6 Hz, 1H), 6.79 (dd, J = 7.2, 4.8 Hz, 1H), 6.00 (d, J = 7.6 Hz, 1H), 5.79-5.82 (m, 1H), 5.39-5.48 (brs, 2H), 5.27-5.32 (m, 1H), 4.16-4.22 (m, 1H), 3.94-4.03 (m, 1H), 3.85-3.91 (m, 1H), 3.62-3.68 (m, 1H), 3.43-3.49 (m, 1H), 2.24-2.44 (m, 4H), 2.01-2.09 (m, 1H), 1.81-1.90 (m, 1H) |
| 7 | 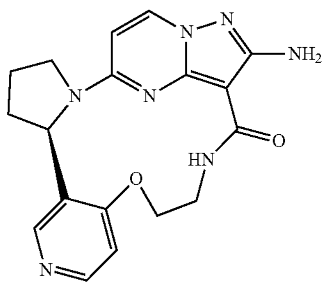 [SMILES: Nc1nn2ccc3nc2c1C(=O)NCCOc1ccncc1[C@H]1CCCN31] | (R,1³E,1⁴E)-1²-amino-4-oxa-7-aza-1(5,3)-pyrazolo[1,5-a]pyrimidine-3(3,2)-pyridine-2(1,2)-pyrrolidylcyclooctanephane-9-one | 9.19 (brs, 1H), 8.40 (s, 1H), 8.34 (d, J = 6.0 Hz, 1H), 7.99 (d, J = 7.6 Hz, 1H), 6.80 (d, J = 5.6 Hz, 1H), 6.03 (d, J = 7.2 Hz, 1H), 5.90-5.86 (m, 1H), 5.15 (brs, 2H), 4.58-4.55 (m, 1H), 4.40-4.36 (m, 1H), 4.02-3.88 (m, 2H), 3.71-3.60 (m, 2H), 2.58-2.45 (m, 2H), 2.26-2.22 (m, 1H), 2.07-1.96 (m, 1H) |
| 8 | 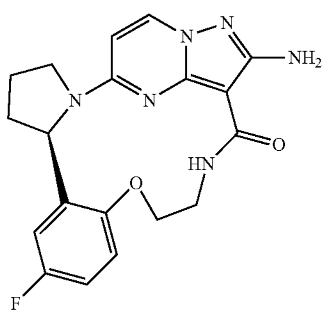 [SMILES: Nc1nn2ccc3nc2c1C(=O)NCCOc1ccc(F)cc1[C@H]1CCCN31] | (R,1³E,1⁴E)-1²-amino-3⁵-fluro-4-oxa-7-aza-1(5,3)-pyrazolo[1,5-a]pyrimidine-2(1,2)-pyrrolidine-3(1,2)-benzocyclooctanephane-8-one | 9.18-9.29 (brs, 1H), 7.98 (d, J = 7.6 Hz, 1H), 6.62-6.88 (m, 3H), 6.03 (d, J = 7.6 Hz, 1H), 5.86-5.89 (m, 1H), 5.13 (s, 2H), 4.47-4.53 (m, 1H), 4.33-4.38 (m, 1H), 3.85-3.91 (m, 2H), 3.60-3.69 (m, 2H), 2.38-2.52 (m, 2H), 2.12-2.23 (m, 1H), 1.89-1.95 (m, 1H) |
| 9 | 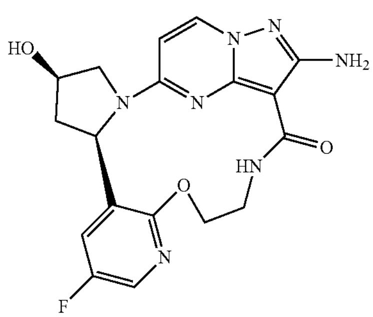 [SMILES: Nc1nn2ccc3nc2c1C(=O)NCCOc1ncc(F)cc1[C@H]1C[C@@H](O)CN31] | (1³E,1⁴E,2²R,2⁴R)-1²-amino-3⁵fluoro-2⁴-hydroxy-4-oxa-7-aza-1(5,3)-pyrazolo[1,5-a]pyrimidine-3(3,2)-pyridine-2(1,2)-pyrrolidylcyclooctanephane-8-one | 8.84-8.87 (brs, 1H), 8.03 (d, J = 7.6 Hz, 1H), 7.85-7.90 (m, 2H), 6.12 (d, J = 7.6 Hz, 1H), 5.77-5.80 (m, 1H), 5.18-5.23 (brs, 2H), 5.09-5.14 (m, 1H), 4.80-4.87 (m, 1H), 4.31-4.38 (m, 1H), 3.82-3.96 (m, 3H), 3.65-3.69 (m, 1H), 2.75-2.83 (m, 1H), 2.07-2.20 (brs, 1H), 2.02-2.08 (m, 1H) |

| Examples | Structure | Name | $^1$HNMR (400 MHz, CDCl$_3$) δ |
|---|---|---|---|
| 10 | 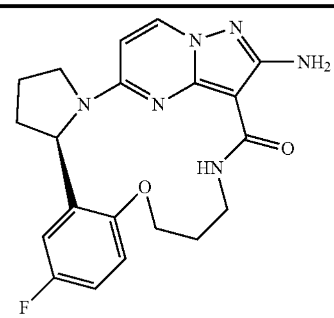 | (R,1$^3$E,1$^4$E)-1$^2$-amino-3$^5$-fluro-4-oxa-8-aza-1(5,3)-pyrazolo[1,5-a]pyrimidine-2(1,2)-pyrrolidine-3(1,2)-benzocyclononanephane-9-one | 8.46-8.64 (brs, 1H), 8.06-8.09 (m, 1H), 6.72-6.95 (m, 3H), 6.08-6.26 (m, 2H), 4.31-4.44 (m, 2H), 3.82-3.99 (m, 4H), 3.38-3.50 (m, 2H), 2.43-2.57 (m, 2H), 2.18-2.34 (m, 2H), 2.02-2.13 (m, 1H), 1.92-1.99 (m, 1H) |
| 11 | 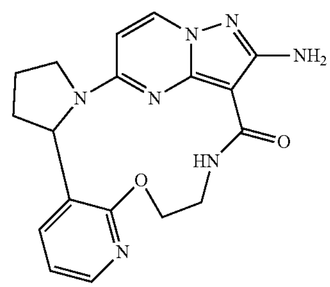 [SMILES: Nc1nn2ccc3nc2c1C(=O)NCCOc1ncccc1C1CCCN31] | (1$^3$E, 1$^4$E)-1$^2$-amino-4-oxa-7-aza-1(5,3)-pyrazolo[1,5-a]pyrimidine-3(3,2)-pyridine-2(1,2)-pyrrolidylcyclooctanephane-8-one | 8.98-9.05 (brs, 1H), 8.03 (dd, J = 4.8, 1.6 Hz, 1H), 7.97 (d, J = 7.6 Hz, 1H), 7.48 (dd, J = 7.6, 1.6 Hz, 1H), 6.85 (dd, J = 7.6, 4.8 Hz, 1H), 6.01 (d, J = 7.6 Hz, 1H), 5.75 (dd, J = 8.0, 5.2 Hz, 1H), 5.12-5.17 (m, 3H), 4.32-4.38 (m, 1H), 3.91-3.99 (m, 1H), 3.83-3.89 (m, 1H), 3.63-3.83 (m, 2H), 2.36-2.58 (m, 2H), 2.15-2.24 (m, 1H), 1.92-1.99 (m, 1H) |

Example 12: (1$^3$E,1$^4$E,2$^2$R,2$^4$S)-1$^2$-Amino-2$^4$,3$^5$-difluoro-4-oxa-8-aza-1(5,3)-pyrazolo[1,5-a]pyrimidin-3(3,2)-pyridine-2(1,2)-pyrrolidylcyclononanephane-9-one

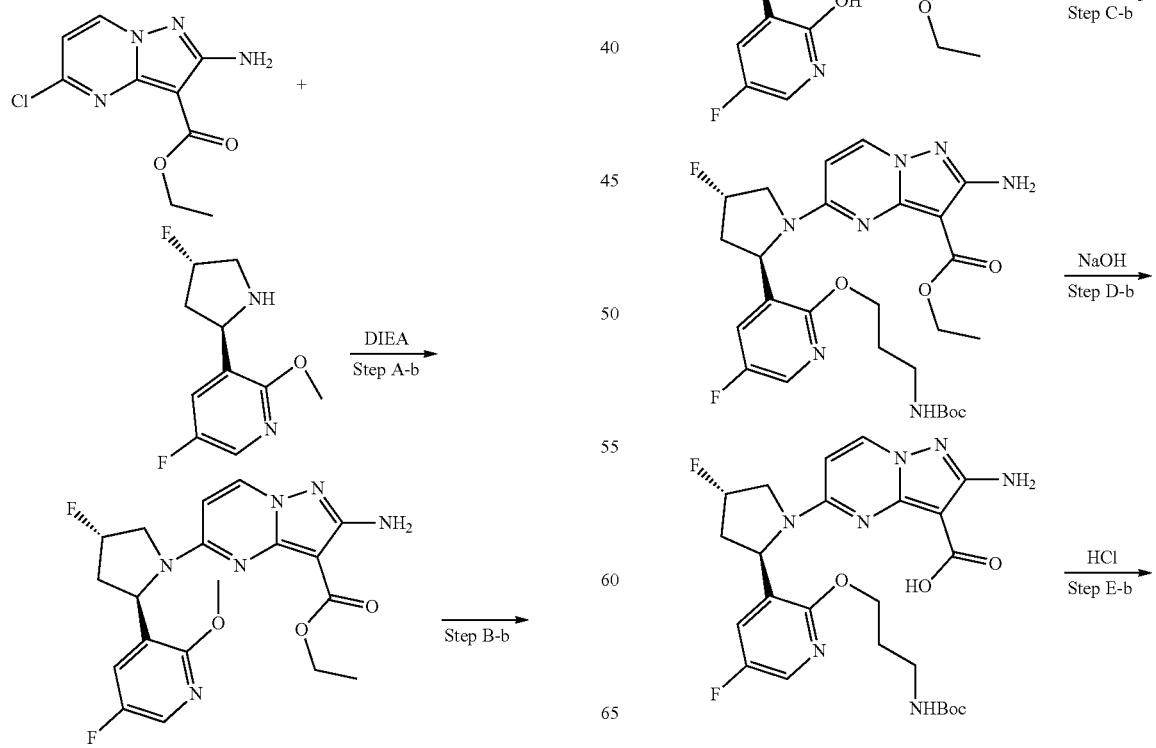

-continued

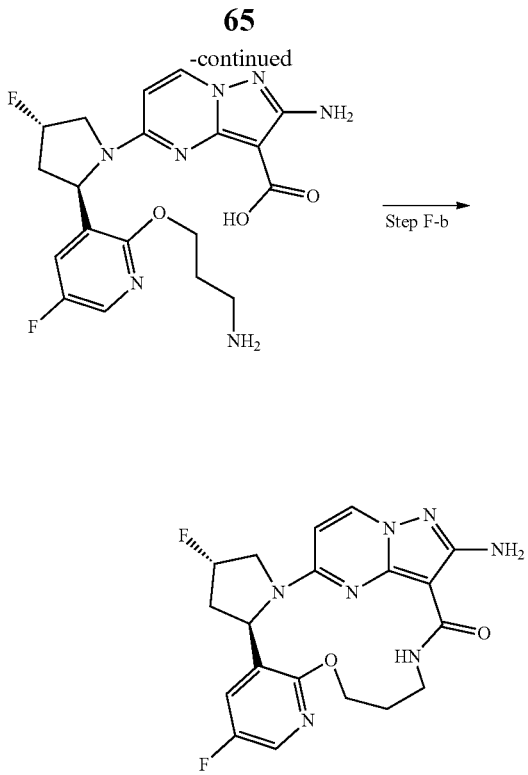

Step F-b →

Step A-b: Synthesis of ethyl 2-amino-5-((2R,4S)-4-fluoro-2-(5-fluoro-2-methoxypyridin-3-yl)pyrrolidin-1-yl)pyrazolo[1,5-a]pyrimidine-3-carboxylate It was carried out with reference to Step A-a in Example 1, but 2-(2-methoxy-5-fluoropyridyl)pyrrolidine was replaced with 5-fluoro-3-((2R,4S)-4-fluoropyrrolidin-2-yl)-2-methoxypyridine.

Step B-b: Synthesis of ethyl 2-amino-5-((2R,4S)-4-fluoro-2-(5-fluoro-2-hydroxypyridin-3-yl)pyrrolidin-1-yl)pyrazolo[1,5-a]pyrimidine-3-carboxylate To ethyl 2-amino-5-((2R,4S)-4-fluoro-2-(5-fluoro-2-methoxypyridin-3-yl)pyrrolidin-1-yl)pyrazolo[1,5-a]pyrimidine-3-carboxylate (1.0 g) was added a solution of HCl in 1,4-dioxane (3.5 M, 4 mL). The reaction mixture was heated to 100° C. and reacted in a sealed tube for 3 h. The reaction mixture was cooled to room temperature and concentrated under reduced pressure to afford the title compound (0.6 g).

Step C-b: Synthesis of ethyl 2-amino-5-((2R,4S)-2-(2-(3-(tert-butoxycarbonylamino) propoxy)-5-fluoropyridin-3-yl)-4-fluoropyrrolidin-1-yl)pyrazolo[1,5-a]pyrimidine-3-carboxylate To a solution of triphenylphosphine (778 mg) in tetrahydrofuran (15 mL) was added diisopropyl azodicarboxylate (600 mg) at 0° C. and stirred for 20 min, and then thereto was added ethyl 2-amino-5-((2R,4S)-4-fluoro-2-(5-fluoro-2-hydroxypyridin-3-yl)pyrrolidin-1-yl)pyrazolo[1,5-a]pyrimidine-3-carboxylate (400 mg). The resulting mixture was warmed to room temperature and stirred overnight, and then concentrated under reduced pressure to remove solvent. The residue was purified by silica gel column chromatography (eluent: dichloromethane:methanol=20:1 (V:V)) to afford the title compound (250 mg).

Step D-b: Synthesis of 2-amino-5-((2R,4S)-2-(2-(3-(tert-butoxycarbonyl)propoxy)-5-fluoropyridin-3-yl)-4-fluoropyrrolidin-1-yl)pyrazolo[1,5-a]pyrimidine-3-carboxylic Acid To a solution of ethyl 2-amino-5-((2R,4S)-2-(2-(3-(tert-butoxycarbonylamino)propyl)-5-fluoropyridin-3-yl)-4-fluoropyrrolidin-1-yl)pyrazolo[1,5-a]pyrimidine-3-carboxylate (375 mg) in methanol (10 mL) was added a saturated aqueous sodium hydroxide solution (2 mL), heated to 80° C. and stirred for 3 h. After removal of methanol, the resulting mixture was adjusted to a pH of less than 5 with diluted hydrochloric acid, and then extracted with a mixed solvent of dichloromethane/isopropanol (V/V=3/1) (50 mL×3). The combined organic phase was dried over anhydrous sodium sulfate and filtered, and the filtrate was concentrated under reduced pressure to afford the title compound (310 mg).

Step E-b: Synthesis of 2-amino-5-((2R,4S)-2-(2-(3-aminopropoxy)-5-fluoropyridin-3-yl)-4-fluoropyrrolidin-1-yl)pyrazolo[1,5-a]pyrimidine-3-carboxylic Acid 2-Amino-5-((2R,4S)-2-(2-(3-(tert-butoxycarbonyl)propyl)-5-fluoropyridin-3-yl)-4-fluoropyrrolidin-1-yl)pyrazolo[1,5-a]pyrimidine-3-carboxylic acid (310 mg) was dissolved in dichloromethane (100 mL), and then thereto was added a solution of HCl in 1,4-dioxane (4M, 30 mL). The resulting mixture was reacted for 10 min, and then concentrated under reduced pressure to afford the title compound (205 mg).

Step F-b: Synthesis of $(1^3E,1^4E,2^2R,2^4S)-1^2$-amino-$2^4,3^5$-difluoro-4-oxa-8-aza-1(5,3)-pyrazolo[1,5-a]pyrimidine-3(3,2)-pyridine-2(1,2)-pyrrolidylcyclononanephane-9-one 2-Amino-5-((2R,4S)-2-(2-(3-aminopropoxy)-5-fluoropyridin-3-yl)-4-fluoropyrrolidin-1-yl)pyrazolo[1,5-a]pyrimidine-3-carboxylic acid (20 mg) was dissolved in DMF (2 mL), and then thereto were added pentafluorophenyldiphenylphosphate (20 mg) and diisopropylethylamine (31 mg) at 0° C. The resulting mixture was warmed to room temperature and stirred overnight. The reaction solution was poured into water (50 mL), and then extracted with ethyl acetate (25 mL×3). The combined organic phase was dried over anhydrous sodium sulfate and filtered, and the filtrate was concentrated under reduced pressure. The residue was purified by silica gel column chromatography (dichloromethane:methanol=20:1) to afford the title compound (8.2 mg).

$^1$HNMR (400 MHz, CDCl$_3$) δ 8.05 (d, J=7.6 Hz, 1H), 7.91-7.98 (m, 1H), 7.86 (d, J=2.8 Hz, 1H), 7.13 (dd, J=8.4, 2.8 Hz, 1H), 6.02 (d, J=7.6 Hz, 1H), 5.83-5.88 (m, 1H), 5.41-5.55 (m, 3H), 5.23-5.28 (m, 1H), 3.97-4.24 (m, 3H), 3.40-3.48 (m, 1H), 2.80-2.91 (m, 1H), 2.26-2.36 (m, 1H), 1.90-2.09 (m, 3H).

The following compounds of Examples were synthesized with reference to the method as shown in Example 12.

| Examples | Structure | Name | ¹HNMR (400 MHz, CDCl₃) δ |
|---|---|---|---|
| 13 | 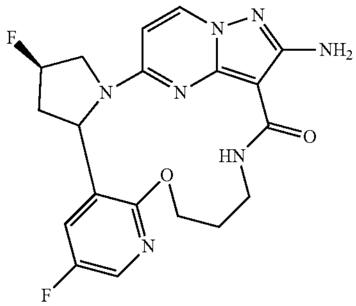 [SMILES: Nc1nn2ccc3nc2c1C(=O)NCCCOc1ncc(F)cc1C1C[C@@H](F)CN31] | (1³E,1⁴E, 2²R,2⁴R)-1²-amino-2⁴,3⁵-difluoro-4-oxa-8-aza-1(5,3)-pyrazolo[1,5-a]pyrimidine-3(3,2)-pyridine-2(1,2)-pyrrolidylcyclononanephane-9-one | 8.15 (d, J = 7.6 Hz, 1H), 7.85 (d, J = 4.0 Hz, 1H), 7.18 (dd, J = 5.6, 3.2 Hz, 1H), 6.31 (d, J = 7.6 Hz, 1H), 5.88-5.90 (m, 1H), 5.59 (dt, J = 53.6, 4.4 Hz, 1H), 5.26-5.31 (s, 1H), 4.19-4.37 (m, 2H), 3.87-4.00 (m, 2H), 3.42-3.44 (m, 1H), 2.74-2.85 (m, 1H), 2.16-2.30 (m, 2H), 1.98-2.04 (m, 1H) |
| 14 | 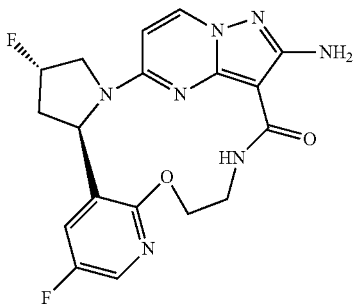 [SMILES: Nc1nn2ccc3nc2c1C(=O)NCCOc1ncc(F)cc1[C@H]1C[C@H](F)CN31] | (1³E,1⁴E,2²R,2⁴S)-1²-amino-2⁴,3⁵-difluoro-4-oxa-7-aza-1(5,3)-pyrazolo[1,5-a]pyrimidine-3(3,2)-pyridine-2(1,2)-pyrrolidylcyclooctanephane-8-one | 8.78 (brs, 1H), 8.10 (d, J = 7.6 Hz, 1H), 7.88 (d, J = 2.8 Hz, 1H), 7.20 (dd, J = 8.4, 2.8 Hz, 1H), 6.03 (d, J = 7.6 Hz, 1H), 5.84 (t, J = 8.0 Hz, 1H), 5.56-5.43 (m, 1H), 5.30 (brs, 2H), 5.15-5.09 (m, 1H), 4.40-4.34 (m, 1H), 4.15-3.90 (m, 3H), 3.67-3.63 (m, 1H), 2.95-2.83 (m, 1H), 2.20-2.03 (m, 1H) |
| 15 | 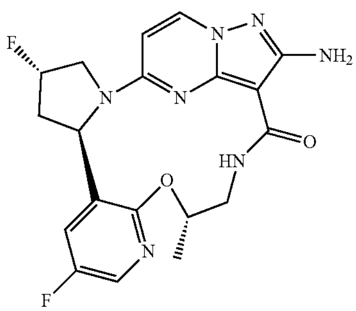 [SMILES: C[C@H]1CNC(=O)c2c(N)nn3ccc(nc23)N2C[C@@H](F)C[C@@H]2c2cc(F)cnc2O1] | (1³E,1⁴E,2²R,2⁴S,5S)-1²-amino-2⁴,3⁵-difluoro-5-methyl-4-oxa-7-aza-1(5,3)-pyrazolo[1,5-a]pyrimidine--3(3,2)-pyridine-2(1,2)-pyrrolidylcyclooctanephane-8-one | 8.95-9.06 (m, 1H), 8.09 (d, J = 7.6 Hz, 1H), 7.87 (d, J = 3.2 Hz, 1H), 7.18 (dd, J = 8.4, 3.2 Hz, 1H), 6.01 (d, J = 7.6 Hz, 1H), 5.82-5.86 (m, 1H), 5.35-5.57 (m, 2H), 5.28 (s, 2H), 3.94-4.15 (m, 3H), 3.26-3.32 (m, 1H), 2.88-2.96 (m, 1H), 2.04-2.22 (m, 1H), 1.52 (d, J = 6.4 Hz, 3H) |
| 16 | 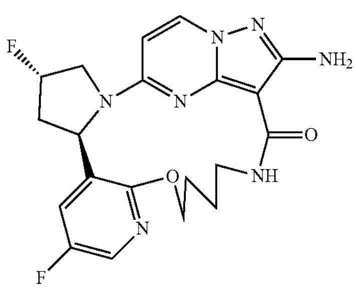 [SMILES: Nc1nn2ccc3nc2c1C(=O)NCCCCOc1ncc(F)cc1[C@H]1C[C@H](F)CN31] | (1³E,1⁴E,2²R,2⁴S)-1²-amino-2⁴,3⁵-difluoro-4-oxa-9-aza-1(5,3)-pyrazolo[1,5-a]pyrimidine-3(3,2)-pyridine-2(1,2)-pyrrolidylcyclodecanephane-10-one | 8.09 (d, J = 7.6 Hz, 1H), 7.88 (d, J = 3.2 Hz, 1H), 7.09-7.16 (brs, 1H), 7.03 (dd, J = 8.4, 2.8 Hz, 1H), 6.08 (d, J = 3.2 Hz, 1H), 5.84 (t, J = 8.0 Hz, 1H), 5.41-5.54 (m, 3H), 5.07-5.11 (m, 1H), 3.96-4.16 (m, 3H), 3.50-3.56 (m, 1H), 3.28-3.35 (m, 1H), 2.93-3.03 (m, 1H), 1.95-2.11 (m, 3H), 1.79-1.88 (m, 2H) |
| 17 | 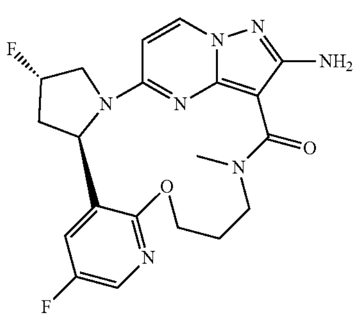 [SMILES: CN1CCCOc2ncc(F)cc2[C@H]2C[C@H](F)CN2c2ccn3nc(N)c(c3n2)C1=O] | (1³E,1⁴E,2²R,2⁴S)-1²-amino-2⁴,3⁵-difluoro-8-methyl-4-oxa-8-aza-1(5,3)-pyrazolo[1,5-a]pyrimidine-3(3,2)-pyridine-2(1,2)-pyrrolidylcyclononanephane-9-one | 8.01 (d, J = 7.6 Hz, 1H), 7.78 (d, J = 3.2 Hz, 1H), 7.06 (dd, J = 8.4, 2.8 Hz, 1H), 5.96 (d, J = 7.2 Hz, 1H), 5.78-5.83 (m, 1H), 5.50 (d, J = 52.4 Hz, 1H), 4.86 (s, 2H), 4.71-4.81 (s, 2H), 4.22-4.28?(m, 1H), 3.90-4.12 (m, 2H), 3.29 (s, 3H), 2.80-2.92 (m, 2H), 1.98-2.31 (m,3H) |

| Examples | Structure | Name | 1HNMR (400 MHz, CDCl3) δ |
|---|---|---|---|
| 18 | 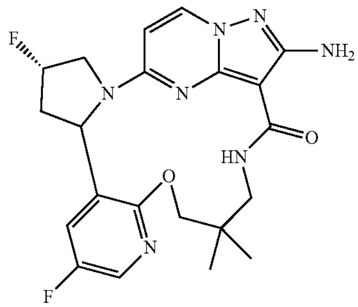 [SMILES: CC1(C)CNC(=O)c2c(N)nn3ccc(nc23)N2C[C@@H](F)CC2c2cc(F)cnc2OC1] | (1³E,1⁴E,2²R,2⁴S)-1²-amino-2⁴,3⁵-difluoro-6,6-dimethyl-4-oxa-8-aza-1(5,3)-pyrazolo[1,5-a]pyrimidine-3(3,2)-pyridine-2(1,2)-pyrrolidylcyclononanephane-9-one | 8.12 (d, J = 12 Hz, 1H), 7.84-7.88 (m, 2H), 7.14 (d, J = 5.2 Hz, 1H), 6.02 (d, J = 7.2 Hz, 1H), 5.80-5.84 (m, 1H), 5.60 (s, 2H), 5.48 (d, J = 52.0 Hz, 1H), 5.35-5.38 (m, 1H), 3.94-4.17 (m, 2H), 3.64-3.68 (m, 2H), 3.4-3.28 (m, 1H), 2.84-2.94 (m, 1H), 1.98-2.14 (m, 1H), 1.30 (s, 3H), 1.07 (s, 3H) |
| 19 | 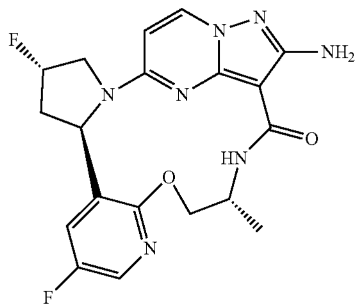 [SMILES: C[C@@H]1COc2ncc(F)cc2[C@H]2C[C@H](F)CN2c2ccn3nc(N)c(c3n2)C(=O)N1] | (1³E,1⁴E,2²R,2⁴S,6R)-1²-amino-2⁴,3⁵-difluoro-6-methyl-4-oxa-7-aza-1(5,3)-pyrazolo[1,5-a]pyrimidine-3(3,2)-pyridine-2(1,2)-pyrrolidylcyclooctanephane-8-one | 9.00 (d, J = 8.8 Hz, 1H), 8.09 (d, J = 7.6 Hz, 1H), 7.87 (d, J = 2.8 Hz, 1H), 7.18 (dd, J = 4.0, 3.2 Hz, 1H), 6.01 (d, J = 7.2 Hz, 1H), 5.83-5.87 (m, 1H), 5.52 (d, J = 52.0 Hz, 1H), 5.30 (s, 2H), 5.15-5.12 (m, 1H), 4.43-4.40 (m, 1H), 3.98-4.15 (m, 3H), 2.93-2.94 (m, 1H), 2.04-2.22 (m, 1H), 1.50 (d, J = 6.8 Hz, 3H) |

Example 20: Synthesis of (S,1³E,1⁴E)-1²-amino-3⁵-fluoro-4-oxa-7-aza-1(5,3)-pyrazolo[1,5-a]pyrimidine-2(1,2)-pyrrolidine-3(1,2)-benzocyclooctanephane-8-one

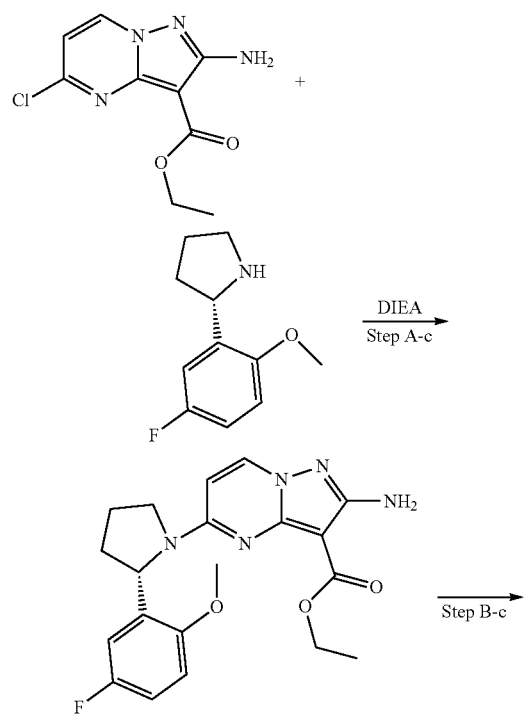

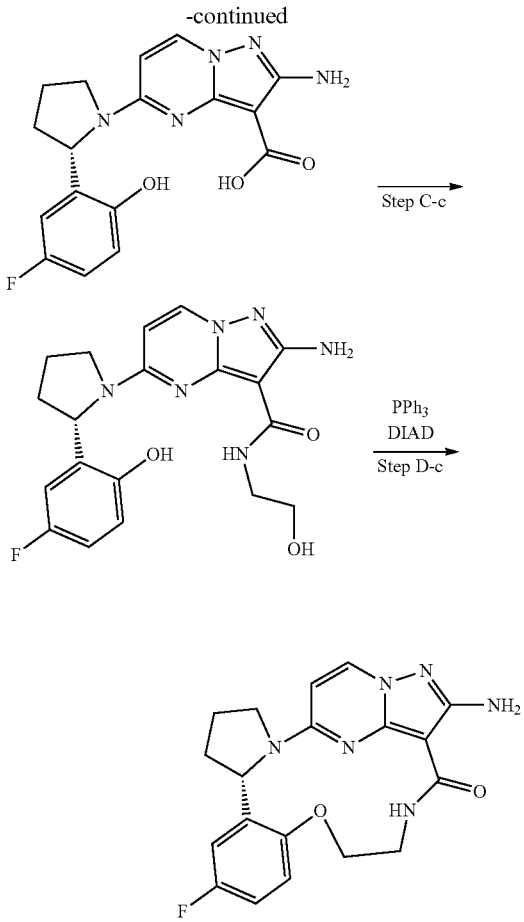

Step A-c: Synthesis of ethyl (S)-2-amino-5-(2-(5-fluoro-2-methoxyphenyl)pyrrolidin-1-yl) pyrazolo[1,5-a]pyrimidine-3-carboxylate Step A-c was carried out with reference to Step A-a in Example 1.

$^1$H NMR (400 MHz, CDCl$_3$) δ 7.81 (d, J=6.4, 1H), 6.91-6.71 (m, 3H), 5.64 (d, J=6.4, 1H), 5.20-5.14 (m, 3H), 4.38 (m, 2H), 4.06-3.94 (m, 2H), 3.88 (s, 3H), 2.44 (m, 1H), 2.05-1.96 (m, 3H), 1.46 (m, 3H).

Step B-c: Synthesis of (S)-2-amino-5-(2-(5-fluoro-2-hydroxyphenyl)pyrrolidin-1-yl) pyrazolo[1,5-a]pyrimidine-3-carboxylic Acid To a solution of ethyl (S)-2-amino-5-(2-(5-fluoro-2-methoxyphenyl)pyrrolidin-1-yl) pyrazolo[1,5-a]pyrimidine-3-carboxylate (160 mg) in dichloromethane (10 mL) was added boron tribromide (193 µL) at 0° C., warmed to room temperature and stirred overnight. The mixture was adjusted to be basic (pH=8) with a saturated aqueous sodium bicarbonate solution and then adjusted to pH=4 with 1 N hydrochloric acid solution, and then was extracted with dichloromethane (50 mL×3). The combined organic phase was dried over anhydrous sodium sulfate and filtered, and the filtrate was concentrated under reduced pressure to afford the title compound (95.3 mg).

Step C-c: Synthesis of (S)-2-amino-5-(2-(5-fluoro-2-hydroxyphenyl)pyrrolidin-1-yl)-N-(2-hydroxyethyl)pyrazolo[1,5-a]pyrimidine-3-carboxamide To a solution of (S)-2-amino-5-(2-(5-fluoro-2-hydroxyphenyl)pyrrolidin-1-yl) pyrazolo[1,5-a]pyrimidine-3-carboxylic acid (160 mg) and ethanolamine (72 mg) in DMF (8 mL) were added EDCI (224 mg), HOBt (158 mg) and triethylamine (272 µL) at 0° C., warmed to room temperature and stirred overnight. Then water (10 mL) was added, and the resulting mixture was extracted with ethyl acetate (50 mL×3). The combined organic phase was washed with a saturated aqueous sodium chloride solution, dried over anhydrous sodium sulfate, and then concentrated under reduced pressure. The residue was purified by silica gel column chromatography (eluent: dichloromethane:methanol=20:1 (V:V)) to afford the title compound (66 mg).

Step D-c: Synthesis of (S,1$^3$E,1$^4$E)-1$^2$-amino-3$^5$-fluoro-4-oxa-7-aza-1(5,3)-pyrazolo[1,5-a]pyrimidine-2(1,2)-pyrrolidine-3(1,2)-benzocyclooctanephane-8-one

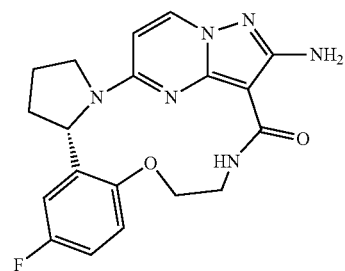 [SMILES: Nc1nn2ccc3nc2c1C(=O)NCCOc1ccc(F)cc1[C@@H]1CCCN31]

Step D-c was carried out with reference to step C-a in Example 1.

$^1$HNMR (400 MHz, CDCl$_3$) δ9.13-9.20 (brs, 1H), 7.92 (d, J=7.6 Hz, 1H), 6.75-6.81 (m, 3H), 5.96 (d, J=7.2 Hz, 1H), 5.80-5.83 (m, 1H), 5.07 (s, 2H), 4.41-4.47 (m, 1H), 4.26-4.31 (m, 1H), 3.78-3.85 (m, 2H), 3.55-3.61 (m, 2H), 2.33-2.43 (m, 2H), 2.08-2.15 (m, 1H), 1.83-1.89 (m, 1H).

Synthesis of Compounds of Example 21 and Example 22

Example 21: (R,1$^3$E,1$^4$E)-1$^2$-Amino-3$^5$-fluoro-4-oxa-8-aza-1(5,3)-pyrazol[1,5-a]pyrimidine-3(3,2)-pyridine-2(1,2)-pyrrolidylcyclononanephane-9-one Example 22: (1$^3$E,1$^4$E,2$^2$R)-1$^2$-Amino-3$^5$-fluoro-3$^1$,3$^2$-dihydro-7-aza-1(5,3)-pyrazolo[1,5-a]pyrimidine-3(3,1)-pyridine-2(1,2)-pyrrolidylcyclooctanephane-3$^2$,8-dione

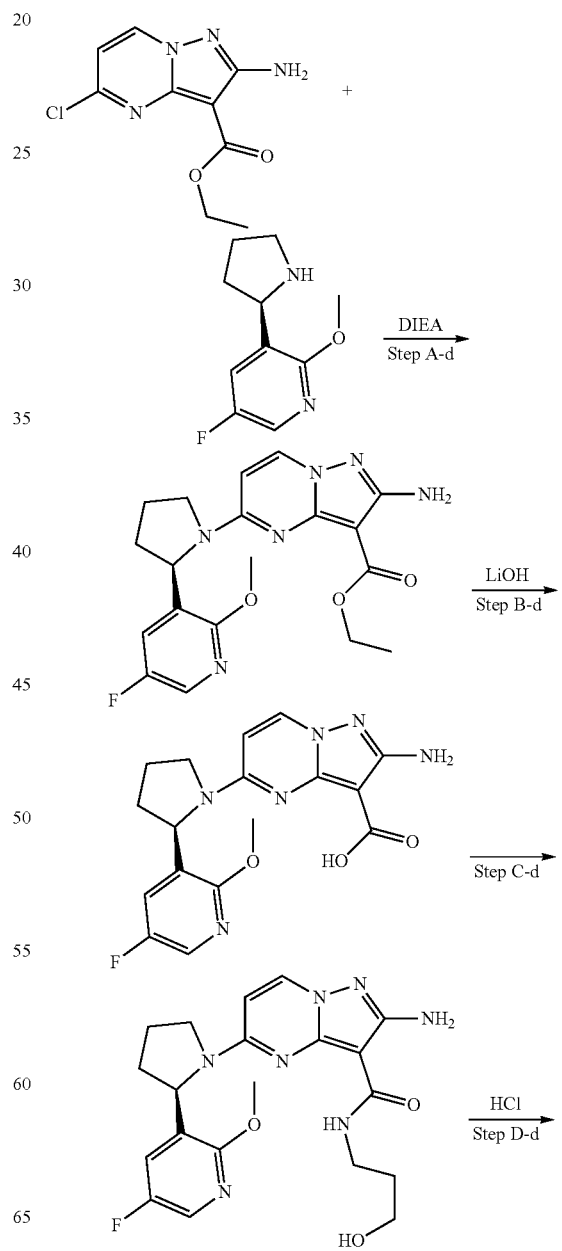

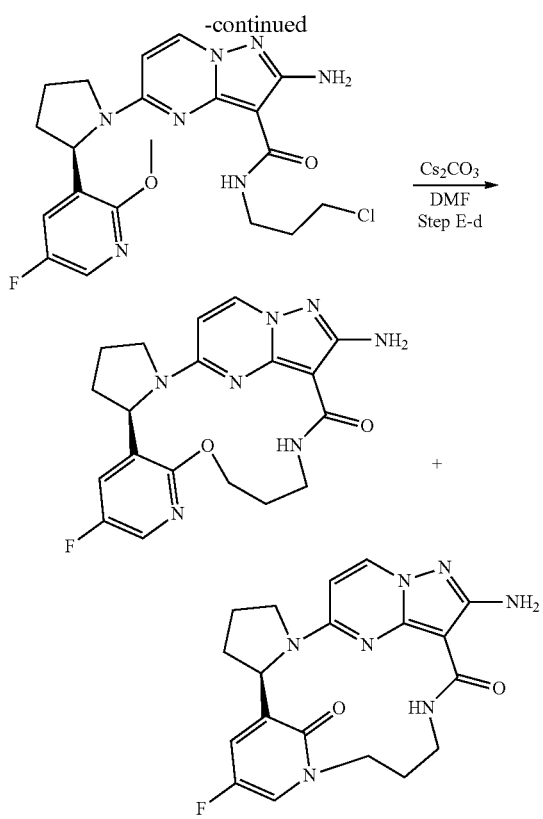

Step A-d: Synthesis of ethyl (R)-2-amino-5-(2-(5-fluoro-2-methoxypyridin-3-yl) pyrrolidin-1-yl)pyrazolo[1,5-a]pyrimidine-3-carboxylate Step A-d was carried out with reference to Step A-a in Example 1.
$^1$H NMR (400 MHz, CDCl$_3$) δ8.20-7.81 (m, 2H), 7.05 (brs, 1H), 6.22-5.48 (m, 1H), 5.23 (brs, 2H), 5.03 (brs, 1H), 4.45-4.26 (m, 1H), 4.20-3.42 (m, 6H), 2.45 (brs, 1H), 2.10-1.81 (m, 3H), 1.45 (brs, 2H), 1.23 (brs, 1H). m/z=401 [M+1]$^+$.

Step B-d: Synthesis of (R)-2-amino-5-(2-(5-fluoro-2-methoxypyridin-3-yl)pyrrolidin-1-yl)pyrazolo[1,5-a]pyrimidine-3-carboxylic Acid To a mixture of ethyl (R)-2-amino-5-(2-(5-fluoro-2-methoxypyridin-3-yl)pyrrolidin-1-yl)pyrazolo[1,5-a]pyrimidine-3-carboxylate (896 mg), water (2 mL) and methanol (10 mL) was added lithium hydroxide monohydrate (500 mg) at room temperature, heated to 80° C. and refluxed for 5 hours. The resulting mixture was concentrated under reduced pressure to remove methanol, and to the residue was added water (20 mL). The resulting mixture was adjusted to pH=2 with 1 N aqueous hydrochloric acid solution, and a large amount of white solid was precipitated out and then filtered. The solid was dried in vacuo to afford the title compound (656 mg).

Step C-d: Synthesis of (R)-2-amino-5-(2-(5-fluoro-2-methoxypyridin-3-yl)pyrrolidin-1-yl)-N-(3-hydroxypropyl)pyrazolo[1,5-a]pyrimidine-3-carboxamide To a solution of (R)-2-amino-5-(2-(5-fluoro-2-methoxypyridin-3-yl) pyrrolidin-1-yl) pyrazolo[1,5-a]pyrimidine-3-carboxylic acid (325 mg) and 3-aminopropanol (100 mg) in dry DMF (9 mL) were sequentially added 1-(3-dimethylaminopropyl)-3-ethyl carbodiimide hydrochloride (502 mg), 1-hydroxybenzotriazole (354 mg) and triethylamine (441 mg) under the protection of nitrogen gas. After completion of the addition, the resulting mixture was stirred at room temperature overnight, and then thereto were added water (20 mL) and ethyl acetate (100 mL), and stirred for 5 min. Then the resulting mixture was layered, and the organic phase was dried over anhydrous sodium sulfate and filtered. The filtrate was concentrated to afford the title compound (137 mg).

Step D-d: Synthesis of (R)-2-amino-N-(3-chloropropyl)-5-(2-(5-fluoro-2-methoxypyridin-3-yl)pyrrolidin-1-yl)pyrazolo[1,5-a]pyrimidine-3-carboxamide A mixture of (R)-2-amino-5-(2-(5-fluoro-2-methoxypyridin-3-yl)pyrrolidin-1-yl)-N-(3-hydroxypropyl)pyrazolo[1,5-a]pyrimidine-3-carboxamide (130 mg) and a solution of HCl in 1,4-dioxane (4 M, 6 mL) was sealed in a pressurized tube, heated to 100° C. and continuously reacted for 1 h. The resulting mixture was cooled to room temperature, and then concentrated under reduced pressure to remove 1,4-dioxane to afford the title compound (110 mg).

Step E-d: Synthesis of (R,1$^3$E,1$^4$E)-1$^2$-amino-3$^5$-fluoro-4-oxa-8-aza-1(5,3)-pyrazolo[1,5-a]pyrimidine-3 (3,2)-pyridine-2(1,2)-pyrrolidylcyclononanephane-9-one and (1$^3$E, 1$^4$E,2$^2$R)-1$^2$-amino-3$^5$-fluoro-3$^1$,3$^2$-dihydro-7-aza-1(5,3)-pyrazolo[1,5-a]pyrimidine-3(3,1)-pyridine-2(1,2)-pyrrolidylcyclooctanephane-3$^2$,8-dione A mixture of (R)-2-amino-N-(3-chloropropyl)-5-(2-(5-fluoro-2-hydroxypyridin-3-yl) pyrrolidin-1-yl)pyrazolo[1,5-a]pyrimidine-3-carboxamide (110 mg), cesium carbonate (414 mg) and DMF (6 mL) was heated to 80° C. and stirred for 6 h, and thereto were added water (20 mL) and ethyl acetate (100 mL) and stirred for 5 min. The resulting mixture was layered, and the organic phase was dried over anhydrous sodium sulfate and filtered. The filtrate was concentrated under reduced pressure, and the residue was purified by silica gel column chromatography (eluent: dichloromethane:methanol=20:1 (V:V)) to afford the two title compounds (15 mg), respectively.

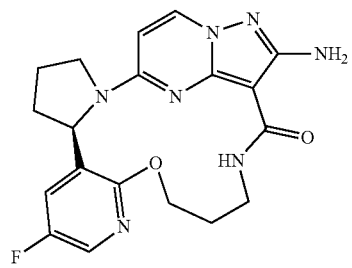 [SMILES: Nc1nn2ccc3nc2c1C(=O)NCCCOc1ncc(F)cc1[C@H]1CCCN31]

$^1$H NMR (400 MHz, CDCl$_3$) δ7.99 (d, J=7.6 Hz, 2H), 7.84 (brs, 1H), 7.14 (d, J=8.4 Hz, 1H), 6.02 (d, J=7.6 Hz, 1H), 5.76-5.74 (m, 1H), 5.41 (brs, 2H), 5.24-5.20 (m, 1H), 4.20 (d, J=8.8 Hz, 1H), 4.02-3.95 (m, 1H), 3.92-3.86 (m, 1H), 3.65 (dd, J=17.2, 7.6 Hz, 1H), 3.46 (t, J=6.8 Hz, 1H), 2.49-2.19 (m, 4H), 2.06-1.95 (m, 1H), 1.90-1.83 (m, 1H). m/z=398[M+1]$^+$.

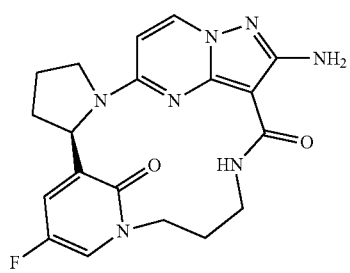 [SMILES: Nc1nn2ccc3nc2c1C(=O)NCCCn1cc(F)cc(c1=O)[C@H]1CCCN31]

$^1$H NMR (400 MHz, CDCl$_3$) δ 7.97 (d, J=7.6 Hz, 1H), 7.37 (brs, 1H), 7.05-6.98 (brs, 2H), 6.01 (d, J=7.6 Hz, 1H), 5.51 (t, J=7.2 Hz, 1H), 5.41 (brs, 2H), 5.07 (t, J=12.4 Hz, 1H), 4.39-4.31 (m, 1H), 3.81-3.65 (m, 2H), 3.43-3.31 (m, 2H), 2.56-2.53 (m, 1H), 2.39-1.98 (m, 3H), 1.94-1.76 (m, 2H). m/z=398[M+1]$^+$.

Example 23: Synthesis of (1$^3$E,1$^4$E,2$^2$R,2$^4$S)-1$^2$-amino-2$^4$,3$^5$-difluoro-3$^1$,3$^2$-dihydro-7-aza-1(5,3)-pyrazolo[1,5-a]pyrimidine-3(3,1)-pyridine-2(1,2)-pyrrolidylcyclooctanephane-3$^2$,8-dione

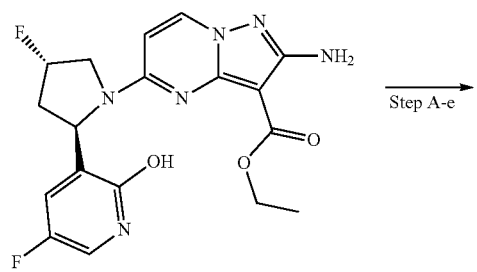

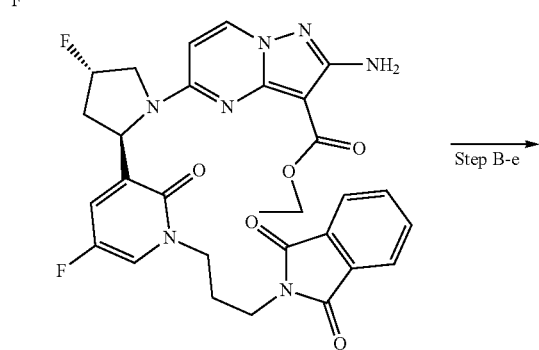

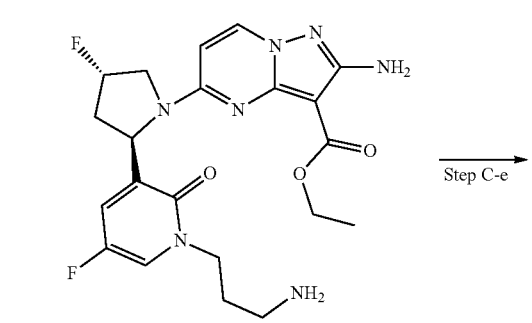

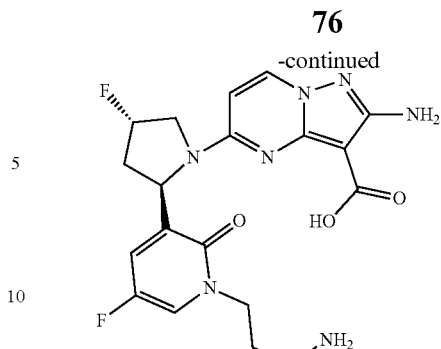

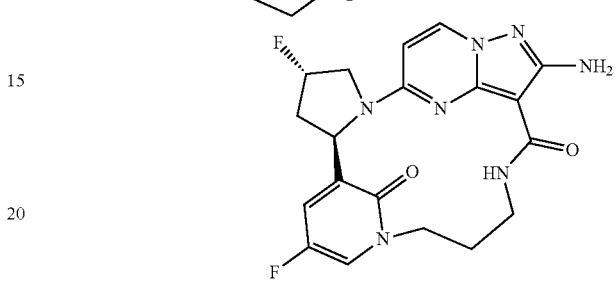

Step A-e: Synthesis of ethyl 2-amino-5-((2R,4S)-2-(1-(3-(1,3-dioxoisoindolin-2-yl)propyl)-5-fluoro-2-oxo-1,2-dihydropyridin-3-yl)-4-fluoropyrrolidin-1-yl)pyrazolo[1,5-a]pyrimidine-3-carboxylate To a solution of ethyl 2-amino-5-((2R,4S)-4-fluoro-2-(5-fluoro-2-hydroxypyridin-3-yl)pyrrolidin-1-yl)pyrazolo[1,5-a]pyrimidine-3-carboxylate (380 mg) in DMF (8 mL) was added lithium hydride (12 mg) at 0° C. and stirred for 5 min, and then thereto was added N-bromopropylphthalamide (500 mg). The resulting mixture was warmed to room temperature and stirred for 4 h. Water (20 mL) was added, and the resulting mixture was extracted with dichloromethane (50 mL×3). The combined organic phase was dried over anhydrous sodium sulfate and filtered. The filtrate was concentrated under reduced pressure to remove the solvent to afford a crude product, which was used into the next step without purification.

Step B-e: Synthesis of ethyl 2-amino-5-((2R,4S)-2-(1-(3-aminopropyl)-5-fluoro-2-oxo-1,2-dihydropyridin-3-yl)-4-fluoropyrrolidin-1-yl)pyrazolo[1,5-a]pyrimidine-3-carboxylate To a solution of ethyl 2-amino-5-((2R,4S)-2-(1-(3-(1,3-dioxoisoindolin-2-yl)propyl)-5-fluoro-2-oxo-1,2-dihydropyridin-3-yl)-4-fluoropyrrolidin-1-yl)pyrazolo[1,5-a]pyrimidine-3-carboxylate (120 mg) in methanol (8 mL) was added hydrazine hydrate (0.5 ml, concentration: 80%) at room temperature, heated to 50° C. and stirred for 5 h. The resulting mixture was concentrated under reduced pressure to remove the solvent to afford a crude product, which was used into the next step without purification.

Step C-e: Synthesis of 2-amino-5-((2R,4S)-2-(1-(3-aminopropyl)-5-fluoro-2-oxo-1,2-dihydropyridin-3-yl)-4-fluoropyrrolidin-1-yl)pyrazolo[1,5-a]pyrimidine-3-carboxylic Acid To a solution of ethyl 2-amino-5-((2R,4S)-2-(1-(3-aminopropyl)-5-fluoro-2-oxo-1,2-dihydropyridin-3-yl)-4-fluoropyrrolidin-1-yl)pyrazolo[1,5-a]pyrimidine-3-carboxylate in methanol (8 mL) was added sodium hydroxide (300 mg) at room temperature, heated to 70° C. and stirred for 1 h. The resulting mixture was adjusted to pH=5 with concentrated hydrochloric acid, and then filtered. The solid was dried to afford a crude product, which was used into the next step without purification.

Step D-e: Synthesis of ($1^3$E,$1^4$E,$2^2$R,$2^4$S)-$1^2$-amino-$2^4$,$3^5$-difluoro-$3^1$,$3^2$-dihydro-7-aza-1(5,3)-pyrazolo[1,5-a]pyrimidine-3(3,1)-pyridine-2(1,2)-pyrrolidylcyclooctanephane-$3^2$,8-dione 2-amino-5-((2R,4S)-2-(1-(3-aminopropyl)-5-fluoro-2-oxo-1,2-dihydropyridin-3-yl)-4-fluoropyrrolidin-1-yl)pyrazolo[1,5-a]pyrimidine-3-carboxylic acid, N,N-diisopropylethylamine, 1-ethyl-(3-dimethylaminopropyl)carbodiimide hydrochloride and 1-hydroxybenzotriazole were dissolved in a mixed solvent of N,N-dimethylformamide and dichloromethane (50 ml, V:V=1:1), and stirred at room temperature for 4 h. After removal of the solvent, the resulting mixture was purified by column chromatography (eluent: dichloromethane:methanol=20:1 (V:V)) to afford the target product (2 mg).

$^1$H NMR (400 MHz, CD$_3$OD) δ8.15 (d, J=7.6 Hz, 1H), 7.62-7.64 (m, 1H), 7.50-7.52 (m, 1H), 7.44-7.46 (m, 1H), 6.29 (d, J=7.6 Hz, 1H), 5.43-5.62 (m, 2H), 4.92-4.98 (m, 1H), 4.11-4.25 (m, 2H), 3.91-4.00 (m, 1H), 3.64-3.68 (m, 1H), 3.30-3.37 (m, 1H), 2.78-2.80 (m, 1H), 2.05-2.23 (m, 2H), 1.78-1.81 (m, 1H). m/z=416[M+1]$^+$.

The following compounds of Examples were synthesized with reference to the method as shown in Example 23.

| Examples | Structure | Name | $^1$HNMR (400 MHz, CDCl$_3$) δ |
|---|---|---|---|
| 24 | 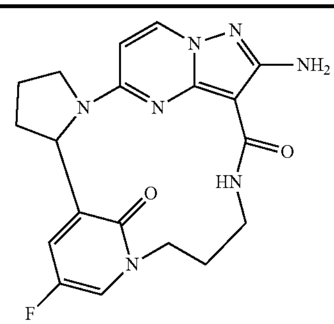 | ($1^3$E,$1^4$E)-$1^2$-amino-$3^5$-fluoro-$3^1$,$3^2$-dihydro-7-aza-1(5,3)-pyrazolo[1,5-a]pyrimidine-3(3,1)-pyridine-2(1,2)-pyrrolidylcyclooctanephane-$3^2$,8-dione | $^1$HNMR (400 MHz, CDCl$_3$) δ8.02 (d, J = 7.2 Hz,1H), 7.37 (d, J = 6.4 Hz, 1H), 7.04 (m, 1H), 6.99 (d, J = 7.2 Hz, 1H), 6.01 (d, J = 7.2 Hz, 1H), 5.49-5.53 (m, 3H), 5.07 (t, J = 11.6 Hz, 1H), 4.30-4.40 (m, 1H), 3.75-3.81 (m, 1H), 3.65-3.70 (m, 1H), 3.32-3.49 (m, 2H), 2.54-2.59 (m, 1H), 2.05-2.28 (m 3H), 1.62-1.94 (m, 2H); m/z = 398[M + 1]$^+$. |
| 25 | 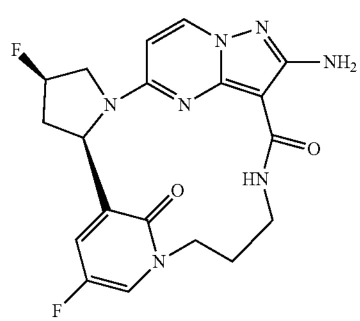 [SMILES: Nc1nn2ccc3nc2c1C(=O)NCCCn1cc(F)cc(c1=O)[C@H]1C[C@@H](F)CN31] | ($1^3$E,$1^4$E,$2^2$R,$2^4$R)-$1^2$-amino-$2^4$,$3^5$-difluoro-$3^1$,$3^2$-dihydro-7-aza-1(5,3)-pyrazolo[1,5-a]pyrimidine-3(3,1)-pyridine-2(1,2)-pyrrolidylcyclooctanephane-$3^2$,8-dione | $^1$H NMR(400 MHz, CD$_3$OD) δ8.15 (d, J = 7.6 Hz, 1H), 7.60-7.62 (m, 1H), 7.48-7.49 (m, 1H), 7.39-7.41 (m, 1H), 6.30 (d, J = 7.6 Hz, 1H), 5.50-5.65 (m, 2H), 4.93-4.99 (m, 1H), 4.18-4.26 (m, 2H), 3.83-3.96 (m, 1H), 3.67-3.69 (m, 1H), 3.30-3.37 (m, 1H), 2.85-2.86 (m, 1H), 2.07-2.32 (m, 2H), 1.74-1.77 (m, 1H); m/z = 416[M + 1]$^+$. |

Example 26: Synthesis of (1³E,1⁴E,2²R,2⁴S,6R)-1²-amino-2⁴,3⁵-difluoro-6-methyl-7-aza-1(5,3)-pyrazol[1,5-a]pyrimidine-3(3,2)-pyridine-2(1,2)-pyrrolidinylcyclooctanephane-8-one

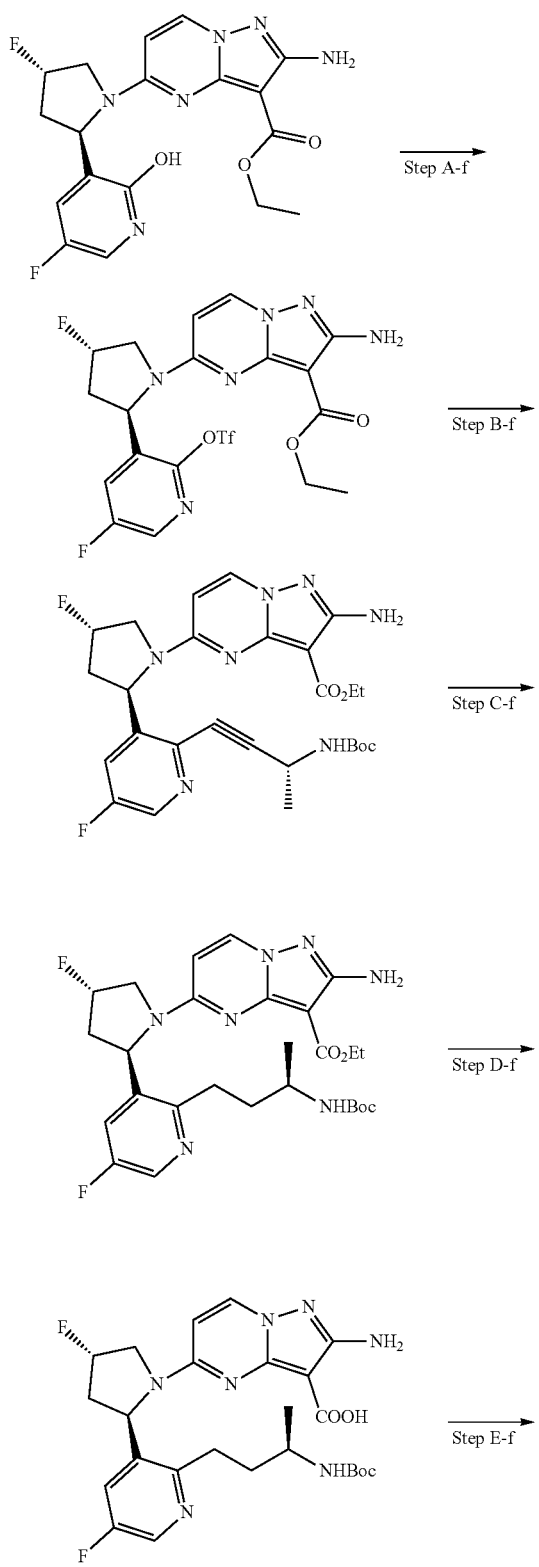

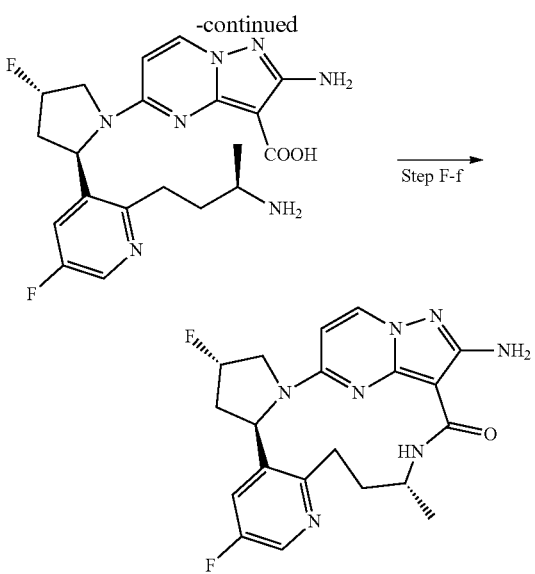

Step A-f: Synthesis of ethyl 2-amino-5-((2R,4S)-4-fluoro-2-(5-fluoro-2-(trifluoromethyl sulfonyloxy)pyridin-3-yl)pyrrolidin-1-yl)pyrazolo[1,5-a]pyrimidine-3-carboxylate To a solution of ethyl 2-amino-5-((2R,4S)-4-fluoro-2-(5-fluoro-2-hydroxypyridin-3-yl)pyrrolidin-1-yl)pyrazolo[1,5-a]pyrimidine-3-carboxylate (1.8 g) and triethylamine (1.43 mL) in DMF (15 mL) was added N-phenylbis(trifluoromethane) sulfonimide (1.76 g), and stirred at room temperature overnight. The reaction was quenched with water (100 mL), and the resulting mixture was extracted with ethyl acetate (50 mL×3). The combined organic phase was dried over anhydrous sodium sulfate and filtered, and the filtrate was concentrated under reduced pressure. The residue was purified by silica gel column chromatography (eluent: dichloromethane:methanol=20:1 (V:V)) to afford the title compound (1.6 g).

Step B-f: Synthesis of ethyl 2-amino-5-((2R,4S)-2-(2-((R)-3-(tert-butoxycarbonylamino)but-1-yn-1-yl)-5-fluoropyridin-3-yl)-4-fluoropyrrolidin-1-yl) pyrazolo[1,5-a]pyrimidine-3-carboxylate To a solution of ethyl 2-amino-5-((2R,4S)-4-fluoro-2-(5-fluoro-2-(trifluoromethyl sulfonyloxy)pyridin-3-yl)pyrrolidin-1-yl)pyrazolo[1,5-a]pyrimidine-3-carboxylate (600 mg) and tert-butyl N-[(1R)-1-methyl-2-propyn-1-yl]carbamate (378 mg) in DMF (8 mL) were added cuprous iodide (43 mg), bis(triphenylphosphine)palladium dichloride (157 mg), and diisopropylethylamine (417 uL) at room temperature under the protection of nitrogen gas, and heated to 65° C. and stirred for 9 h. The resulting mixture was concentrated under reduced pressure to remove DMF, and the residue was purified by silica gel column chromatography (dichloromethane:methanol=20:1) to afford the title compound (563 mg).

¹H NMR (400 MHz, CDCl₃) δ 8.37 (s, 1H), 8.04-8.01 (m, 1H), 7.28-7.23 (m, 1H), 5.80-5.30 (m, 4H), 4.85-4.79 (m, 3H), 4.33 (m, 2H), 4.13-4.10 (m, 2H), 3.05 (m, 1H), 2.05 (m, 1H), 1.54-1.44 (m, 15H). m/z=556[M+1]⁺.

Step C-f: Synthesis of ethyl 2-amino-5-((2R,4S)-2-(2-((R)-3-(tert-butoxycarbonylamino) butyl)-5-fluoropyridin-3-yl)-4-fluoropyrrolidin-1-yl)pyrazolo[1,5-a]pyrimidine-3-carboxylate To a solution of ethyl 2-amino-5-((2R,4S)-2-(2-((R)-3-(tert-butoxycarbonylamino) but-1-yn-1-yl)-5-fluoropyridin-3-yl)-4-fluoropyrrolidin-1-yl)pyrazolo[1,5-a]pyrimidine-3-carboxylate (563 mg) in methanol (100 mL) was added palladium hydroxide on carbon (20%) (860 mg). The resulting mixture was purged with hydrogen gas three times, stirred at room temperature overnight under the protection of hydrogen gas and then suction-filtered. The filtrate was concentrated under reduced pressure to afford the title compound.

Steps D-f, E-f and F-f were carried out with reference to Steps D-b, E-b and F-b in Example 12.

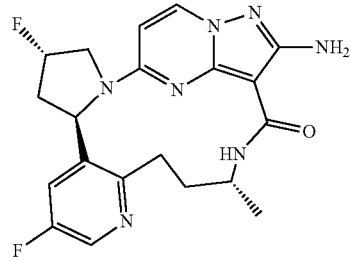 [SMILES: C[C@@H]1CCc2ncc(F)cc2[C@H]2C[C@H](F)CN2c2ccn3nc(N)c(c3n2)C(=O)N1]

$^1$HNMR (400 MHz, CDCl$_3$) δ8.35 (d, J=2.8 Hz, 1H), 8.09 (d, J=7.6 Hz, 1H), 7.43 (d, J=7.2 Hz, 1H), 7.19 (dd, J=9.2, 2.8 Hz, 1H), 6.06 (d, J=7.6 Hz, 1H), 5.62-5.67 (m, 1H), 5.47 (dt, J=52.0, 2.8 Hz, 1H), 5.28-5.39 (brs, 2H), 4.27-4.33 (m, 1H), 3.98-4.18 (m, 2H), 3.67-3.73 (m, 1H), 2.95-3.00 (m, 1H), 2.66-2.84 (m, 2H), 2.32-2.40 (m, 1H), 1.91-2.07 (m, 1H), 1.28 (d, J=6.8 Hz, 3H).

The following compounds of Examples were synthesized with reference to the method as shown in Example 26.

| Examples | Structure | Name | |
|---|---|---|---|
| 27 | 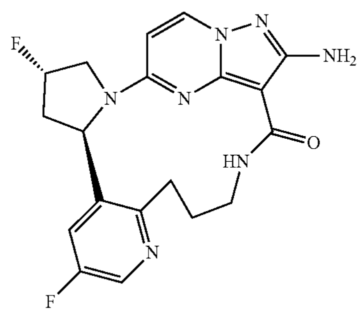 [SMILES: Nc1nn2ccc3nc2c1C(=O)NCCCc1ncc(F)cc1[C@H]1C[C@H](F)CN31] | (1$^3$E,1$^4$E,2$^2$R,2$^4$S)-1$^2$-amino-2$^4$,3$^5$-difluoro-7-aza-1(5,3)-pyrazolo[1,5-a]pyrimidine-3(3,2)-pyridine-2(1,2)-pyrrolidylcyclooctanephane-8-one | $^1$HNMR (400 MHz, CDCl$_3$) δ 8.35 (d, J = 2.8 Hz, 1H), 8.08 (d, J = 7.6 Hz, 1H), 7.66 (d, J = 7.6 Hz, 1H), 7.19 (dd, J = 9.2, 2.8 Hz, 1H), 6.06 (d, J = 7.6 Hz, 1H), 5.62-5.67 (m, 1H), 5.48 (dt, J = 52.0, 2.8 Hz, 1H), 5.23-5.37 (brs, 2H), 3.98-4.18 (m, 2H), 3.84-3.92 (m, 1H), 3.55-3.68 (m, 1H), 3.22-3.30 (m, 1H), 2.91-3.01 (m, 1H), 2.75-2.85 (m, 1H), 2.59-2.69 (m, 1H), 1.93-2.20 (m, 2H) |
| 28 | 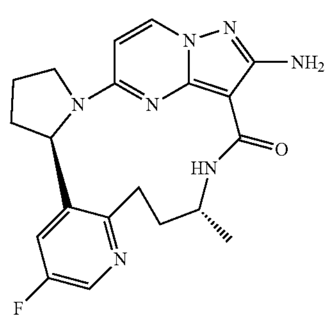 [SMILES: C[C@@H]1CCc2ncc(F)cc2[C@H]2CCCN2c2ccn3nc(N)c(c3n2)C(=O)N1] | (1$^3$E,1$^4$E,2$^2$R,6R)-1$^2$-amino-3$^5$-fluoro-6-methyl-7-aza-1(5,3)-pyrazolo[1,5-a]pyrimidine 3(3,2)-pyridine-2(1,2) pyrrolidylcyclooctanephane-8-one | $^1$HNMR (400 MHz, CDCl$_3$) δ 8.34 (d, J = 2.8 Hz, 1H), 8.05 (d, J = 7.2 Hz, 1H), 7.59 (d, J = 7.2 Hz, 1H), 7.19 (dd, J = 9.6, 2.8 Hz,1H), 6.06 (d, J = 7.6 Hz,1H), 5.45-5.49 (m, 1H), 5.33 (s, 2H), 4.26-4.33 (m, 1H), 3.86-3.92 (m, 1H), 3.63-3.76 (m, 2H), 2.94-2.99 (m, 1H), 2.64-2.71 (m, 1H), 2.44-2.53 (m, 1H), 2.30-2.39 (m, 2H), 2.12-2.22 (m, 1H), 1.77-1.85 (m, 1H), 1.22 (d, J =6.8 Hz, 3H) |

| Examples | Structure | Name | |
|---|---|---|---|
| 29 | 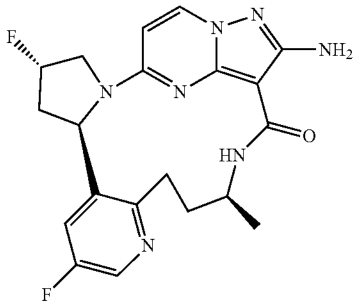 [SMILES: C[C@H]1CCc2ncc(F)cc2[C@H]2C[C@H](F)CN2c2ccn3nc(N)c(c3n2)C(=O)N1] | (1³E,1⁴E,2²R,2₄S,6S)-1²-amino-2⁴,3⁵-difluoro-6-methyl-7-aza-1(5,3)-pyrazolo[1,5-a]pyrimidine-3(3,2)-pyridine-2(1,2)pyrrolidylcyclooctanephane-8-one | 1HNMR (400 MHz, CDCl₃) δ 8.33 (d, J = 2.8 Hz, 1H), 8.06-8.10 (m, 2H), 7.08 (dd, J = 9.2, 2.8 Hz, 1H), 6.04 (d, J = 7.6 Hz, 1H), 5.66-5.71 (m, 1H), 5.50 (dt, J = 52.0, 2.8 Hz, 1H), 5.33 (s, 2H), 4.31-4.46 (m, 1H), 3.98-4.19 (m, 2H), 3.39-3.45 (m, 1H), 2.80-3.01 (m, 3H), 1.94-2.16 (m, 2H), 1.34 (d, J = 6.8 Hz, 3H) |
| 30 | 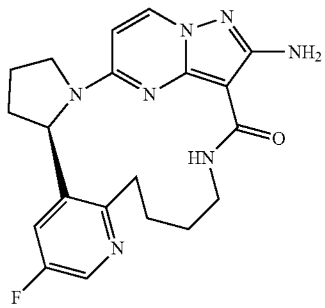 [SMILES: Nc1nn2ccc3nc2c1C(=O)NCCCCc1ncc(F)cc1[C@H]1CCCN31] | (R,1³E,1⁴E)-1²-amino-3⁵-fluoro-8-aza-1(5,3)-pyrazolo[1,5-a]pyrimidine-3(3,2)-pyridine-2(1,2)-pyrrolidylcyclononanephane-9-one | 1HNMR (400 MHz, CDCl₃) δ8.26 (d, J = 2.4 Hz, 1H), 8.08 (d, J = 7.2 Hz, 1H), 7.00 (dd, J = 6.8 2.4 Hz, 1H), 6.12 (d, J = 8.0 Hz, 1H), 5.67-5.65 (m, 1H), 5.30 (brs, 3H), 3.88 (m, 2H), 3.68-3.61 (m, 2H), 3.48-3.25 (m, 3H), 3.16-3.10 (m, 1H), 2.96-2.90 (m, 2H), 2.56-2.51 (m, 2H), 2.30-2.01 (m, 2H) |
| 31 | 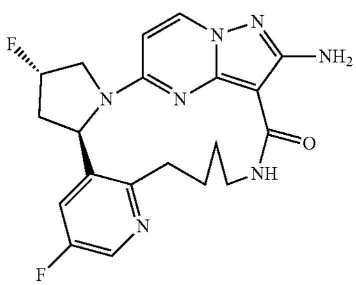 [SMILES: Nc1nn2ccc3nc2c1C(=O)NCCCCc1ncc(F)cc1[C@H]1C[C@H](F)CN31] | (1³E,1⁴E,2²R,2⁴S)-1²-amino-2⁴,3⁵-difluoro-8-aza-1(5,3)-pyrazolo[1,5-a]pyrimidine-3(3,2)-pyridine-2(1,2)-pyrrolidylcyclononanephane-9-one | 1HNMR (400 MHz, CDCl₃) δ8.27 (d, J = 2.8 Hz, 1H), 8.14 (d, J = 7.6 Hz, 1H), 7.12 (s, 1H), 7.06 (dd, J = 9.2, 2.8 Hz, 1H), 6.11 (d, J = 7.6 Hz, 1H), 5.66-5.70 (m, 1H), 5.50 (s, 1H), 5.37 (s, 2H), 4.02-4.12 (m, 2H), 3.44-3.47 (m, 1H), 3.27-3.30 (m, 2H), 2.89-2.97 (m, 2H), 2.18-2.20 (m, 2H), 1.85-2.00 (m, 3H) |

The following compounds of Examples were synthesized with reference to the method as shown in Example 1.

| Examples | Structure | Name | |
|---|---|---|---|
| 32 | 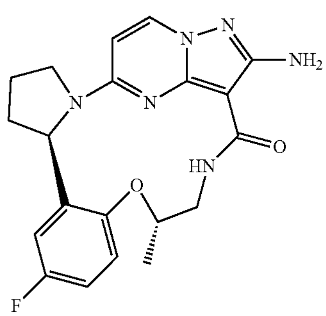 [SMILES: C[C@H]1CNC(=O)c2c(N)nn3ccc(nc23)N2CCC[C@@H]2c2cc(F)ccc2O1] | (1³E,1⁴E,2²R,5S)-1²-amino-3⁵-fluoro-5-methyl-4-oxa-7-aza-1(5,3)-pyrazolo[1,5-a]pyrimidine-(1,2)-pyrrolidine-3(1,2)-benzocyclooctanephane-8-one | ¹HNMR (400 MHz, CDCl₃) δ 9.32 (brs, 0.5H), 8.92 (d, J = 8.0 Hz, 0.5H), 7.98 (d, J = 7.6 Hz, 1H), 6.94-6.75 (m, 3H), 6.03 (d, J = 7.6 Hz, 1H), 5.84 (m, 0.5H), 5.68 (m, 0.5H), 5.12 (brs, 2H), 4.76-4.74 (m, 0.5H), 4.63-4.60 (m, 0.5H), 3.97-3.82 (m, 2H), 3.68-3.64 (m, 1.5H), 3.37-3.33 (m, 0.5H), 2.51-2.34 (m, 2H), 2.20-2.11 (m, 1H), 1.94-1.91 (m, 1H), 1.90 (d, J = 7.2 Hz, 2H), 1.70 (d, J = 7.2 Hz, 1H) |

| Examples | Structure | Name | |
|---|---|---|---|
| 33 | 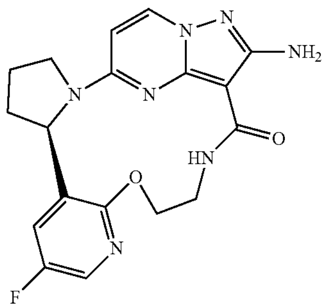 [SMILES: Nc1nn2ccc3nc2c1C(=O)NCCOc1ncc(F)cc1[C@H]1CCCN31] | (R,1³E,1⁴E)-1²-amino-3⁵-fluoro-4-oxa-7-aza-1(5,3)-pyrazo[1,5-a]pyrimidine-3(3,2)-pyridine-2(1,2)-pyrrolidylcyclooctanephane-8-one | ¹HNMR (400 MHz, CDCl₃) δ 8.90 (s, 1H), 8.02 (d, J 6.8 Hz, 1H), 7.85 (s, 1H), 7.24 (dd, J = 8.4 Hz, 3.2 1H), 6.02 (d, J = 7.2 Hz, 1H), 5.68 (t, J = 6.0 Hz, 1H), 5.23 (brs, 2H), 5.10-5.08 (m, 1H), 4.38-4.32 (m, 1H), 3.94-3.83 (m, 2H), 3.70-3.61 (m, 2H), 2.57-2.48 (m, 1H), 2.44-2.37 (m, 1H), 2.25-2.18 (m, 1H), 1.99-1.91 (m, 1H) |

The following compounds of Examples were synthesized with reference to the method as shown in Example 12.

| Examples | Structure | Name | |
|---|---|---|---|
| 34 | 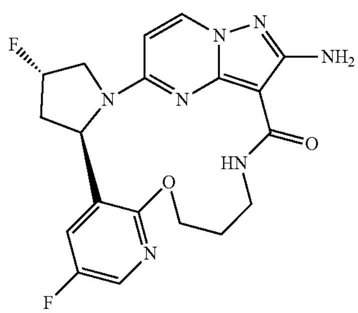 [SMILES: Nc1nn2ccc3nc2c1C(=O)NCCCOc1ncc(F)cc1[C@H]1C[C@H](F)CN31] | (1³E,1⁴E,2²R,2⁴S)-1²-amino-2⁴,3⁵-difluoro-4,7-dioxa-8-aza-1(5,3)-pyrazolo[1,5-a]pyrimidine-3(3,2)-pyridine-2(1,2)-pyrrolidylcyclononanephane-9-one | ¹HNMR (400 MHz, CDCl₃) δ10 .89 (s, 1H), 8.04 (d, J = 7.6 Hz, 1H), 7.85 (s, 1H), 7.15 (dd, J = 6.8 Hz, 2.4 Hz, 1H), 6.03 (d, J = 7.6 Hz, 1H), 5.83 (t, J = 8.0 Hz, 1H), 5.49 (d, J = 52.0 Hz, 1H), 5.26 (brs, 2H), 5.22-5.19 (m, 1H), 4.51-4.47 (m, 2H), 4.44-4.34 (m, 1H), 4.16-3.95 (m, 2H), 2.94-2.92 (m, 1H), 2.11-2.01 (m, 1H) |
| 35 | 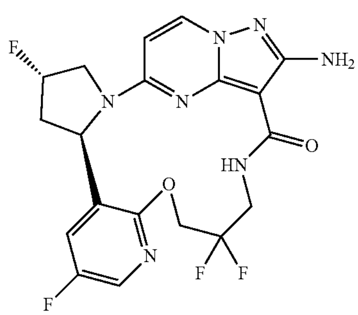 [SMILES: Nc1nn2ccc3nc2c1C(=O)NCC(F)(F)COc1ncc(F)cc1[C@H]1C[C@H](F)CN31] | (1³E,1⁴E,2²R,2⁴S)-1²-amino-2⁴,3⁵,6,6-tetrafluoro-4-oxa-8-aza-1(5,3)-pyrazol[1,5-a]pyrimidine-3(3,2)-pyridine-2(1,2)-pyrrolidylcyclononanephane-9-one | ¹HNMR (400 MHz, CDCl₃) δ 8.10 (d, J = 7.2 Hz, 1H), 7.87 (s, 1H), 7.66-7.69 (m, 1H), 7.21 (d, J = 8.0 Hz, 1H), 6.04 (d, J = 7.2 Hz, 1H), 5.75-5.87 (m, 2H), 5.42-5.51 (m, 3H), 3.94-4.33 (m, 4H), 3.69-3.76 (m, 1H), 2.88-2.92 (m, 1H), 1.95-2.11 (m, 1H) |
| 36 | 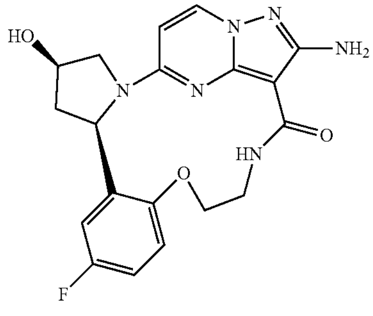 [SMILES: Nc1nn2ccc3nc2c1C(=O)NCCOc1ccc(F)cc1[C@H]1C[C@@H](O)CN31] | (1³E,1⁴E,2²R,2⁴R)-1²-amino-3⁵-fluoro-2⁴-hydroxy-4-oxa-7-aza-1(5,3)-pyrazolo[1,5-a]pyrimidine-2(1,2)-pyrrolidine-3(1,2)-benzocyclooctanephane-8-one | ¹HNMR (400 MHz, CDCl₃) δ 9.12 (s, 1H), 8.04 (d, J = 7.5 Hz, 1H), 7.33 (dd, J = 9.6, 3.1 Hz, 1H), 6.89-6.76 (m, 2H), 6.02 (d, J = 7.5 Hz, 1H), 5.94-5.84 (m, 1H), 5.23 (s, 2H), 4.73-4.76 (m, 1H), 4.54-4.44 (m, 1H), 4.37-4.40 (m, 1H), 3.94-3.79 (m, 3H), 3.63-3.67 (m, 1H), 2.85-2.76 (m, 1H), 2.02-1.97 (m, 1H) |

| Examples | Structure | Name | |
|---|---|---|---|
| 37 | 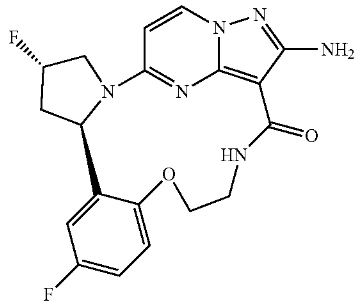 | (1³E,1⁴E,2²R,2⁴S)-1²-amino-2⁴,3⁵-difluoro-4-oxa-7-aza-1(5,3)-pyrazolo[1,5-a]pyrimidine-2(1,2)-pyrrolidine-3(1,2)-benzocyclooctanephane-8-one | ¹HNMR (400 MHz, CDCl₃) δ9.10 (s, 1H), 8.07 (d, J = 7.3 Hz, 1H), 6.91-6.74 (m, 2H), 6.11-5.96 (m, 2H), 5.55 (s, 0.5H), 5.42 (s, 0.5H), 5.22 (s, 2H), 4.49-4.53 (m, 1H), 4.39-4.41 (m, 1H), 3.88-4.12 (m, 3H), 3.63-3.68 (m, 1H), 2.82-2.91 (m, 1H), 2.22-2.14 (m, 1H) |

Bioactivity Assays

Assay for Inhibitory Activity (IC$_{50}$) Against TrkA Kinase

1. Assay for inhibitory activity (IC$_{50}$) against TrkA$^{WT}$

A testing platform for TrkA$^{WT}$ kinase activity was established based on Homogeneous Time-Resolved Fluorescence (HTRF) assay, and the activities of the compounds were tested using the platform. The compounds were subjected to five-fold gradient dilution for eight times with 100% DMSO with a starting concentration of 200 μM (9 concentrations in total). 4 μL of diluted sample for each concentration was added to 96 μL of a reaction buffer (50 mM HEPES, pH7.4, 5 mM MgCl$_2$, 0.1 mM NaVO$_3$, 0.001% Tween-20, 0.01% BSA and 1 mM DTT) and mixed homogeneously to be used as a 4* compound. The reaction buffer was used to formulate 2* TrkA kinase (the final concentration thereof was 1 nM) and 4* substrate (ATP+TK peptide) (TK peptide, HTRF® KinEASE™-TK, was purchased from Cisbio, and the final concentration of TK peptide was 1 μM, and the final concentration of ATP was 40 μM). 2.5 μL of the 4* compound was added to a 384-well plate (OptiPlate-384, purchased from PerkinElmer), and then 5 μL of the 2* TrkA kinase were added, and mixed homogeneously by centrifugation. Then 2.5 μL of the 4* substrate mixture was added to initiate the reaction (the total reaction volume was 10 L). The 384-well plate was placed in an incubator to react for 60 min at 23° C. Then the reaction was terminated by adding 5 μL of Eu3+ cryptate-labeled anti-phosphotyrosine antibody (HTRF® KinEASE™-TK, purchased from Cisbio), and L of Streptavidin-XL-665 (HTRF® KinEASE™-TK, purchased from Cisbio). After incubated for 1 hr in the incubator, the fluorescence values were read out on Envision (purchased from PerkinElmer). The excitation wavelength was 320 nm, and the emission wavelengths for detection were 665 nm and 620 nm. The enzymatic activity was represented by a ratio of the two readout at the two emission wavelengths. The enzymatic activity for each compound was tested at 9 concentrations, and IC$_{50}$ values of the compounds were obtained by calculating the data using GraFit6.0 software (Erithacus Software).

2. Assay for Inhibitory Activity (IC$_{50}$) Against TrkA$^{G667C}$

TrkA$^{G667C}$ (Kinase domain) kinase was expressed in Sf9 cells by using pIEX-Bac-4, and purified by using affinity chromatography on AKTA Purifier (GE company). A testing platform for TrkA$^{G667C}$ kinase activity was established based on Homogeneous Time-Resolved Fluorescence (HTRF) assay, and the activities of the compounds were tested using the platform. The compounds were subjected to five-fold gradient dilution with 100% DMSO with a starting concentration of 200 μM (8 concentrations in total). 4 μL of diluted sample for each concentration was added to 96 μL of a reaction buffer (50 mM HEPES, pH7.4, 5 mM MgCl$_2$, 0.1 mM NaVO$_3$, 0.001% Tween-20, 0.01% BAS, 1 mM DTT) and mixed homogeneously to be used as a 4* compound. The reaction buffer was used to formulate 2*TrkA$^{G667C}$ kinase (the final concentration thereof was 0.5 nM) and 4* substrate (ATP+TK peptide) (TK peptide, HTRF® KinEASE™-TK, was purchased from Cisbio, and the final concentration thereof was 1 μM, and the final concentration of ATP was 15 μM) for use. 2.5 μL of the 4* compound was then added to a 384-well plate (OptiPlate-384, purchased from PerkinElmer), and 5 μL of 2*TrkA$^{G667C}$ kinase was added, and mixed homogeneously by centrifugation. Then 2.5 μL of the 4* substrate mixture was added to initiate the reaction (the total reaction volume was 10 μL). The 384-well plate was placed in an incubator to react for 60 min at 23° C. Then the reaction was terminated by adding 5 μL of Eu3+ cryptate-labeled anti-phosphotyrosine antibody (HTRF® KinEASE™-TK, purchased from Cisbio), and 5 μL of Streptavidin-XL-665 (HTRF® KinEASE™-TK, purchased from Cisbio). After incubated for 60 min in the incubator, the fluorescence values were read out on Envision (purchased from PerkinElmer). The excitation wavelength was 320 nm, and the emission wavelengths for detection were 665 nm and 620 nm. The enzymatic activity was represented by a ratio of the two readout at the two emission wavelengths. The enzymatic activity for each compound was tested at 8 concentrations, and IC$_{50}$ values of the compounds were obtained by calculating the data using GraFit6.0 software (Erithacus Software).

3. Assay for Inhibitory Activity (IC$_{50}$) Against TrkA$^{G595R}$ Kinase

TrkA$^{G595R}$ (Kinase domain) kinase was expressed in Sf9 cells using pIEX-Bac-4, and purified by using affinity chromatography on AKTA Purifier (GE company). A testing platform for TrkA$^{G595R}$ kinase activity was established based on Homogeneous Time-Resolved Fluorescence (HTRF) assay, and the activities of the compounds were tested using the platform. The compounds were subjected to five-fold gradient dilution with 100% DMSO with a starting concentration of 200 μM (8 concentrations in total). 4 μL of diluted sample for each concentration was added to 96 μL of a reaction buffer (50 mM HEPES, pH7.4, 5 mM MgCl$_2$, 0.1 mM NaVO$_3$, 0.001% Tween-20, 0.01% BAS, 1 mM DTT and 50 nM SEB) and mixed homogeneously to be used as a 4* compound. The reaction buffer was used to formulate 2* TrkA$^{G595R}$ kinases (the final concentration was 0.2 nM) and a 4* substrate (ATP+TK peptide) (TK peptide, HTRF® KinEASE™-TK, was purchased from Cisbio and the final concentration thereof was 1 μM, and the final concentration of ATP was 5 M) for use. 2.5 μL of the 4* compound was added to a 384-well plate (OptiPlate-384, purchased from PerkinElmer), and then 5 μL of the 2* TrkA$^{G595R}$ kinases were added, and mixed homogeneously by centrifugation. Then 2.5 μL of the 4* substrate mixture was added to initiate the reaction (the total reaction volume was 10 μL). The 384-well plate was placed in an incubator to react for 120 min at 23° C. Then the reaction was terminated by adding 5 μL of Eu3+ cryptate-labeled anti-phosphotyrosine antibody (HTRF® KinEASE™-TK, purchased from Cisbio), and 5 μL of Streptavidin-XL-665 (HTRF® KinEASE™-TK, purchased from Cisbio). After incubated for 60 min in the incubator, the fluorescence values were read out on Envision (purchased from PerkinElmer). The excitation wavelength was 320 nm, and the emission wavelengths for detection were 665 nm and 620 nm. The enzymatic activity was represented by a ratio of the two readout at the two emission wavelengths. The enzymatic activity for each compound was tested at 8 concentrations, and IC$_{50}$ values of the compounds were obtained by calculating the data using GraFit6.0 software (Erithacus Software).

In the kinase inhibitory activity assays of the present application, "*" means multiplication, and indicates multiples. Illustratively, "2*TrkA$^{G595R}$ kinase (the final concentration thereof is 0.2 nM)" refers to TrkA$^{G595R}$ kinase at a concentration of 0.4 nM.

Exemplary meaning of gradient dilution: for example, "5-fold gradient dilution" means that 4 volumes of a diluent solution was added to 1 volume of a stock solution 1 to obtain a stock solution 2; and then 1 volume of the stock solution 2 was taken and thereto 4 volumes of the diluent solution was added to obtain a stock solution 3.

Solutions having different concentrations were obtained in a similar manner.

The term "TrkA$^{WT}$" refers to a wild-type tropomyosin-like kinase A.

The term "TrkA$^{G667C}$" refers to TrkA$^{WT}$ wherein a glycine at position 667 is mutated to cysteine.

The term "TrkA$^{G595R}$" refers to TrkA$^{WT}$ wherein a glycine at position 595 is mutated to arginine.

The term "HEPES" refers to 4-hydroxyethylpiperazine ethanesulfonic acid.

The term "MgCl$_2$" refers to magnesium chloride.

The term "NaVO$_3$" refers to sodium vanadate.

The term "0.001% Tween-20" means that the volume ratio of Tween 20 to the reaction buffer is 0.001%.

The term "0.01% BAS" refers to a mass-to-volume ratio of bovine serum albumin to the reaction buffer, such as 0.01 g of BSA in 100 mL of the buffer.

The term "DTT" refers to dithiothreitol.

The term "SEB" refers to an additive in an enzymatic reaction buffer.

"Mm" refers to millimoles per liter.

The compounds prepared in the above Examples were analyzed according to the biological methods described in the present application, and the results were shown in Table 1:

TABLE 1

Inhibitory activity (IC$_{50}$) of compounds against a wild-type and mutant-type TrkA kinases

| Example Nos. | TrkA$^{WT}$ IC$_{50}$ (nM) | TrkA$^{G667C}$ IC$_{50}$ (nM) | TrkA$^{G595R}$ IC$_{50}$ (nM) |
|---|---|---|---|
| 1 | 0.80 ± 0.16 | 1.68 ± 0.28 | — |
| 2 | 0.57 ± 0.10 | 1.86 ± 0.49 | — |
| 3 | 0.84 ± 0.12 | 16.2 ± 2.5 | — |
| 5 | 0.37 ± 0.04 | 12.1 ± 1.0 | — |
| 6 | 0.47 ± 0.26 | 5.61 ± 0.67 | — |
| 8 | 0.41 ± 0.04 | 1.63 ± 0.11 | 2.08 ± 0.45 |
| 9 | 0.44 ± 0.12 | 5.74 ± 1.14 | 0.84 ± 0.14 |
| 10 | 0.80 ± 0.21 | 2.41 ± 0.19 | 1.92 ± 0.10 |
| 11 | 1.04 ± 0.34 | 17.4 ± 2.5 | — |
| 12 | 0.72 ± 0.04 | 0.88 ± 0.11 | 0.34 ± 0.04 |
| 13 | 0.64 ± 0.02 | 14.6 ± 1.5 | — |
| 14 | 0.68 ± 0.03 | 0.12 ± 0.01 | 0.40 ± 0.05 |
| 15 | 0.45 ± 0.18 | 0.22 ± 0.02 | 0.53 ± 0.08 |
| 16 | 0.51 ± 0.05 | 0.55 ± 0.08 | 0.76 ± 0.14 |
| 17 | 0.61 ± 0.06 | 8.07 ± 1.24 | 1.05 ± 0.16 |
| 18 | — | 0.40 ± 0.04 | 1.24 ± 0.15 |
| 19 | — | 0.38 ± 0.04 | 0.73 ± 0.07 |
| 20 | 3.8 ± 0.21 | 15.1 ± 1.6 | — |
| 21 | 0.40 ± 0.04 | 1.71 ± 0.19 | 0.85 ± 0.04 |
| 22 | 0.57 ± 0.03 | 12.8 ± 1.4 | — |
| 23 | 0.23 ± 0.03 | 2.39 ± 0.40 | 1.40 ± 0.05 |
| 24 | 0.85 ± 0.07 | 16.0 ± 2.9 | — |
| 26 | 0.23 ± 0.02 | 1.22 ± 0.11 | 0.68 ± 0.17 |
| 27 | 0.21 ± 0.03 | 1.89 ± 0.20 | 0.68 ± 0.26 |
| 28 | 0.31 ± 0.03 | 13.42 ± 1.34 | 1.01 ± 0.36 |
| 29 | 0.25 ± 0.02 | 3.16 ± 0.39 | 1.08 ± 0.24 |
| 31 | — | 2.43 ± 0.39 | 1.45 ± 0.11 |
| 32 | — | 0.43 ± 0.06 | 1.28 ± 0.05 |
| 33 | — | 1.46 ± 0.19 | — |
| 34 | — | 0.82 ± 0.04 | — |
| 35 | — | 0.36 ± 0.02 | 1.36 ± 0.02 |
| 36 | — | 8.16 ± 1.64 | — |
| 37 | — | 0.21 ± 0.02 | — |

Wherein "—" indicates undetermined.

Pharmacokinetic Assay

Male SD rats were available from Beijing Vital River Laboratory Animal Technology Co., Ltd. The rats were allocated with three rats per group, and orally administered the suspension of a sample to be tested (5 mg/kg, the suspension is a mixed solution of 10% EtOH, 40% PEG 400 and 50% H$_2$O) by single intragastric administration, respectively. Before the experiment, the animals were fasted overnight, and the fasting time was from 10 hrs before administration to 4 hrs after administration. After administration, a blood sample was taken at 0.25 hr, 0.5 hr, 1 hr, 2 hrs, 4 hrs, 6 hrs, 8 hrs and 24 hrs, respectively. After the animals were narcotized with isoflurane using an anaesthesia machine for small animals, 0.3 mL of whole blood was taken from fundus venous plexus, and placed in a heparin anticoagulant tube. At 4° C., the sample was centrifuged at 4000 rpm for 5 min, and plasma was transferred to a centrifuge tube and preserved at −80° C. until the analysis was started. The sample in plasma was extracted by the protein precipitation method, and the extracted liquid was analyzed by LC/MS/MS. The results were shown in Table 2.

TABLE 2

Pharmacokinetic Data of compounds of Examples

| Compounds of Examples | 14 | 15 | 33 |
|---|---|---|---|
| dose (mg/kg) | 5 | 5 | 5 |
| T$_{1/2}$(hr) | 1.81 | 1.53 | 4.22 |
| Tmax(hr) | 1.0 | 0.58 | 0.50 |
| Cmax (ng/mL) | 140 | 285 | 142 |
| AUC0-inf(hr*ng/mL) | 504 | 494 | 513 |

What is claimed is:

1. A compound of Formula (I)

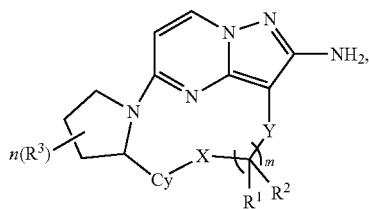

Formula (I)

or a pharmaceutically acceptable salt thereof, wherein
X is selected from the group consisting of a bond, —O—, —S—, and —NR$^4$—;
Y is selected from the group consisting of

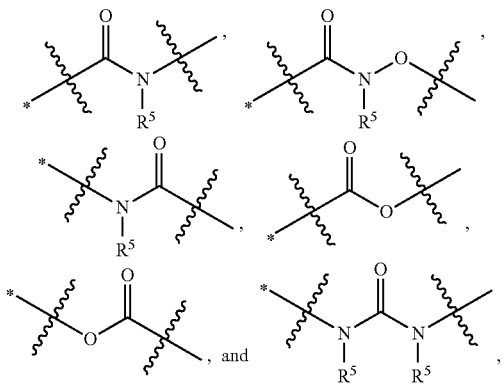

wherein "*" represents the end of the Y group attached to the aminopyrazolopyrimidine ring;

R$^1$ and R$^2$ are independently selected from the group consisting of hydrogen, C$_1$-C$_6$ alkyl, C$_1$-C$_6$ alkoxy, halo, nitro, hydroxy, cyano and amino, wherein C$_1$-C$_6$ alkyl and C$_1$-C$_6$ alkoxy are optionally substituted with one or more substituents independently selected from the group consisting of halo, nitro, hydroxy, cyano and amino; or R$^1$ and R$^2$ are taken together to form (=O) or (=S);

R$^3$ is selected from the group consisting of C$_1$-C$_6$ alkyl, C$_1$-C$_6$ alkoxy, halo, nitro, hydroxy, cyano and amino, wherein C$_1$-C$_6$ alkyl and C$_1$-C$_6$ alkoxy are optionally substituted with one or more substituents independently selected from the group consisting of halo, nitro, hydroxy, cyano and amino;

R$^4$ and R$^5$ are independently selected from the group consisting of hydrogen and C$_1$-C$_6$ alkyl;

m is selected from 0, 1, 2, 3, 4, 5 or 6;

n is selected from 0, 1, 2, 3, 4, 5, 6 or 7;

Cy is selected from the group consisting of a 6- to 10-membered aromatic ring, a 5- to 10-membered aromatic heterocycle, a 3- to 10-membered aliphatic heterocycle, and a 3- to 10-membered cycloalkyl ring, wherein the 6- to 10-membered aromatic ring, 5- to 10-membered aromatic heterocycle, 3- to 10-membered aliphatic heterocycle, or 3- to 10-membered cycloalkyl ring is optionally substituted with one or more substituents independently selected from the group consisting of C$_1$-C$_6$ alkyl, C$_1$-C$_6$ alkoxy, (=O), halo, nitro, hydroxy, cyano, and amino.

2. The compound according to claim 1, wherein X is selected from the group consisting of a bond and —O—.

3. The compound according to claim 1, wherein Y is selected from the group consisting of

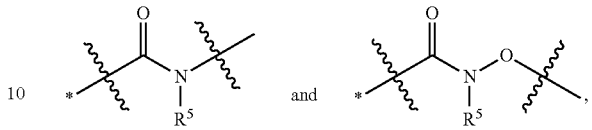

wherein "*" represents the end of the Y group attached to the aminopyrazolopyrimidine ring.

4. The compound according to claim 1, wherein R$^5$ is selected from the group consisting of hydrogen and C$_1$-C$_3$ alkyl.

5. The compound according to claim 1, wherein R$^1$ and R$^2$ are independently selected from the group consisting of hydrogen, C$_1$-C$_3$ alkyl, C$_1$-C$_3$ alkoxy, fluoro, chloro, bromo, iodo, nitro, hydroxy, cyano, and amino, wherein C$_1$-C$_3$ alkyl and C$_1$-C$_3$ alkoxy are optionally substituted with one or more substituents independently selected from the group consisting of fluoro, chloro, bromo, iodo, nitro, hydroxy, cyano, and amino.

6. The compound according to claim 1, wherein m is selected from 1, 2, 3, 4, or 5.

7. The compound according to claim 1, wherein R$^3$ is selected from the group consisting of C$_1$-C$_3$ alkyl, C$_1$-C$_3$ alkoxy, fluoro, chloro, bromo, iodo, nitro, hydroxy, cyano, and amino, wherein C$_1$-C$_3$ alkyl and C$_1$-C$_3$ alkoxy are optionally substituted with one or more substituents independently selected from the group consisting of fluoro, chloro, bromo, iodo, nitro, hydroxy, cyano, and amino.

8. The compound according to claim 1, wherein n is selected from 0, 1, 2, or 3.

9. The compound according to claim 1, wherein, Cy is selected from the group consisting of benzene ring, naphthalene ring, pyrrole, furan, thiophene, imidazole, oxazole, pyrazole, pyridine, pyrimidine, pyrazine, quinoline, isoquinoline, benzofuran, benzothiophene, indole, isoindole, oxirane, tetrahydrofuran, dihydrofuran, pyrrolidine, dihydropyrrolidine, 2H-pyridine, piperidine, piperazine, pyrazolidine, tetrahydropyran, morpholine, thiomorpholine, tetrahydrothiophene, cyclopropane, cyclopentane, and cyclohexane, each of which is optionally substituted with one or more substituents independently selected from the group consisting of C$_1$-C$_3$ alkyl, C$_1$-C$_3$ alkoxy, (=O), fluoro, chloro, bromo, iodo, nitro, hydroxy, cyano, and amino.

10. The compound according to claim 1, wherein the compound of Formula (I) is a compound represented by Formula (II),

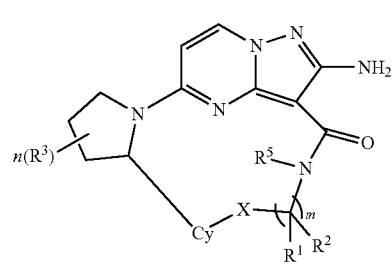

Formula (II)

wherein X, R¹, R², R³, R⁵, Cy, m and n are as defined in claim 1.
11. The compound according to claim 1, wherein the compound of Formula (I) or a pharmaceutically acceptable salt thereof is selected from the group consisting of
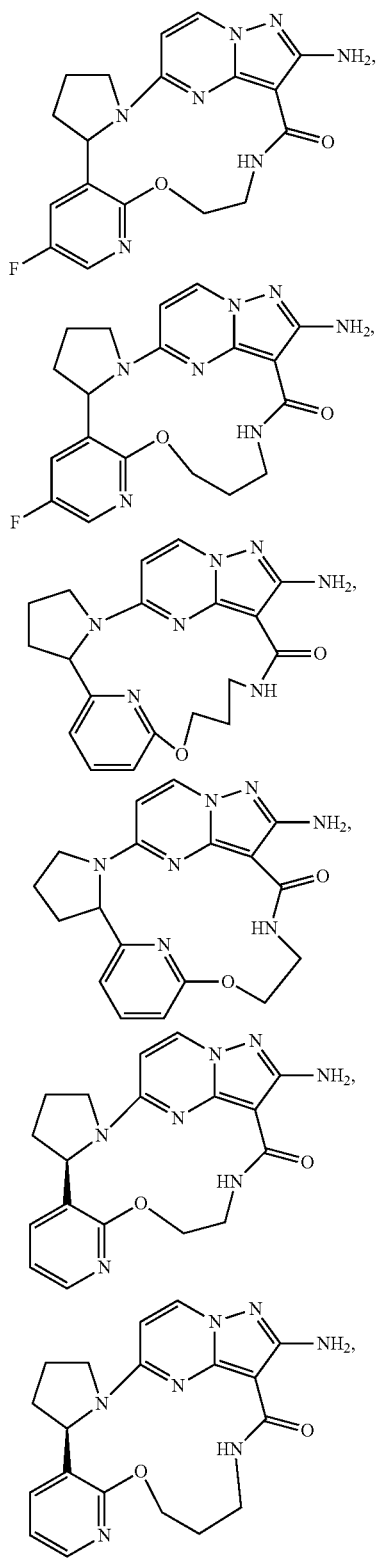
-continued
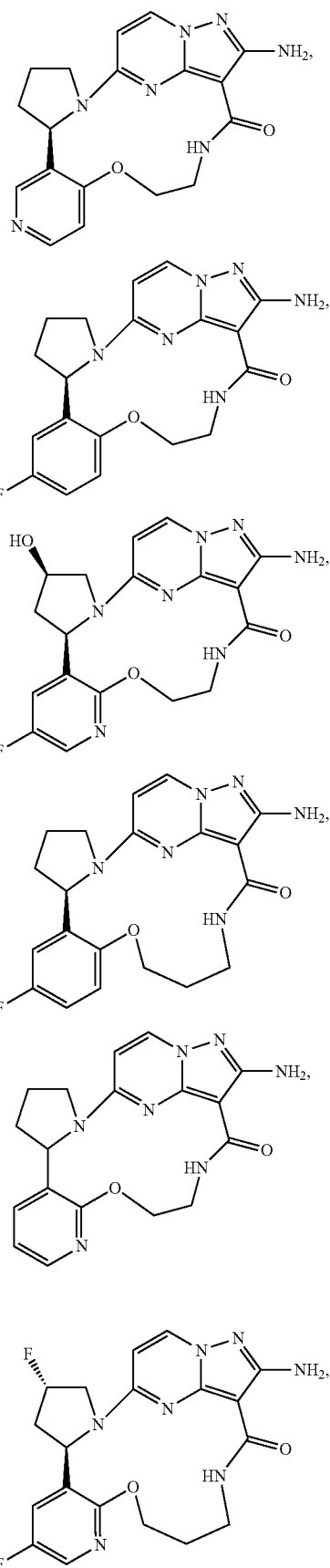

95
-continued
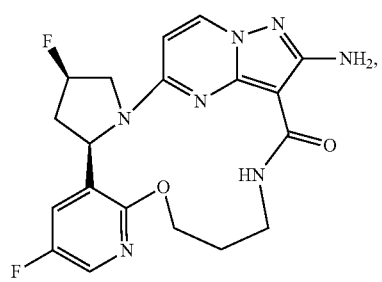
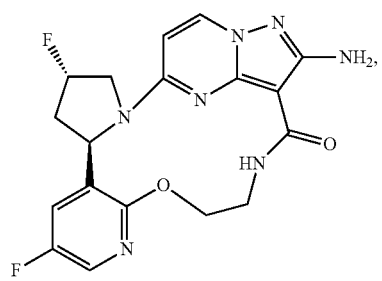
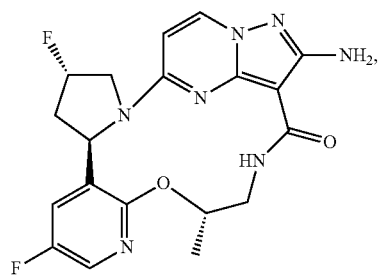
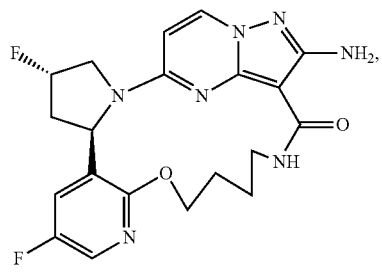
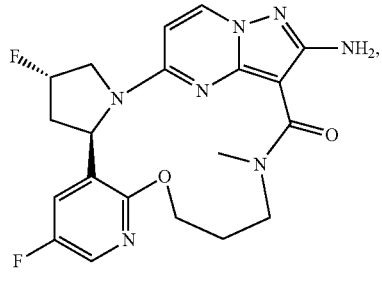
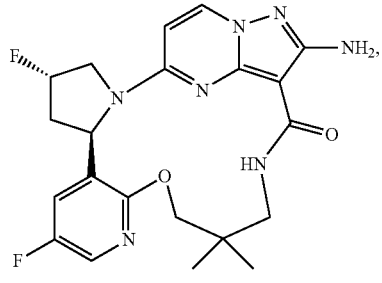
96
-continued
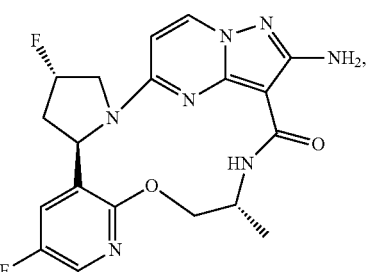
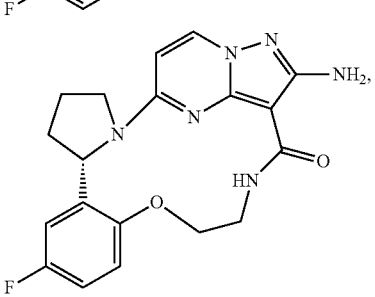
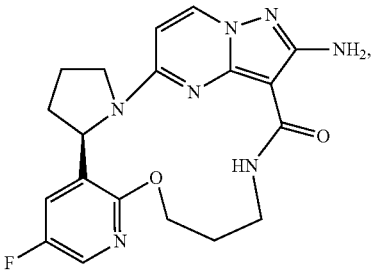
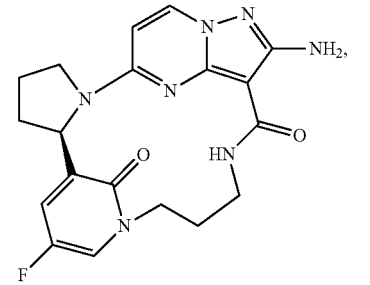
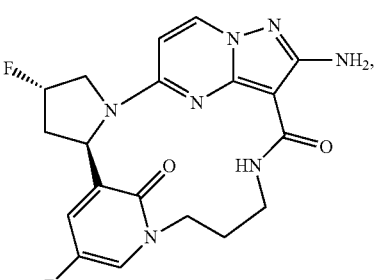
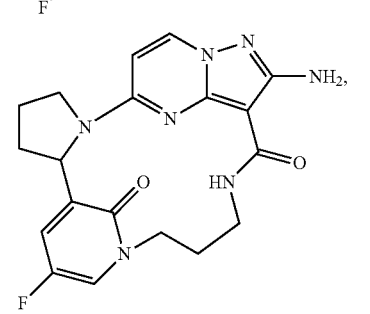

-continued
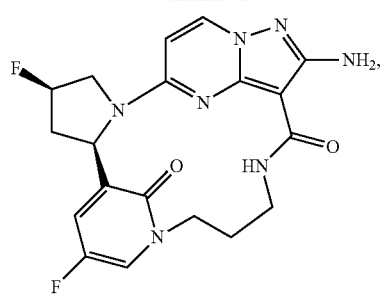
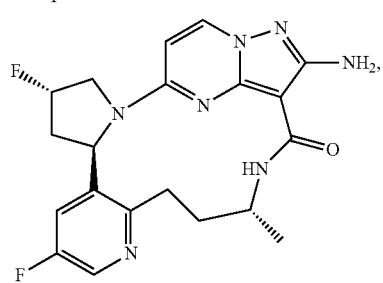
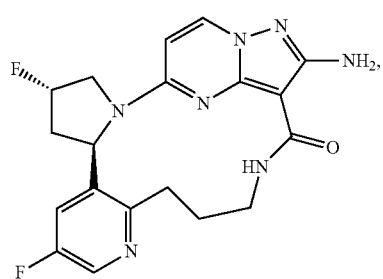
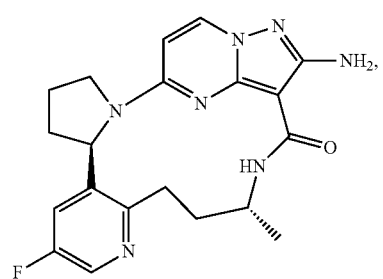
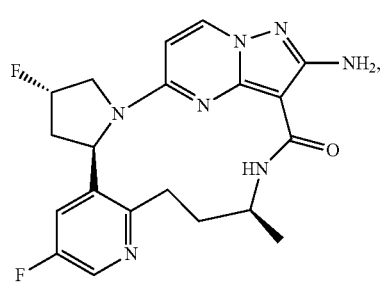
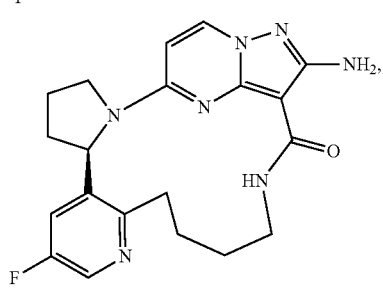
-continued
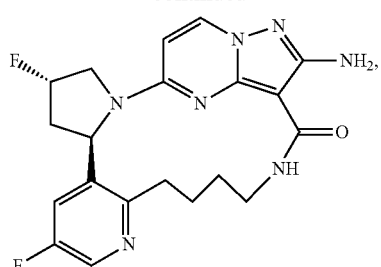
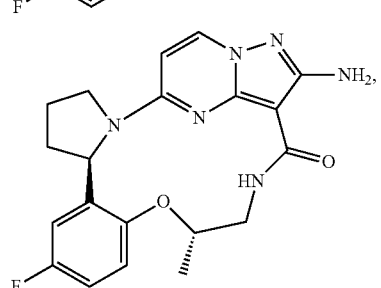
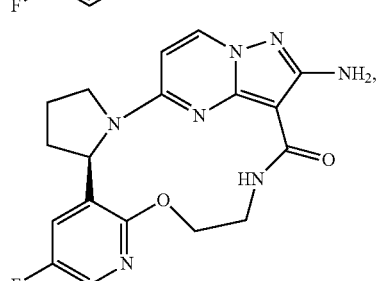
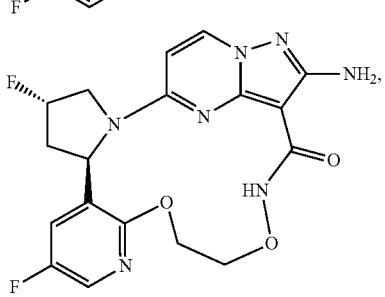
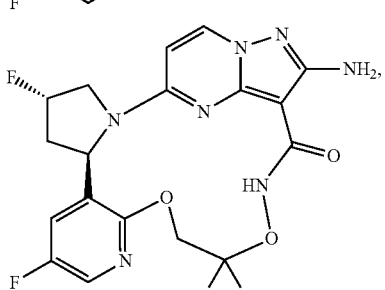
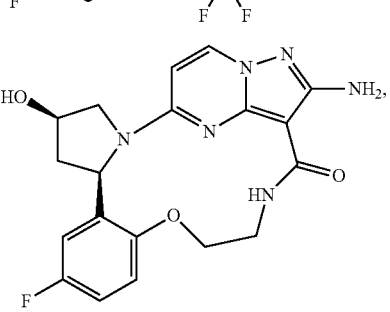

-continued

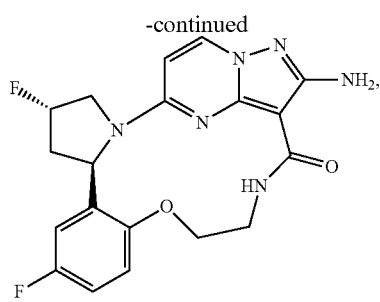

and a pharmaceutically acceptable salt thereof.

12. A pharmaceutical composition comprising the compound of Formula (I) according to claim 1, or a pharmaceutically acceptable salt thereof.

13. A method for ameliorating, eliminating, inhibiting, alleviating, or combinations thereof, a disease mediated by Trk kinase in a mammal, comprising administering to the mammal in need thereof a therapeutically effective amount of the compound of Formula (I) according to claim 1, or a pharmaceutically acceptable salt thereof, wherein the disease is a tumor.

14. The compound of claim 4, wherein $R^5$ is selected from the group consisting of hydrogen and methyl.

15. The compound of claim 5, wherein $R^1$ and $R^2$ are independently selected from the group consisting of hydrogen, fluoro, and methyl.

16. The compound of claim 1, wherein the structural unit

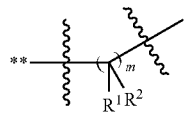

is selected from the group consisting of

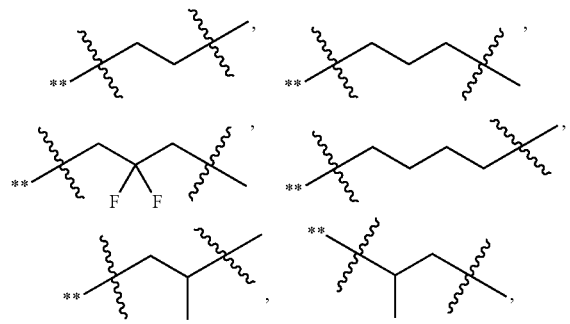

-continued

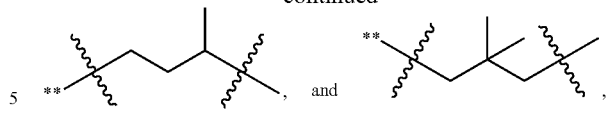

wherein ** represents the end of the structural unit

attached to X.

17. The compound of claim 7, wherein $R^3$ is selected from the group consisting of fluoro, chloro, bromo, iodo, and hydroxy.

18. The compound of claim 8, wherein n is selected from 0 or 1.

19. The compound of claim 9, wherein Cy is selected from the group consisting of a benzene ring, pyridine, and 1,2-2H-pyridine, each of which is optionally substituted with one or more substituents independently selected from the group consisting of fluoro and (=O).

20. The compound of claim 9, wherein Cy is selected from the group consisting of

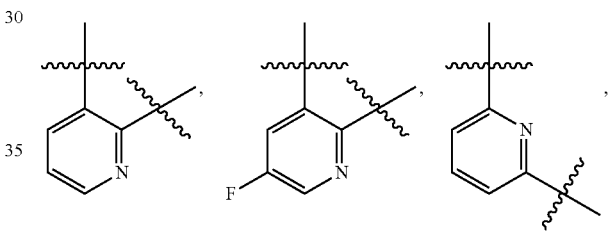

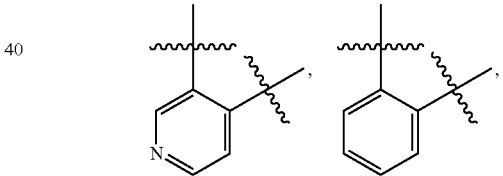

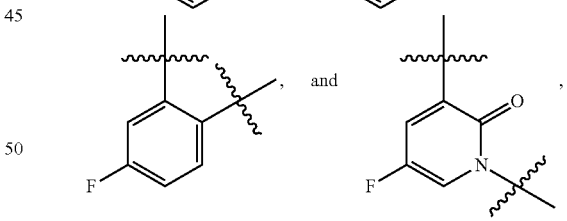

* * * * *